United States Patent [19]
Ravetch et al.

[11] Patent Number: 5,877,396
[45] Date of Patent: Mar. 2, 1999

[54] MICE MUTANT FOR FUNCTIONAL FC RECEPTORS AND METHOD OF TREATING AUTOIMMUNE DISEASES

[75] Inventors: Jeffrey V. Ravetch, New York, N.Y.; Toshiyuki Takai, Okayama, Japan; Diana Sylvestre; Raphael Clynes, both of New York, N.Y.

[73] Assignee: Sloan Kettering Institute for Cancer Research, New York, N.Y.

[21] Appl. No.: 292,569

[22] Filed: Aug. 18, 1994

Related U.S. Application Data

[63] Continuation-in-part of PCT/US94/04467, Apr. 22, 1994, which is a continuation-in-part of Ser. No. 52,267, Apr. 23, 1993, abandoned.

[51] Int. Cl.[6] ............ A61K 49/00; C12N 15/00; G01N 31/00
[52] U.S. Cl. ............ 800/2; 435/172.3; 424/9.1; 424/9.2
[58] Field of Search ............ 800/2; 424/9.1, 424/9.2, 9.34; 435/172.1, 172.9, 7.2, 69.1, 69.6, 240.1, 320.1; 536/23.1, 23.2, 23.4, 23.5, 24.1

[56] References Cited

U.S. PATENT DOCUMENTS 4,686,282  8/1987  Hahn ........................... 530/327
5,198,342  3/1993  Maliszewski ................... 435/69.1

OTHER PUBLICATIONS

Takai, et al., *Cell* (Feb. 1994) 76:519–529.
Love, P.E., et al., *Science* (Aug. 1993) 261:918–921.
Kuster, H., et al., *J. Biol. Chem.* (Apr. 1990) 265(11): 6448–6452.
Alcaraz, G., et al., *Biochemistry* (May 1987) 26(9): 2659–2575.
Ra, C., et al., *J. Biol. Chem.* (Sep. 1989) 264(26): 15323–15327.
Bruggemann et al. 1989. Proc. Natl. Acad. Sc., USA. 86:6709–6713.

*Primary Examiner*—Brian R. Stanton
*Attorney, Agent, or Firm*—John P. White

[57] ABSTRACT

Disclosed herein is a non-naturally occurring non-human vertebrate animal incapable of expressing a functional Fc receptor which may optionally be capable of expressing a protein which comprises a domain of a human Fc receptor, as well as DNA encoding such Fc receptor-based proteins. Also disclosed are in vivo methods for identifying proinflammatory agents that depend on a functional Fc receptor, in vivo methods for identifying proinflammatory agents that do not depend on a functional Fc receptor, and both in vivo and in vitro methods of identifying anti-inflammatory agents. Pharmaceutical compositions containing, and methods of treating inflammation with anti-inflammatory agents are also described.

18 Claims, 48 Drawing Sheets

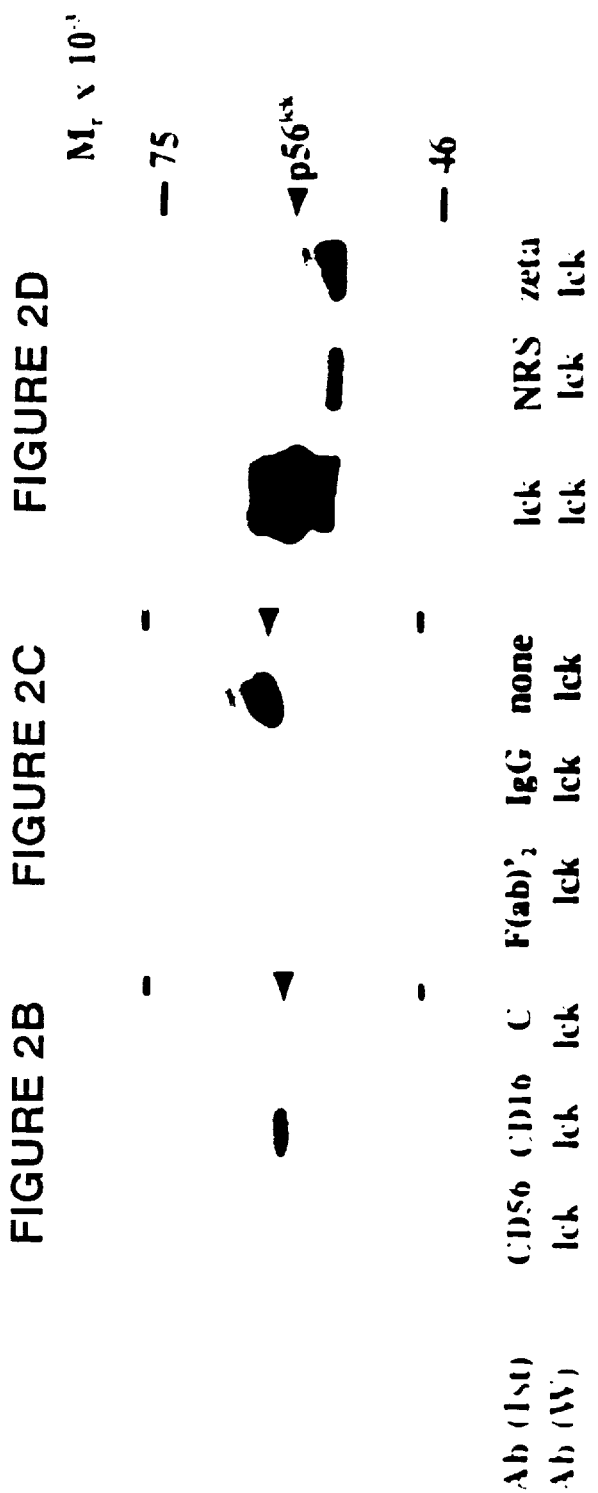

FIGURE 3A  FIGURE 3B  FIGURE 3C

DNA   $III_A/Z + fyn$     $III_A/Z + yes$     $III_A/Z + lck$

— fyn     — yes     — lck

Ab(1st)  ζ  C  —     ζ  C  —     ζ  C  —
Ab(W)    fyn          yes          lck

FIGURE 3D

DNA   ζ+lck   ζ+lck   γ+lck   γ+lck

≥ lck

Ab(1st)  C   ζ   C   γ
Ab(W)        lck

IgM/Igβ

IgM/Igα

IgM/Igβ

IgM/Igα probe A

Neo probe probe B probe C

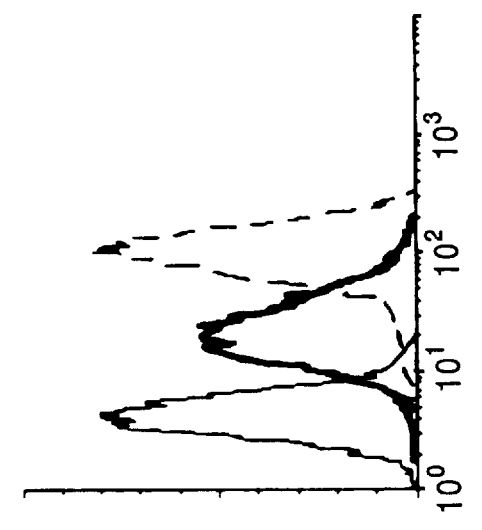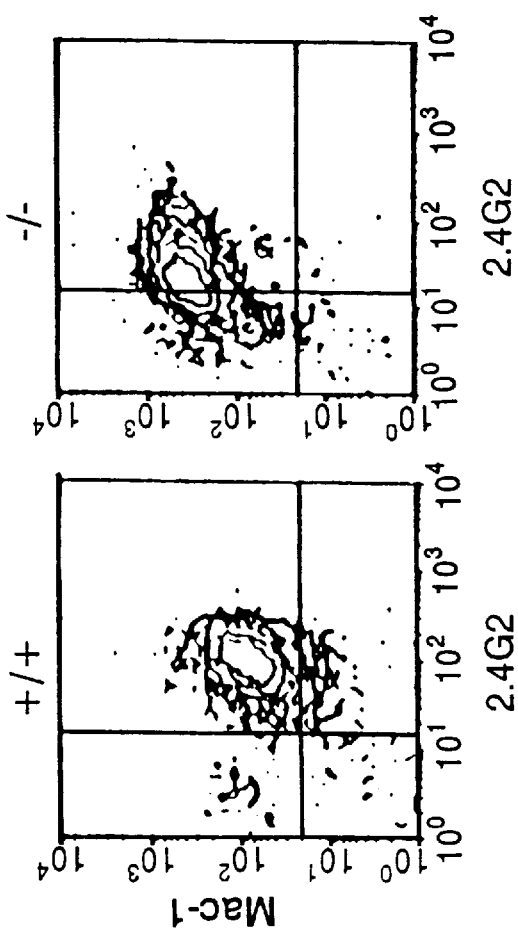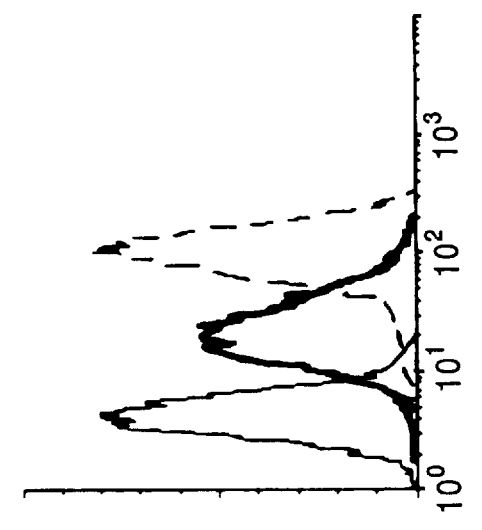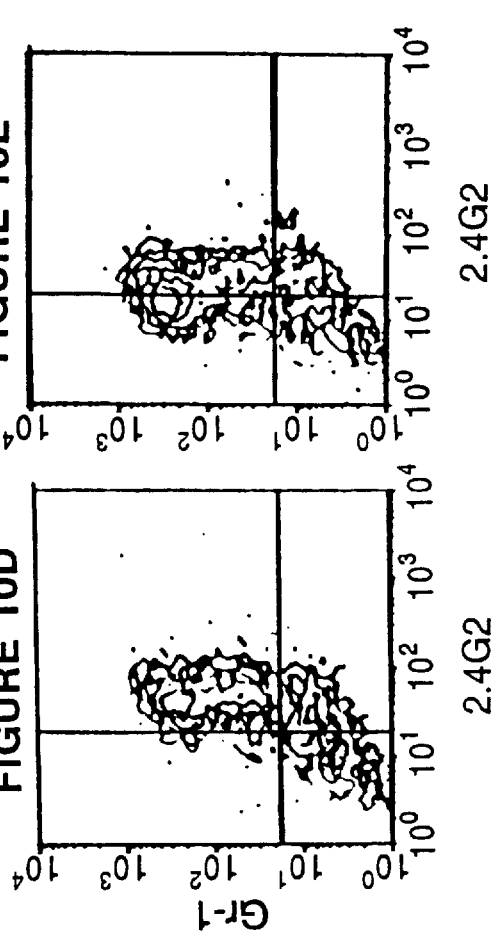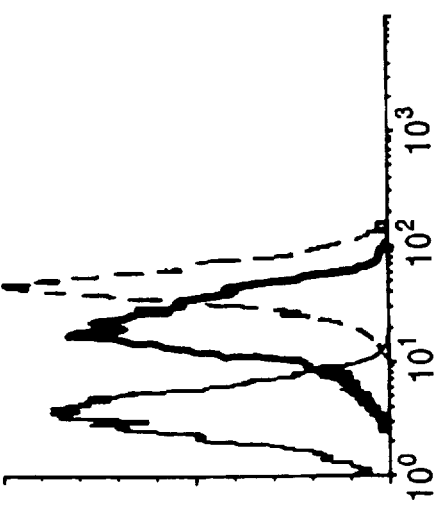

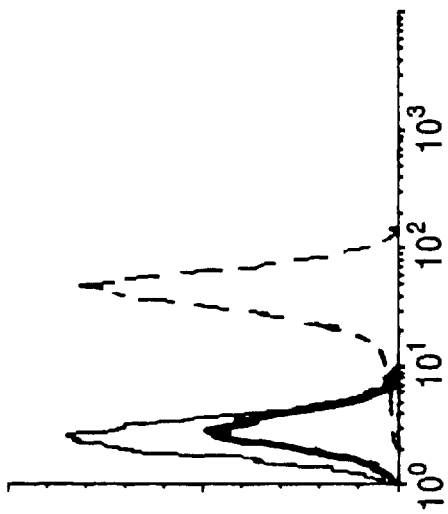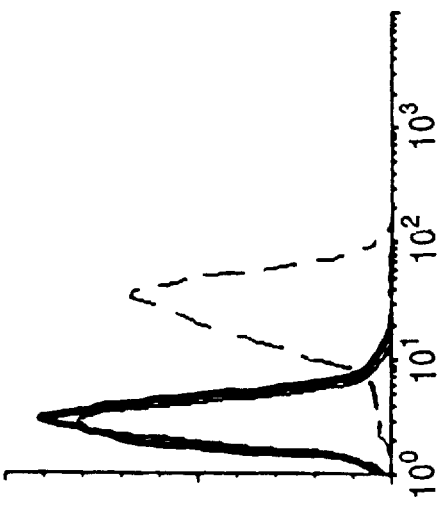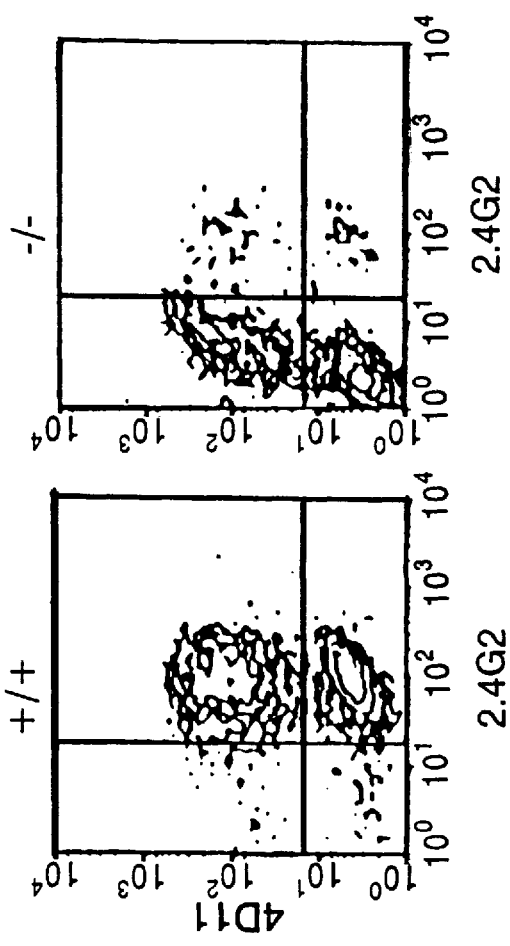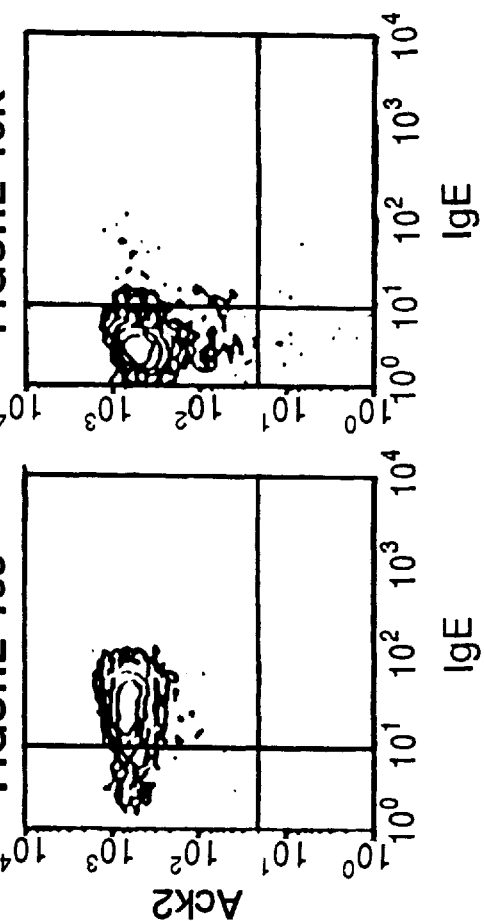

+/+

-/-

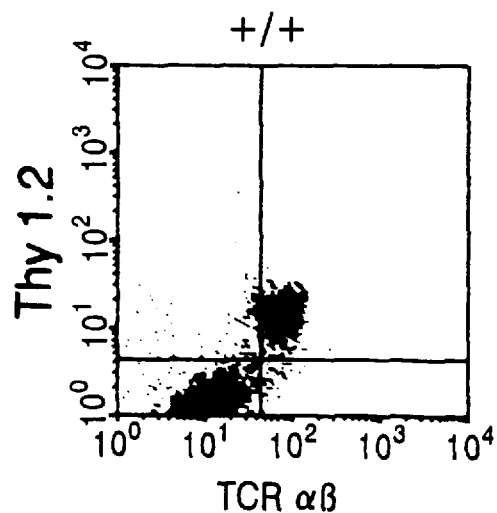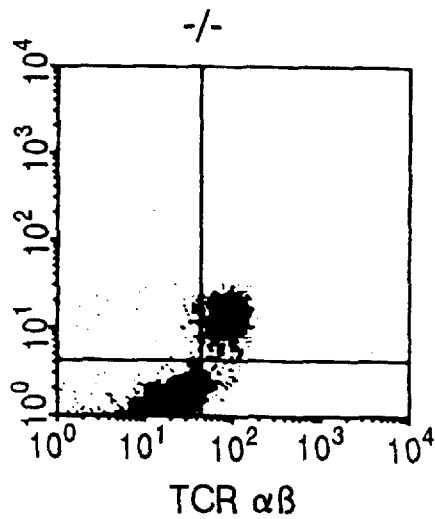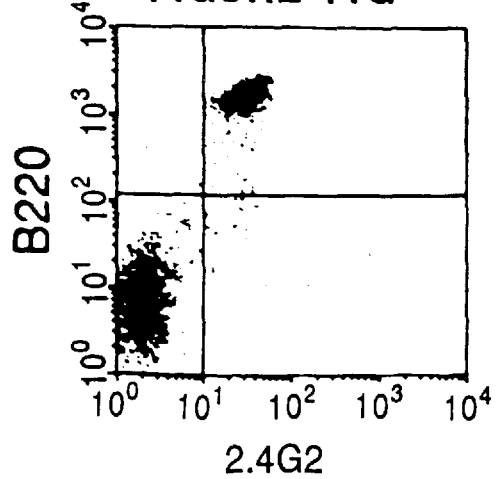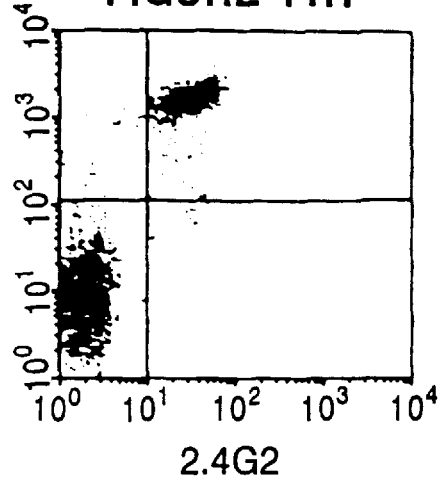

FIGURE 12A
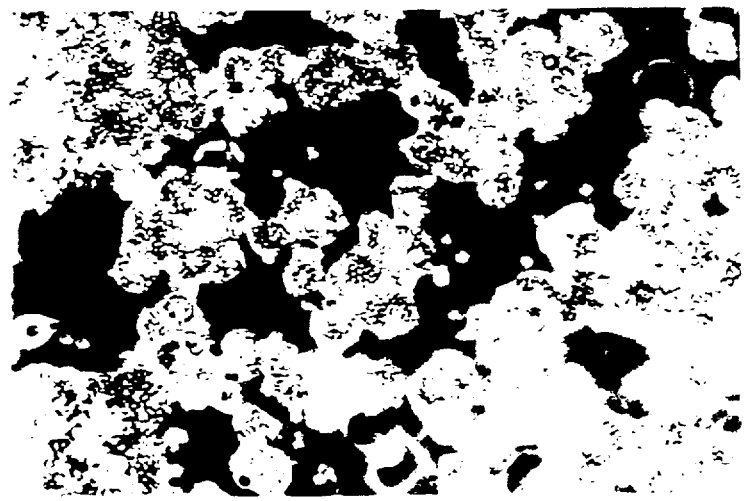
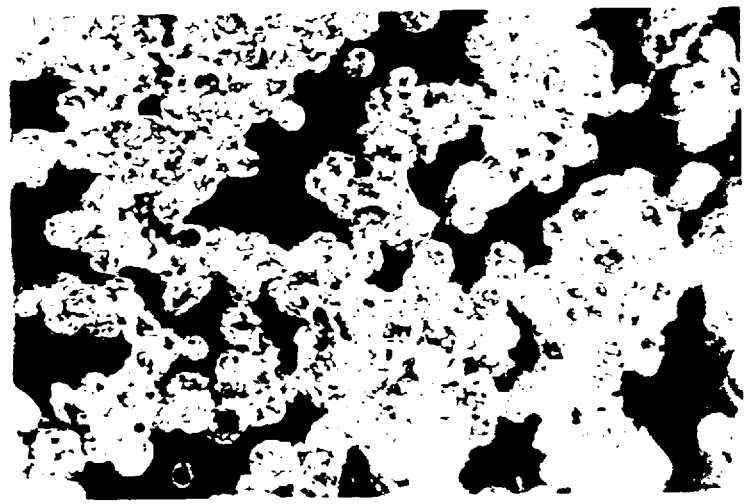
FIGURE 12B

FIGURE 12C
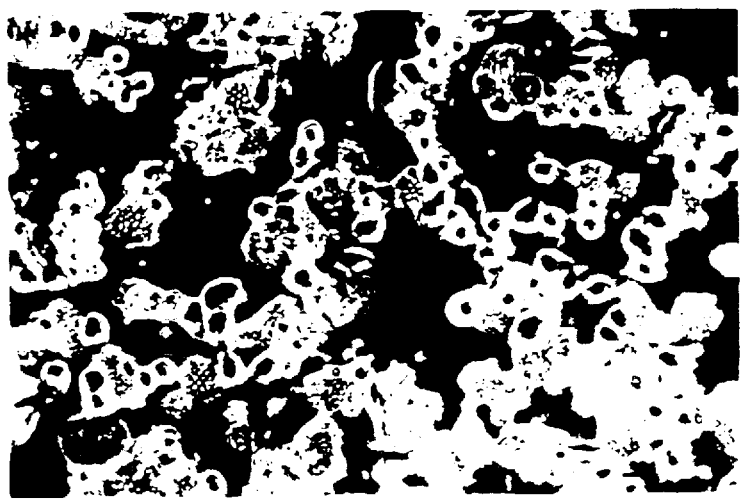
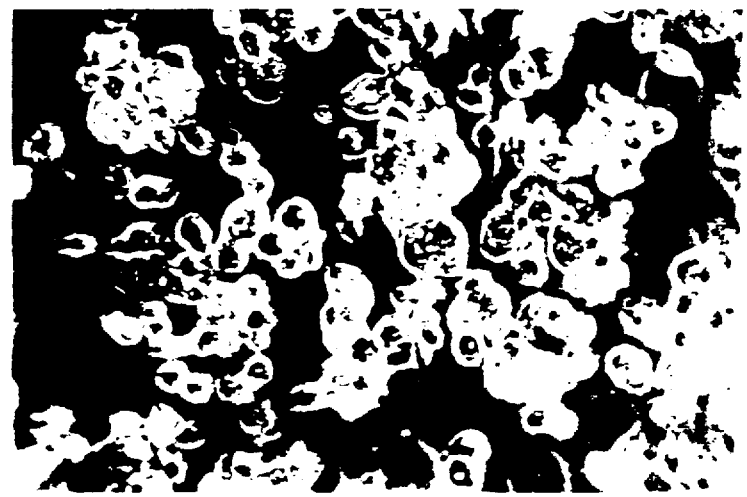
FIGURE 12D

FIGURE 12E
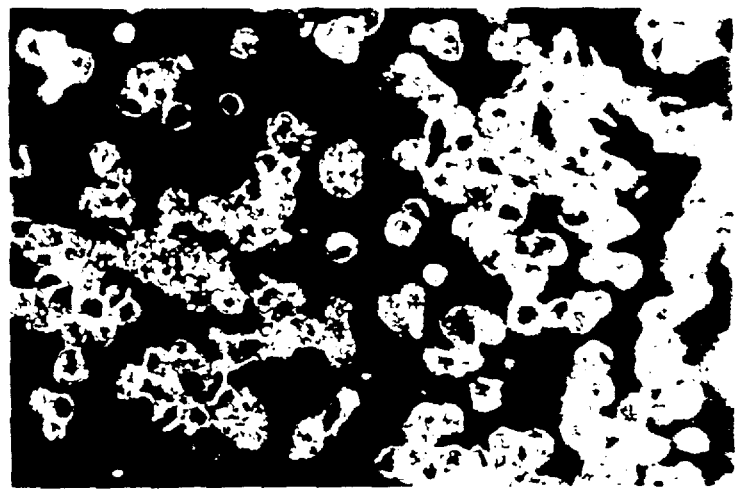
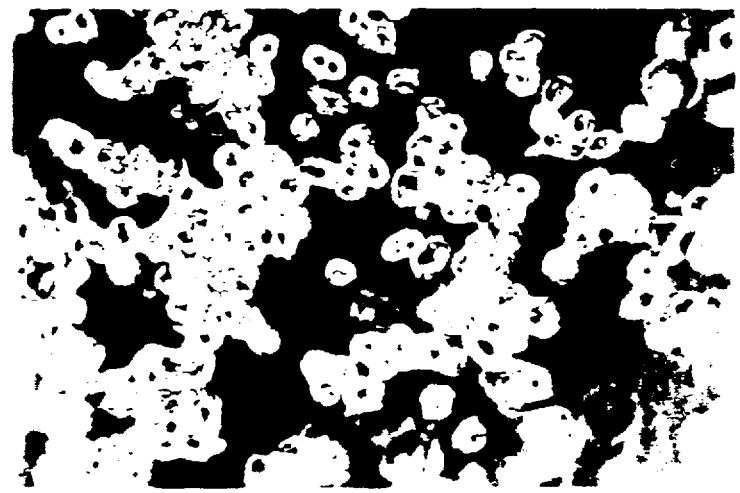
FIGURE 12F

FIGURE 12G
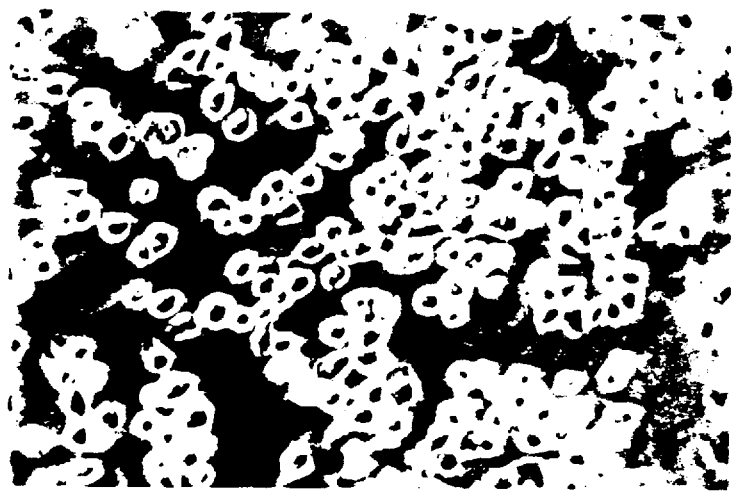
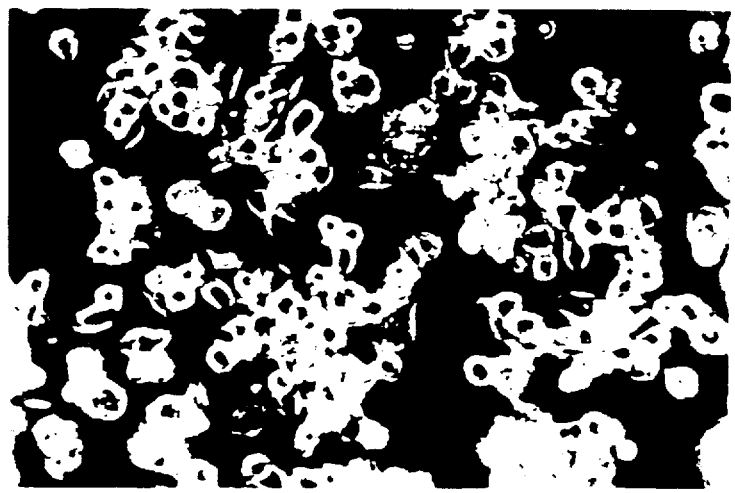
FIGURE 12H

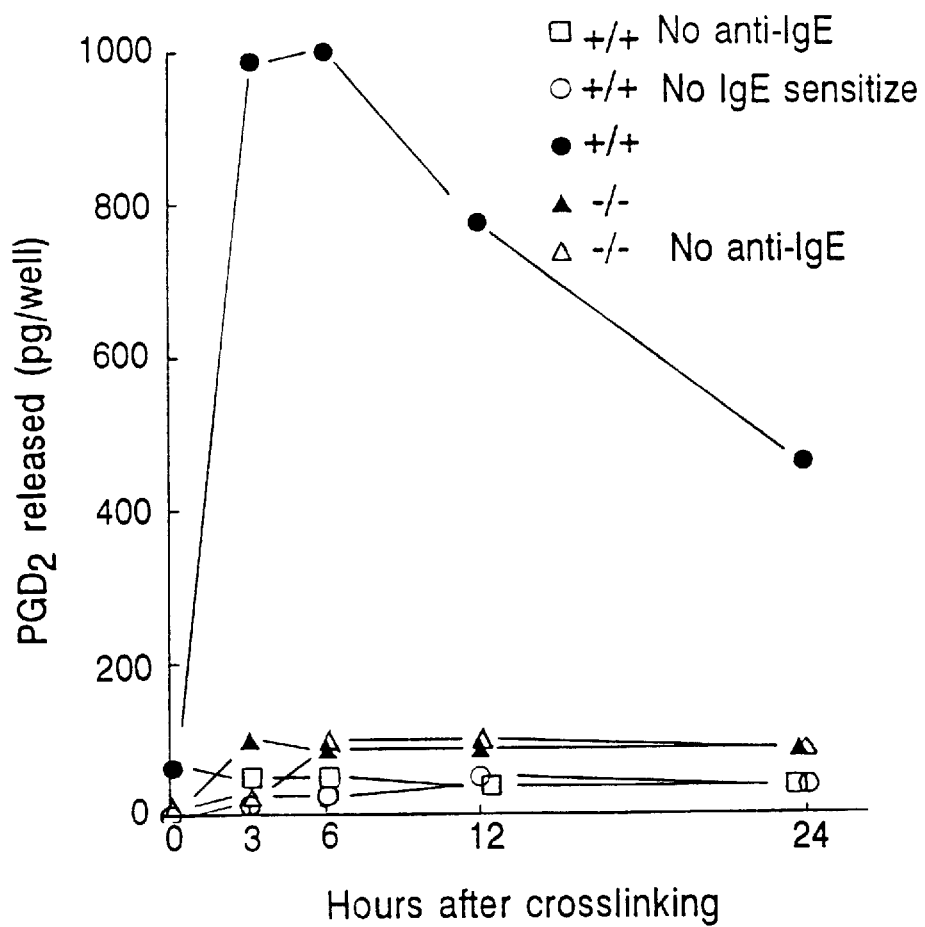

FIGURE 15A FIGURE 15B
Control α-OVA
+/+
-/-
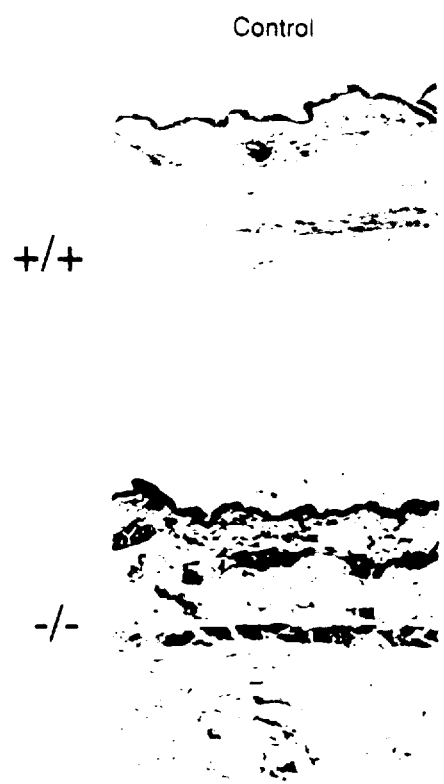
FIGURE 15C FIGURE 15D

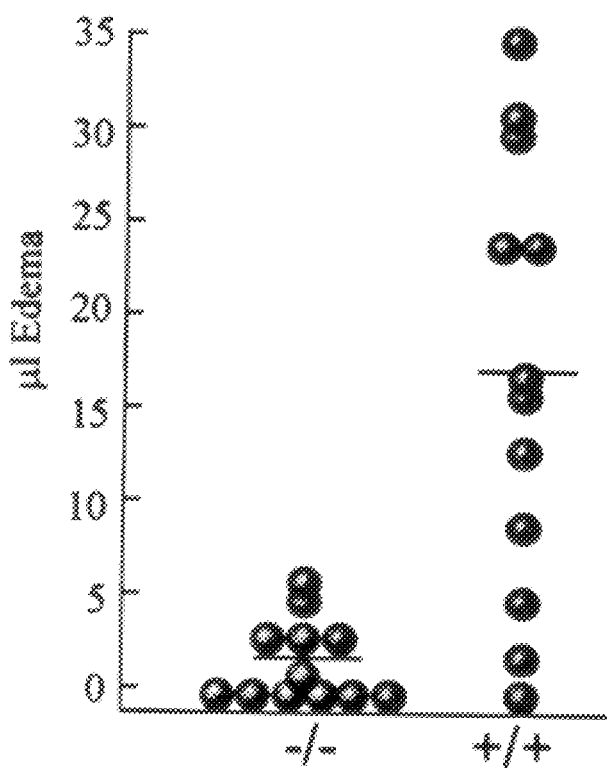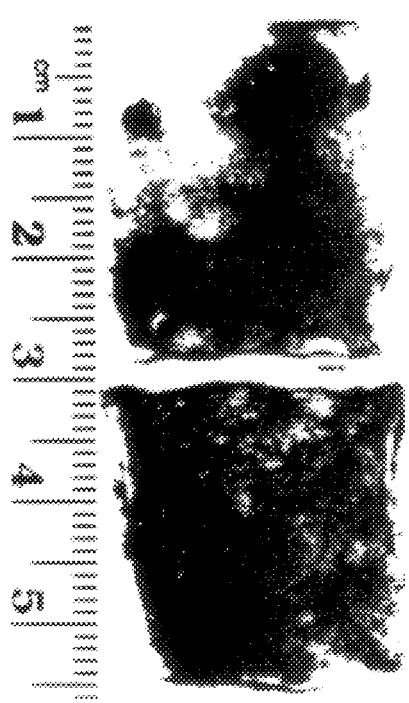

+/+  −/−

IgG3               Zymosan

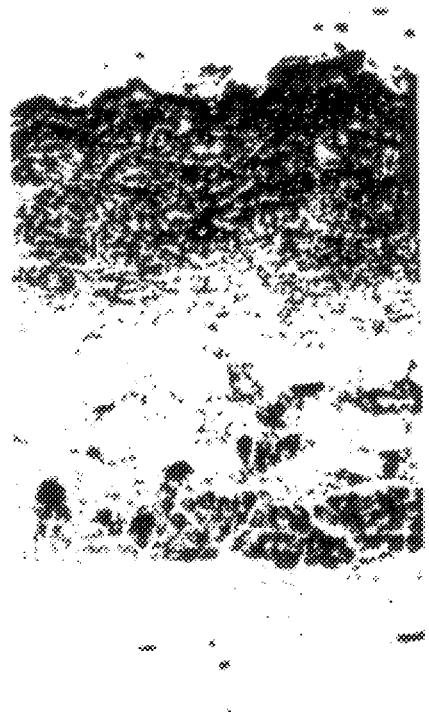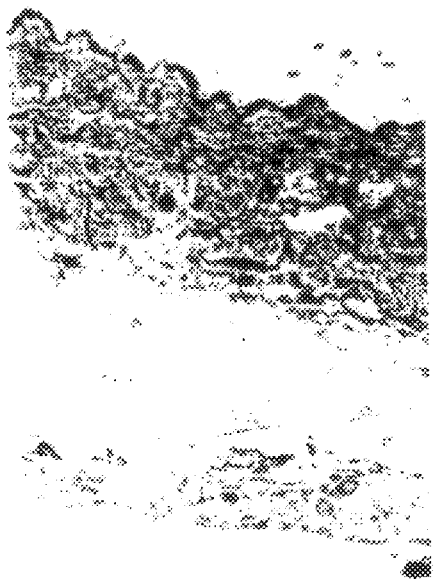
FIGURE 21A +/+    FIGURE 21B −/−

HUMAN FcR FAMILY

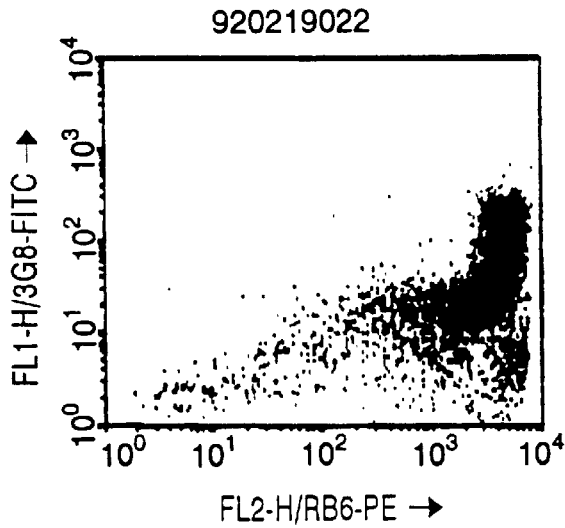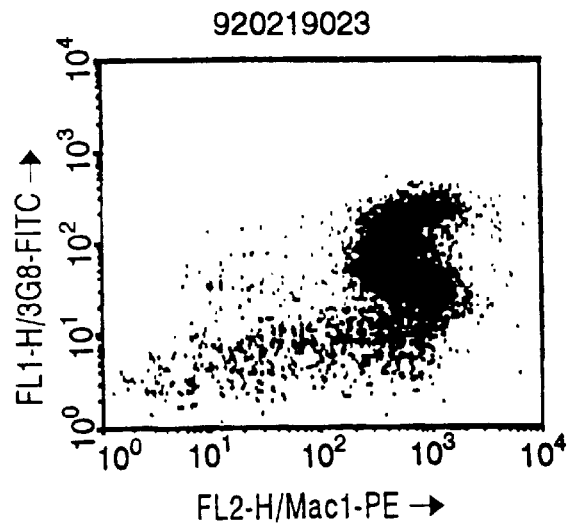
FIGURE 25E
FIGURE 25F

MICE MUTANT FOR FUNCTIONAL FC RECEPTORS AND METHOD OF TREATING AUTOIMMUNE DISEASES

This is a continuation-in-part of International Application No. PCT/US94/04467, International filing date Apr. 22, 1994, which is a continuation-in-part of U.S. Ser. No. 08/052,267, filed Apr. 23, 1993, the contents of which are hereby incorporated by reference.

This invention was made with support under National Institute of Health Grant No. GM 39256. Accordingly, the U.S. government has certain rights in the invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citations for these references may be found at the end of each section and in the body of the text.

The interaction of antibody-antigen complex with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. It is now well established that the diversity of cellular responses triggered by antibodies and immune complexes results from the structural heterogeneity of Fc receptors. Considerable progress has been made in the last several years in defining this heterogeneity for IgG and IgE Fc receptors (FcγR, FcεR) through their molecular cloning. Those studies make it apparent that Fc receptors share structurally related ligand binding domains, but differ in their transmembrane and intracellular domains which presumably mediate intracellular signalling. Thus, specific FcγRs and FcεR has also revealed at least one common subunit among some of these receptors.

It was recently observed that a family of disulfide-linked dimers are shared by Fc receptors and the T cell antigen receptor (TCR). Comparison of the genes for FcεRI (FcγRIII)γ and TCRζ chain indicates that they belong to the same family and have been generated by duplication. Both genes are located on mouse and human chromosome 1 and show an analogous organization of their exons. In both genes, the leader peptide is encoded by two exons, the second of which also contains the short extracellular domain, the hydrophobic transmembrane region, and the beginning of the cytoplasmic tail. The following exons, exons 3–5 and exons for γ and ζ, respectively, encode the remainder of the cytoplasmic tail. Furthermore, a high level of homology between the two genes is found in three of their respective exons, at the DNA and protein level (both about 50%). Finally, both γ and ζ polypeptides use homologous cysteines essential for the surface expression of their respective receptors.

The detection of transcripts for ζ chains in TCR-, CD3- NK cells led to the finding that human FcγRIIIAα from NK cells physically associates with ζ-ζ homodimer and with ζ-γ heterodimer. So far, three different dimers have been identified in Fc receptor complexes: γ-γζ-ζ and ζ-γ. These dimers are also part of the TCR complex and probably mediate similar functions. There is a third member of the same family, TCRη which is generated by alternate splicing from the same gene as TCRζ. The dimers η-η, η-ζ, and η-γ apparently are only associated with TCR, and so far there is no evidence that they associate with Fc receptor structures. Possibly, new members of the same family will be identified that form part of Fc receptor complexes.

Fc receptors (FcRs) for IgG and IgE couple humoral and cellular immunity by directing the interaction of antibodies with effector cells. These receptors are present on most effector cells of the immune system and mediate phagocytosis, antibody-dependent cell-mediated cytotoxicity (ADCC), activation of inflammatory cells and many of the biological sequelae associated with antibody-dependent immunity (reviewed in Ravetch and Kinet, 1991; Beaven and Metzger, 1993). Intensive analysis of the genes and proteins encoded by this family of receptors has revealed a structural heterogeneity for these receptors which mirrors the functional diversity mediated by these cell surface molecules (Ravetch, et al., 1986).

The high affinity FcR for IgE, FcεRI, is found on mast cells and basophils, and is responsible for the degranulation of these cells in response to crosslinking by antigen (reviewed in Parker, 1987). It is the receptor primarily responsible for triggering both peripheral and systemic anaphylaxis. In addition to the well known pathological response of these cells when activated by allergen, FcεRI has been associated with host resistance to parasitic infections (Matsuda et al., 1990). In contrast to the restricted expression of FcεRI, FcRs for IgG, FcγRs, are found on most cells of the hematopoietic lineage, and mediate both high and low affinity binding to IgG. The high affinity receptor, FcγRI, binds monomeric IgG and is expressed exclusively on macrophages and neutrophils. It is capable of mediating ADCC and phagocytosis in response to crosslinking by antibody (Askenase and Heyden, 1974, Heusser, et al. 1977; Diamond et al. 1978). The low affinity receptors for IgG, FcγRII and FcγRIII, are responsible for effector cell responses to immune complexes and represent the FcγRs primarily involved in the inflammatory response in vivo. FcγRII is widely expressed on haematopoietic cells and functions as an inhibitory receptor on B cells (Uhen, et al., 1985; Kurosaki, et al. 1993), while on cells of the myeloid lineage and on platelets, FcγRII triggers ADCC, phagocytosis and the release of inflammatory mediators when crosslinked by immune complexes (Nathan, et al. 1980). These disparate functions result from the genetic heterogeneity of FcγRII, as well as alternative splicing of its mRNA to generate proteins with distinct intracellular domains (Stuart, et al., 1989; Brooks, et al., 1989; Qiu, et al.,1990). FcγRIII is restricted in its expression to NK, macrophage, neutrophils and mast cells, and mediates effector responses when crosslinked by immune complexes (Weinshank, et al., 1988; Perussia, et al., 1989). It is the sole FcR on NK cells, mediating all the antibody-dependent responses on those cells. In addition to these well-characterized effector cell pathways, FcγRIII has been found on immature (day 15) thymocytes, where it has been postulated to function in early thymocyte development (Rodewald, et al., 1992).

Molecular characterization of the genes and protein products for FcγRIII and FcεRI revealed that these two receptors were homologous (Ravetch and Anderson, 1989; Ravetch and Kinet, 1991) and required the identical subunit, the γ chain, for efficient cell surface expression (Ra, et al. 1989; Kurosaki and Ravetch, 1989). This homodimeric protein not only mediates assembly of these receptors by preventing the degradation of the ligand binding α subunit in the endoplasmic reticulum (Weissman, et al., 1989; Kurosaki, et al.

1991), it is also critical for transducing signals into the cell interior resulting in cellular activation through a tyrosine kinase-dependent pathway (Romeo and Seed, 1991; Wirthmueller, et al., 1992). In murine macrophages, neutrophils, mast cells and basophils, the γ chain is necessary for surface expression of FcγRIII and FcεRI. In NK cells, a homologous chain, the ζ chain, first described as a component of the TCR/CD3 complex, is also expressed and forms heterodimers with the γ chain (Kurosaki and Ravetch, 1989; Lanier, et al., 1989). Based on reconstitution studies and in vitro experiments, the murine ζ chain alone cannot substitute for γ chain, due to a single amino acid substitution in the transmembrane domain of this ζ replacing a leucine for an isoleucine (Kurosaki and Ravetch, 1989; Kurosaki et al., 1991). This change in the transmembrane domain greatly diminishes the association of ζ chain with the ligand binding a chain. The γ chain has also been found to be associated with the TCR/CD3 complex (Mercap et al., 1990), although its specific function, distinguishing it from the homologous ζ, chain has yet to be determined. Although not required for its surface expression or ligand binding in transfected fibroblasts, the γ chain has been found to be associated with FCγRI in the human monocytoid line U937 (Ernst, et al. 1992), where it may function as a signal transducing subunit.

The tissue deposition of immune complexes in diseases as diverse as rheumatoid arthritis, systemic lupus erythematosis, glomerulonephritis, and vasculitis is widely recognized as a major pathogenic factor triggering the inflammatory cascade, leading to tissue damage and its subsequent morbidity and mortality. The most widely employed experimental model for the study of the pathological effects of antibody-antigen interaction is the Arthus phenomenon, first described by Maurice Arthus in 1903 (1). It was first characterized as the acute local inflammation and hemorrhage produced when an intradermal injection of horse serum was administered to previously sensitized rabbits, and its manifestations are a direct result of immune complex formation and deposition: edema due to increased vascular permeability and local mediator release, neutrophil infiltration in response to the local formation of chemotactic peptides, hemorrhage due to damage to the blood vessel wall, and in severe cases, tissue damage produced by the release of lysosomal enzymes. The study of the mechanisms and inhibitors of this reaction thus has broad relevance to the understanding of immune complex-mediated diseases and has provided important insights into the understanding of the process of inflammation.

Because the induction of the direct Arthus reaction suffers from substantial intra- and interspecies variability in the immunologic responsiveness to a foreign antigen, a number of experimental variants of the original Arthus reaction have been developed. The one which best minimizes the difficulties with reproducibility and generalizability is the reverse passive Arthus reaction, in which heterologous antibody is injected into the skin and cognate antigen is injected intravenously; immune complexes are formed locally in the skin as circulating antigen diffuses into the tissue and binds to its antibody. Since it is independent of host response to specific antigens in the levels and specificity of antibodies generated, this variant maximizes the detection of host factors necessary to the inflammatory response and as such has allowed elucidation of the many elements contributing to this complex cascade.

The first definitive experiments demonstrating that serum antibody was necessary to the Arthus reaction were performed by Opie in 1924 (2); subsequent experiments by Culbertson, Cannon and Marshall, Fishel and Kabat, and Benacerraf and Kabat (3) correlated the actual quantity of antibody with the intensity of the reaction. Using fluorescent antibody techniques, Cochrane and Weigel in 1958 (4) demonstrated the presence of both antigen and antibody in histologic lesions, supporting the hypothesis first put forth by Opie (2) more than a quarter of a century earlier that the Arthus reaction was produced by the local formation of antigen-antibody complexes.

That polymorphonuclear leukocytes play a critical role in the Arthus reaction was demonstrated independently in the 1950's by Stetson, Humphrey and Cochrane, et. al. (5). Animals which were depleted of neutrophils with either nitrogen mustard or anti-neutrophil antiserum showed markedly reduced Arthus reactions, despite the continued presence of antibody-antigen complexes. In 1964, Ward and Cochrane (6) demonstrated the integral role of complement to the production of the Arthus reaction by pre-treating animals with cobra venom factor, which cleaves the C3 component of complement and inactivates the cascade. In the absence of complement, neutrophil infiltration was substantially attenuated, consistent with the key role of complement in inflammatory activation. Once it became known that immune complexes can bind and activate complement directly via the "classical pathway" (7) and that activated complement components are themselves potently chemotactic for neutrophils (8), a model of immune complex-triggered inflammatory disease was proposed which has persisted to this day.

In this model, antibodies bind to their antigen to form immune complexes, which results in complement binding and activation via the "classical pathway". The resulting chemotactic peptides cause neutrophil invasion and activation, with subsequent discharge of granules (degranulation) and release of inflammatory mediators. The direct consequences of this cascade are the classical symptoms of inflammation—edema, hemorrhage and tissue destruction. However, this model has not addressed the potential role of specific cell-surface receptors known to bind antibody-antigen complexes and activate effector cells. These well-defined receptors, collectively known as Fc receptors for their binding of the Fc portion of antibodies, mediate macrophage, neutrophil, NK cell and mast cell activation in vitro and are capable of triggering many of the responses classically associated with inflammation (9).

Fc receptors are members of the immunoglobulin superfamily and exist as membrane-associated glycoproteins. Distinct receptors are expressed for each isotype of antibody. Among the IgG Fc receptors, three classes of molecules have been defined, varying in structure and affinity for IgG. FcγRI, present on monocytes and macrophages, is the only Fc receptor capable of binding monomeric antibody, due to its relatively high ligand affinity. FcγRII and FcγRIII are both low affinity receptors and will only bind antibody in the form of immune complexes. FcγRII is expressed widely on hematopoietic cells, whereas FCγRIII expression is generally limited to monocytes, NK cells, neutrophils, and mast cells.

Fc receptors are generally hetero-oligomeric receptors, composed of a ligand binding subunit α, and in the case of FcεRI, FcγRI and FcγIII of a dimeric ζ or γ chain, required for surface expression and signal transduction. While the α subunits of murine FcγRII and III are nearly identical in their extracellular domains, they have distinct transmembrane and intracytoplasmic regions, which mediate their interaction with associated subunits and thus result in the activation of different signaling pathways (9). Dissecting the role of individual Fc receptors in vivo has been complicated by the overlapping expression of this large family of related receptors, each of which can bind immune complexes and mediate effector cell response.

An oligopeptide which blocks immune complex binding to immunoglobulin Fc receptors is disclosed in U.S. Pat. No. 4,686,282 (Hahn, 1987).

U.S. Pat. No. 5,198,342 (Maliszewski, 1933) discloses DNA encoding IgA Fc receptors.

SUMMARY OF THE INVENTION

This invention provides a non-naturally occurring non-human vertebrate animal incapable of expressing a functional Fc receptor. This invention also provides a mutated form of isolated vertebrate genomic DNA encoding a functionally deficient Fc receptor.

This invention provides a non-naturally occurring non-human vertebrate animal incapable of expressing a functional non-human Fc receptor capable of expressing a protein which comprises a domain of a human Fc receptor. This invention also provides an isolated DNA molecule comprising a cell type expression regulating sequence; and a sequence encoding a protein which contains a domain of a human Fc receptor under transcriptional control of the cell type expression regulating sequence.

This invention provides a method for identifying a proinflammatory agent dependent on a functional Fc receptor, comprising: administering to a mouse capable of expressing a functional Fc receptor and to a mouse incapable of expressing a functional Fc receptor, an amount of the proinflammatory agent effective to induce an inflammatory response in the mouse capable of expressing the functional Fc receptor; and determining less inflammatory response in the mouse incapable of expressing the functional Fc receptor than in the mouse capable of expressing the functional Fc receptor, thereby identifying the proinflammatory agent dependent on the functional Fc receptor.

This invention provides a method for identifying a proinflammatory agent not dependent on a functional Fc receptor, comprising: administering to a mouse incapable of expressing the functional Fc receptor an amount of the proinflammatory agent effective to induce an inflammatory response; and detecting an inflammatory response in the mouse incapable of expressing the functional Fc receptor, thereby identifying the proinflammatory agent not dependent on the functional Fc receptor.

This invention provides a method of identifying an anti-inflammatory agent, comprising: administering to a test mouse according to claim 46 an amount of a proinflammatory agent capable of inducing an inflammatory response in the mouse in the absence of the anti-inflammatory agent, and an inflammation inhibiting effective amount of the anti-inflammatory agent; and determining decreased inflammatory response, thereby identifying the anti-inflammatory agent. This invention also provides an anti-inflammatory agent identified by this method.

This invention further provides a method for inhibiting stimulation of Fc receptor-bearing cells in a subject, comprising administering to the subject an amount of the anti-inflammatory agent identified by the above-described method effective to inhibit stimulation of the Fc receptor-bearing cells in the subject.

This invention also provides a method for treating a Fc receptor-dependent condition in a subject, comprising administering to the subject an amount of the anti-inflammatory agent identified by the above-described method effective to treat the Fc receptor-dependent condition in the subject.

This invention provides a method for identifying an agent capable of inhibiting a complex of a protein and a ligand capable of binding to the protein in the absence of the agent, the protein comprising an extracellular domain of a Fc receptor or Fc receptor subunit, comprising: incubating a first incubation cocktail which contains the protein, the ligand, and the agent, and a second incubation cocktail which contains the protein and the ligand but not the agent; detecting the amount of protein-ligand complex in the first and second incubation cocktails; and determining less protein-ligand complex in the first cocktail than in the second cocktail, thereby identifying the agent capable of inhibiting a complex of the protein and the ligand. This invention also provides a complex-inhibiting agent identified by the above-described method.

This invention further provides a method for inhibiting stimulation of Fc receptor-bearing cells in a subject, comprising administering to the subject an amount of the complex-inhibiting agent identified by the above-described method effective to inhibit stimulation of the Fc receptor-bearing cells in the subject.

This invention also provides a method for treating a Fc receptor-dependent condition in a subject, comprising administering to the subject an amount of the anti-inflammatory agent identified by the above-described method effective to treat the Fc receptor-dependent condition in the subject.

BRIEF DESCRIPTION OF THE FIGURES

First and Second Series of Experiments

PBL, obtained by density gradient centrifugation of venous peripheral blood from healthy donors, were cultured with 30-Gy irradiated RPMI-8866 B lymphoblastoid cells. NK cells were purified from 10-d cocultures by negative selection after sensitization with anti-CD3 (OKT3), anti-CD5 (B36.1), and anti-CD14 (B52.1) monoclonal antibody (mAb) and indirect anti-globulin resetting (7). The purity of each preparation (>95%) was confirmed in indirect immunofluorescence (flow cytometry) using a panel of mAb.

The indicated src-related kinases (indicated by the arrowhead) were immunoprecipitated from postnuclear supernatants of NK cells lysed in 1% Triton X100, 1% sodium deoxycholate, 0.1% SDS, 150 mM NaCl, 10 mM Tris, 5 mM EDTA using protein A-Sepharose (for rabbit polyclonal antisera) or protein A-Sepharose coated with anti-mouse Ig (anti-src mAb). Precipitates were washed twice with lysis buffer and once with 100 mM NaCl, 10 mM NaCl, 10 mM Tris, pH 7.5, 5 mM $MnCl_2$. The products of in vitro kinase assays (4), performed for 15 min. on ice, were analyzed in reducing 7.5% SDS-PAGE.

Figure 1A:
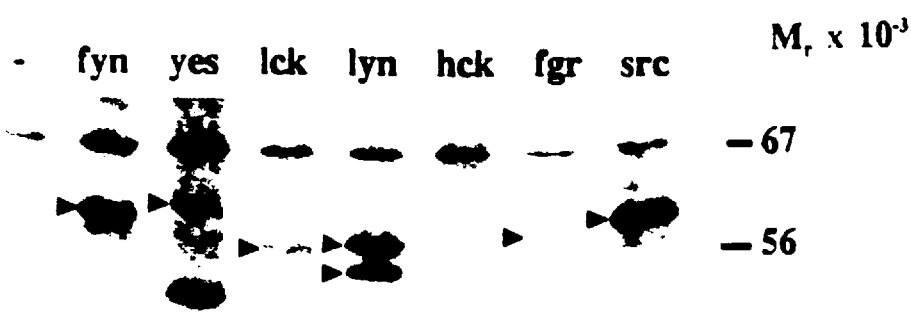
FIG. 1A. Expression and activation of $p56^{lck}$ in NK cells.
Figure 1B:
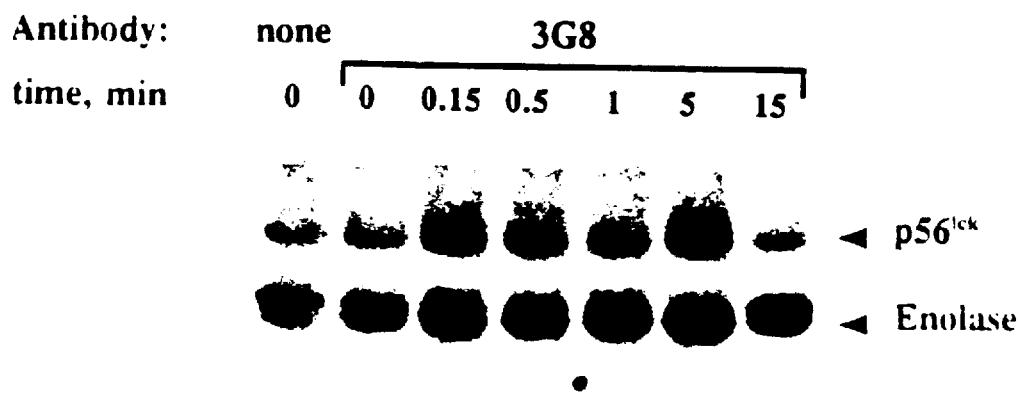

FIG. 1B. Expression and activation of $p56^{lck}$ in NK cells.

PBL, obtained by density gradient centrifugation of venous peripheral blood from healthy donors, were cultured with 30-Gy irradiated RPMI-8866 B lymphoblastoid cells. NK cells were purified from 10-d cocultures by negative selection after sensitization with anti-CD3 (OKT3), anti-CD5 (B36.1), and anti-CD14 (B52.1) monoclonal antibody (mAb) and indirect anti-globulin rosetting (7). The purity of each preparation (>95%) was confirmed in indirect immunofluorescence (flow cytometry) using a panel of mAb.

NK cells ($5 \times 10^6$/ml RPMI) were incubated for the indicated times with anti-CD16 mAb 3G8. After incubation and lysis in 1% NP-40, $p56^{lck}$ was precipitated from the postnuclear supernatants. Kinase assay was performed after addition of 1 μg enolase an the product of the kinase assay was analyzed in reducing 7.5% SDS-PAGE. No increased phosphorylation of $p56^{lck}$ or enolase was detected in $p56^{lck}$ inmunoprecipitates from NK cells stimulated with anti-CD56 mAb B159.5 used as control (not shown). Anti-$p56^{lck}$ serum was produced in rabbits immunized with a synthetic peptide corresponding to amino acids 39–64 of the murine $p56^{lck}$ protein sequence (4).

Figure 2A:
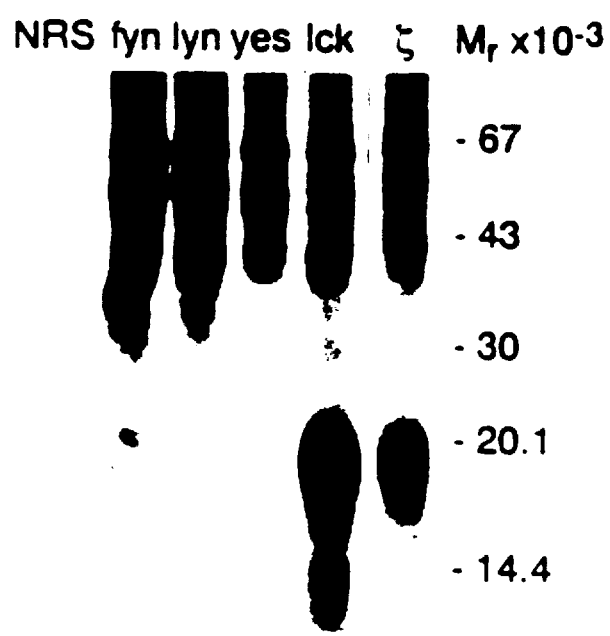

FIG. 2A. Association of $p56^{lck}$ with FcγRIIIA in NK cells.

FcγRIII was precipitated from NK cells ($10\times10^6$ cells per precipitation) lysed in 1% digitonin, 150 mM NaCl, 20 mM Tris, pH 8.1 mM PMSF, 10 μg/ml aprotinin, 10 μg/ml leupeptin using anti-CD16 mAb 3G8, and in vitro kinase assay was performed on the immunoprecipitate. Kinase products were eluted from the beads (1% NP-40, 1 h) and the indicated proteins were precipitated using specific antibodies or normal rabbit serum (NRS) as control. Inmunoprecipitates were analyzed in reducing 13% SDS-PAGE.

FIGS. 2B–2D. Association of $p56^{lck}$ with FcγRIIIA in NK cells.

FIG. 2B: Postnuclear supernatants from NK cells ($50\times10^6$ per precipitation), lysed as above, were precleared with goat anti-mouse:protein G for 30 min, and precipitated [Ab(1st)] with anti-CD16 mAb 3G8 or anti-CD56 mAb B159.5 coupled to goat anti-mouse Ig protein G-Sepharose was used to control (C). Immune complexes were washed 6 times with 0.2% digitonin lysis buffer and proteins analyzed in 7.5% reducing SDS-PAGE and Western blotting [Ab(W)] using anti-$p56^{lck}$ (rabbit polyclonal antisera, N-terminus specific, UBI, Lake Placid, N.Y.), and $^{125}$I-labeled goat anti-rabbit IgG. FIG. 2C: Postnuclear supernatants from NK cells ($35\times10^6$ cells per precipitation), lysed in digitonin buffer as above, were precleared (15 h) with CNBr-activated/quenched-Sepharose. Supernatants were precipitated with heat-aggregated (30 min, 63° C.) huIgG-Sepharose or F(ab')$_2$-Sepharose (control) for 5 h. Complexes were washed 6 times with lysis buffer and proteins analyzed on 7.5% reducing SDS-PAGE with Western blotting using anti-$p56^{lck}$ mAb (provided by Y. Koga), HRP-sheep anti-mouse Ig, and ECL. (None=lysate from approximately $10^6$ cell equivalents, no precipitation). FIG. 2D: Postnuclear supernatants from NK cells ($30\times10^6$ cells per precipitation), lysed in 2% NP-40, 150 mM NaCl, 20 mM Tris, 2 mM PMSF, 25 μg/ml each aprotinin, leupeptin, antipain, were precleared with protein A-Sepharose beads and incubated with rabbit antisera (anti-, anti-$p56^{lck}$, non-immune) followed by protein A-Sepharose precipitation. Beads were washed 5 times with lysis buffer and analyzed in 7.5% reducing SDS-PAGE with Western blotting for $p56^{lck}$ as in Panel B. The lower bands in C represent rabbit IgG used for precipitation.

FIGS. 3A–3C. Association of $p56^{lck}$ with γ and ζ chains.

COS cells were cultured in modified Eagle's medium containing 10% fetal calf serum. Mouse fyn cDNA (15) (from R. Perlmutter), human yes cDNA (16) (from T. Yamamoto and J. Sukegawa), and human lck cDNA (17) (from T. Mak) were cloned into the pCEXV-3 vector. DNA (15 μg each DNA/60 mm dish) was transfected into COS cells using the calcium-phosphate method (18) in the presence of 100 μM chloroquine. Transfected DNA are indicated at the top of each panel. The IIIA/ζ construct contained the extracellular region of FcγRIIIA and the transmembrane and cytoplasmic regions of human chain (19). Two days after transfection, cells were solubilized in lysis buffer (3% NP-40, 50 mM Tris pH 8, 150 mM NaCl, 50 mM NaF, 10 μM molibrate, 0.2 mM vanadate, 10 μg/ml aprotinin, 10 μg/ml leupeptin, 2.5 μg/ml antipain, 0.1 mM PMSF). Cell lysates were precleared with Sepharose, incubated with the indicated Ab [Ab (1st)] coupled-Sepharose for 2 h and washed with lysis buffer 5 times. Antibodies against γ and ζ chains (19) and control antibodies were purified by protein A-Sepharose and directly coupled to CNBr-activated Sepharose. Sepharose-bound complexes were eluted into sample buffer containing 2% SDS and 1% 2-mercaptoethanol, separated in reducing 8% SDS-PAGE, and transferred to Immobilon-P sheet or nitrocellulose membrane, separated in reducing 8% SDS-PAGE, and transferred to Immobilon-P sheet or nitrocellulose membrane. Anti-fyn (UBI), anti-yes (20) (from T. Yamamoto and J. Sukegawa), and anti-lck (21) (from Y. Koga) antibodies were used for detection in Western blotting, as indicated. Filters were developed using a goat anti-rabbit or a sheet anti-mouse Ig antibody conjugated to HRP and ECL.

FIG. 3D. Same as FIGS. 3A–3C, except that filters were developed using $^{125}$I-labeled anti-$p56^{lck}$ mAb.

Figure 4A:
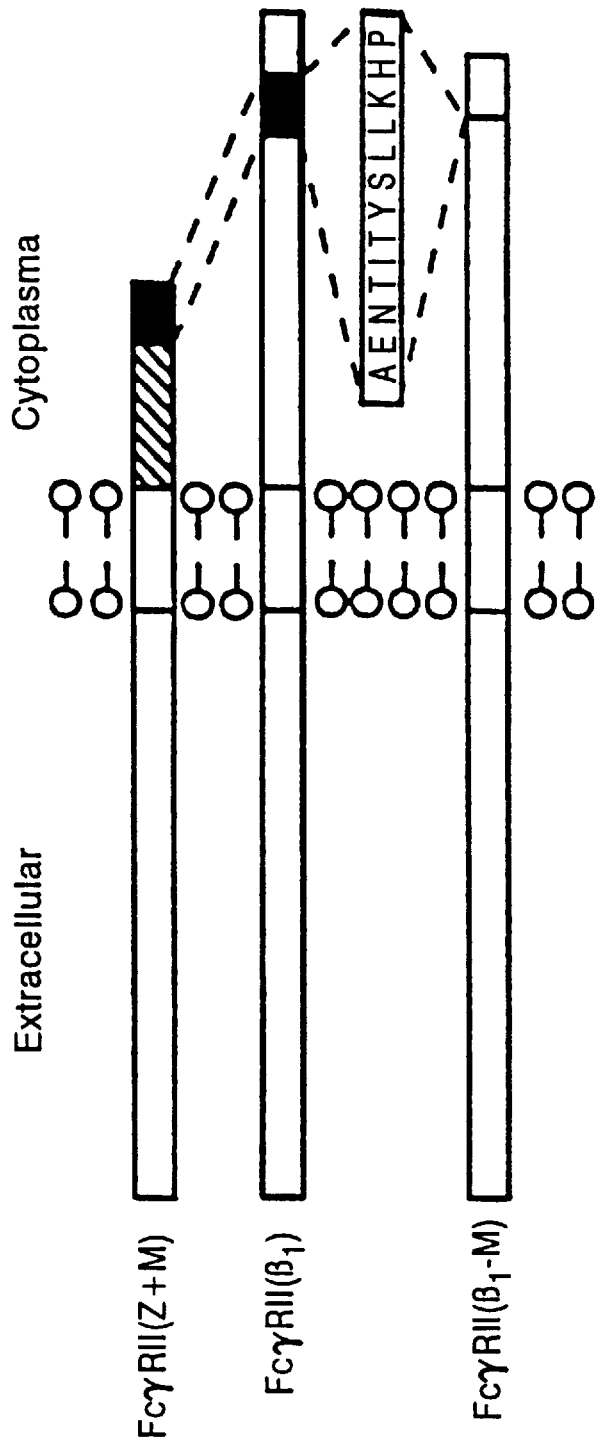

FIG. 4A. Schematic representation of mutant FcγRII.

Mutant murine FcγRII cDNAs were constructed by using polymerase chain reaction (PCR) methods. All constructs were confirmed by sequencing. Both FcγRII(Z+M) and FcγRII(β1-M) contain the extracellular and transmembrane domains of FcγRII(β1). The cytoplasmic domain of FcγRII (β1-M) has the internal deletion of 13 residues (amino acids 303–315 in β1 isoform of FcγRII), and that of FcγRII(Z+M) is composed of the first 18 and the following 13 residues from the cytoplasmic domain of human ζ chain of TCR/CD3 (amino acids 53–68 in human ζ and two additional ser; shown in hatched region) and FcγRII (AENTITYSLLKHP (SEQ ID NO:1)), respectively. These cDNAs were cloned together with the neomycin resistant gene into pCEXV-3.

Figure 4B:
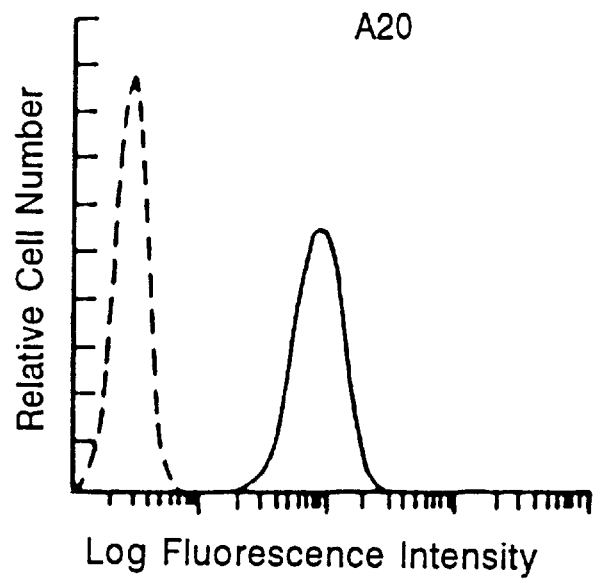

FIG. 4B. FACS analysis of A20.

Figure 4C:
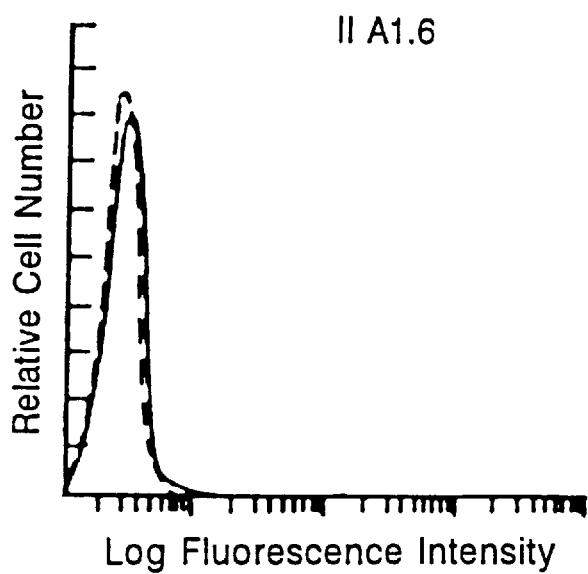

FIG. 4C. FACS analysis of IIA1.6.

Figure 4D:
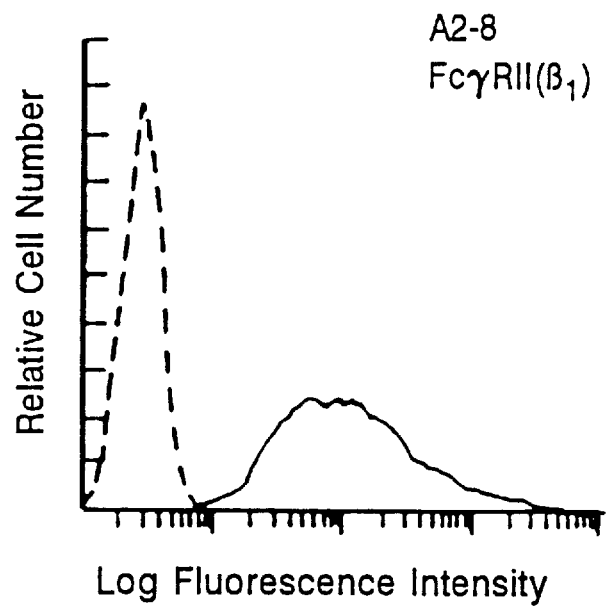

FIG. 4D. FACS analysis of A2-8 cells transfected with FcγRII($β_1$) cDNA. IIA1.6 cells were transfected by electrophoration and neo resistant clones were checked by FACS analysis using 2.4G2 mAb.

Figure 4E:
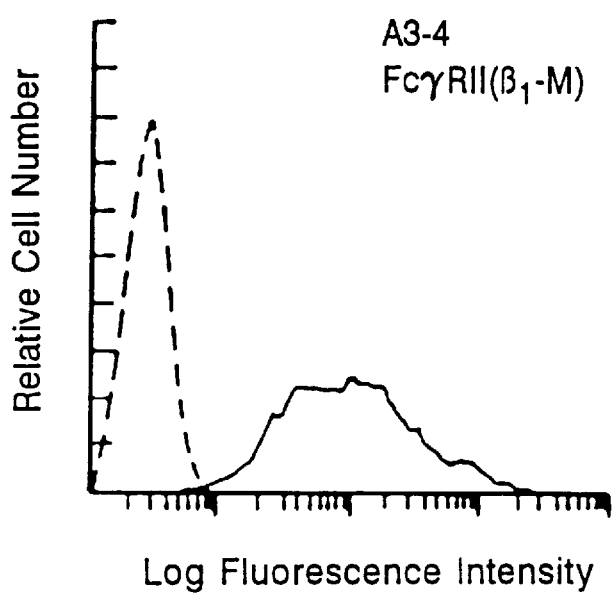

FIG. 4E. FACS analysis of A3-4 cells transfected with FcγRII($β_1$-M) cDNA.

Figure 4F:
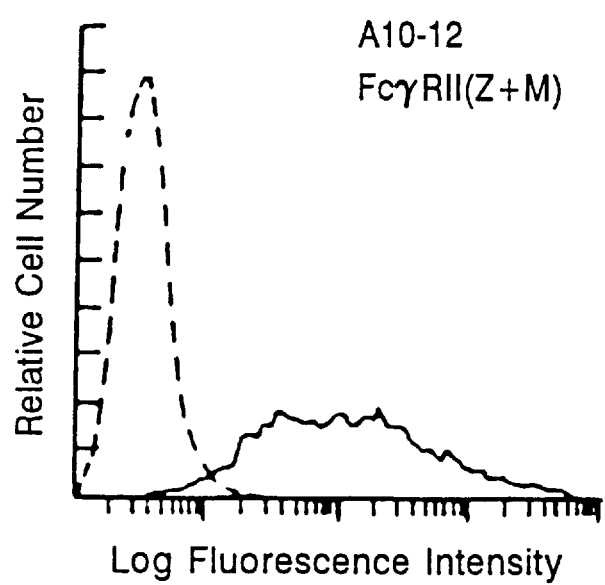

FIG. 4F. FACS analysis of A10-12 cells transfected with FcγRII(Z+M) cDNA.

FIGS. 5A–E. Calcium mobilization after cross-linking of mIg or co-crosslinking with FcγRII. $Ca^{2+}$ mobilization of non-transfected and transfected cells stimulated by whole and F(ab')$_2$ anti-mIg antibodies.

Cells were loaded with 3 mM fura-2 and stimulated with rabbit intact (80 mg/ml) and F(ab')$_2$ (50 mg/ml) anti-mIgG antibodies. The application times were indicated by bars. Intracellular $Ca^{2+}$ levels were recorded with fluorescence spectrophotometer (Hitachi F2000). In the presence of 2.4G2 (4 mg/ml), $Ca^{2+}$ mobilization patterns by intact antibodies were essentially the same as those by F(ab')$_2$.

FIG. 5A.

$Ca^{2+}$ mobilization of non-transfected A20 cells stimulated by whole and F(ab')$_2$ anti-mIg antibodies.

FIG. 5B.

$Ca^{2+}$ mobilization of non-transfected II A1.6 cells stimulated by whole and F(ab')$_2$ anti-mIg antibodies.

FIG. 5C.

$Ca^{2+}$ mobilization of A2-8 cells transfected with FcγRII ($β_1$) cells stimulated by whole and F(ab')$_2$ anti-mIg antibodies.

FIG. 5D.

$Ca^{2+}$ mobilization of A3-4 cells transfected with FcγRII ($β_1$-M) cells stimulated by whole and F(ab')$_2$ anti-mIg antibodies.

FIG. 5E.

Ca$^{2+}$ mobilization of A10-12 cells transfected with FcγRII (Z+M) cells stimulated by whole and F(ab')$_2$ anti-mIg antibodies.

FIGS. 5F–K. Calcium mobilization after cross-linking of mIg or co-crosslinking with FcγRII. The effect of EGTA on the Ca$^{2+}$ mobilization induced by whole and F(ab')$_2$ anti-mIg antibodies.

Cells were loaded with 3 mM fura-2 and stimulated with rabbit intact (80 mg/ml) and F(ab')$_2$ (50 mg/ml) anti-mIgG antibodies. The application times were indicated by bars. Intracellular Ca$^{2+}$ levels were recorded with fluorescence spectrophotometer (Hitachi F2000). In the presence of 2.4G2 (4. mg/ml), Ca$^{2+}$ mobilization patterns by intact antibodies were essentially the same as those by F(ab')$_2$. For chelation of extracellular Ca$^{2+}$, EGTA (1 mM) was added 1. min before the ligand stimulation.

FIG. 5F.

Effect of EGTA on Ca$^{2+}$ mobilization in A20 cells induced by F(ab')$_2$ anti-mIg antibodies.

FIG. 5G.

Effect of EGTA on Ca$^{2+}$ mobilization in A20 cells induced by whole anti-mIg antibodies.

FIG. 5H.

Effect of EGTA on Ca$^{2+}$ mobilization in A3-4 cells transfected with FcγRII($\beta_1$-M) induced by F(ab')$_2$ anti-mIg antibodies.

FIG. 5I.

Effect of EGTA on Ca$^{2+}$ mobilization in A3-4 cells induced by whole anti-mIg antibodies.

FIG. 5J.

Effect of EGTA on Ca$^{2+}$ mobilization in A10-12 cells transfected with FcγRII(Z+M) induced by F(ab')$_2$ anti-mIg antibodies.

FIG. 5K.

Effect of EGTA on Ca$^{2+}$ mobilization in A10-12 cells induced by whole anti-mIg antibodies.

Figure 6A:
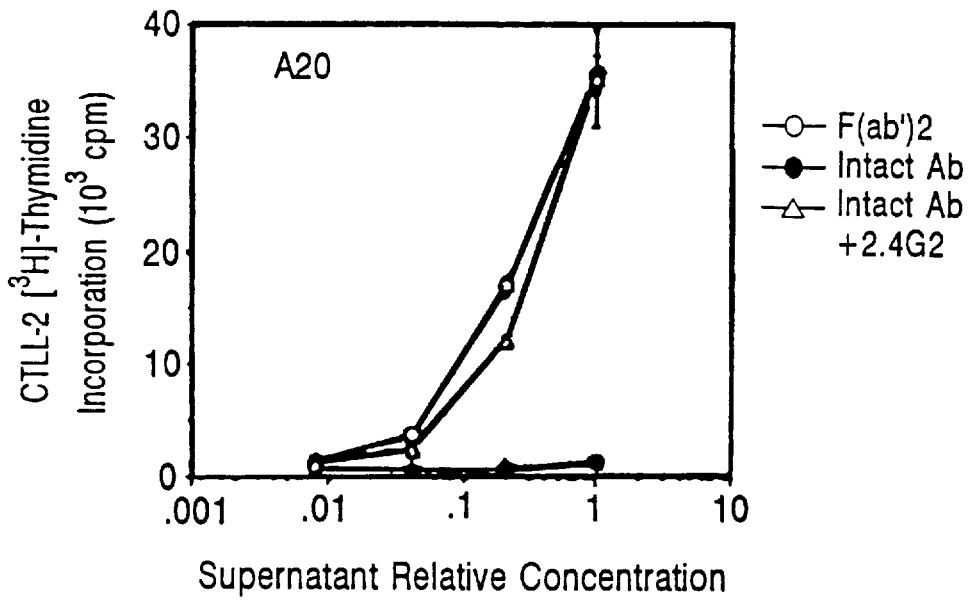

FIG. 6A. IL-2 secretion after crosslinking of mIg or co-crosslinking with FcγRII.

IL-2. secretion of non-transfected and transfected cells by whole and F(ab')$_2$ anti-mIgG antibodies.

A20 cells (5×10$^5$/ml) were stimulated by the indicated antibodies (10 mg/ml intact, 5 mg/ml F(ab)$_2$, and 10 mg/ml 2.4G2 antibodies) for 18 hr at 37° C. IL-2 activity in serial dilutions of the culture supernatant was measured by [$^3$H]-thymidine incorporation using IL-2 dependent cell line, CTLL-2 as described. The experiments were performed three times. The mean and SEM of triplicate points are shown.

Figure 6B:
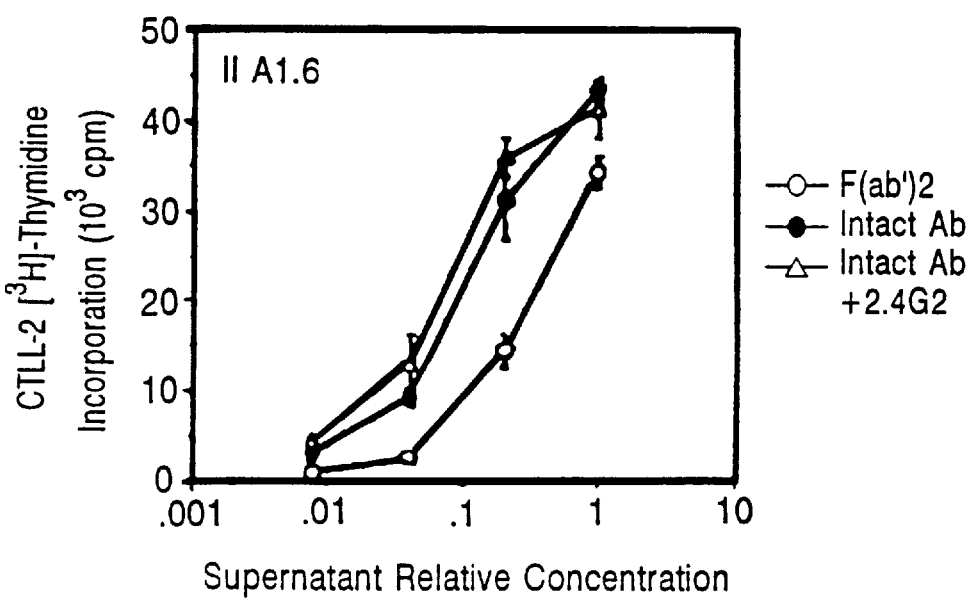

FIG. 6B. Same as FIG. 6A for II A1.6 cells.

Figure 6C:
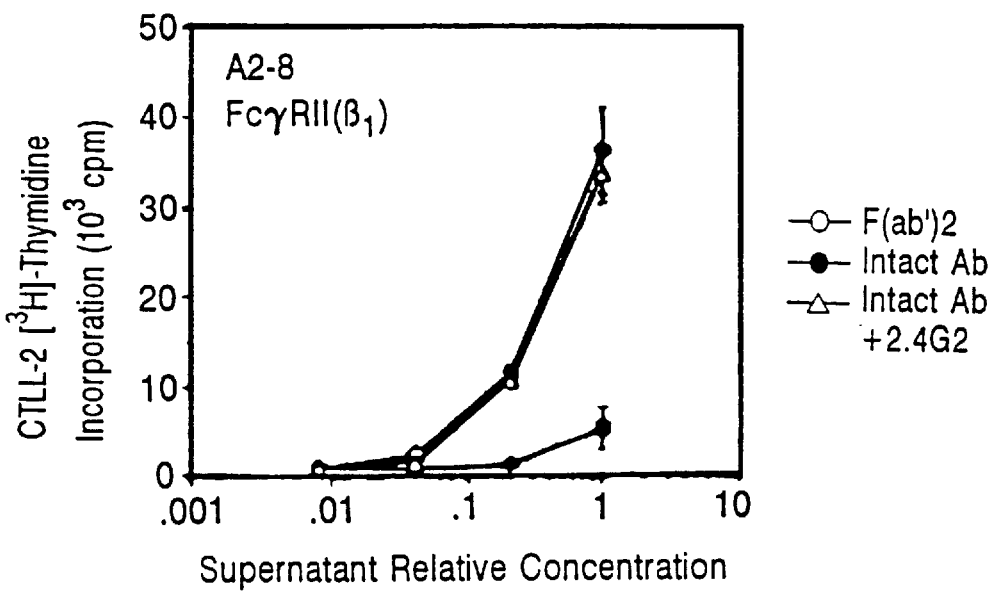

FIG. 6C. Same as FIG. 6A for A2-8 cells transformed with FcγRII($\beta_1$).

Figure 6D:
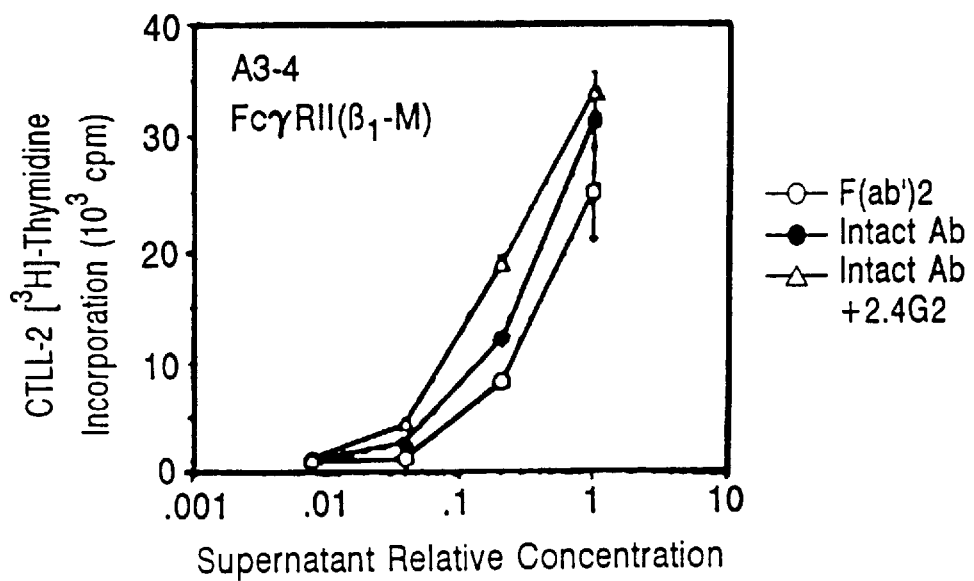

FIG. 6D. Same as FIG. 6A for A3-4 cells transformed with FcγRII($\beta_{1-M}$).

Figure 6E:
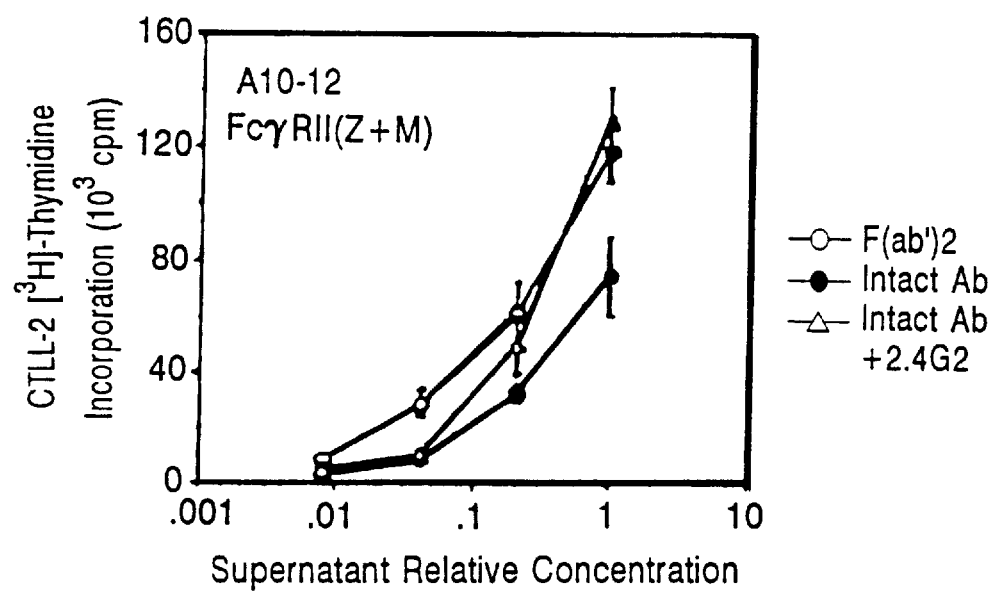

FIG. 6E. Same as FIG. 6A for A10-12 cells transformed with FcγRII(Z+M).

Figure 7A:
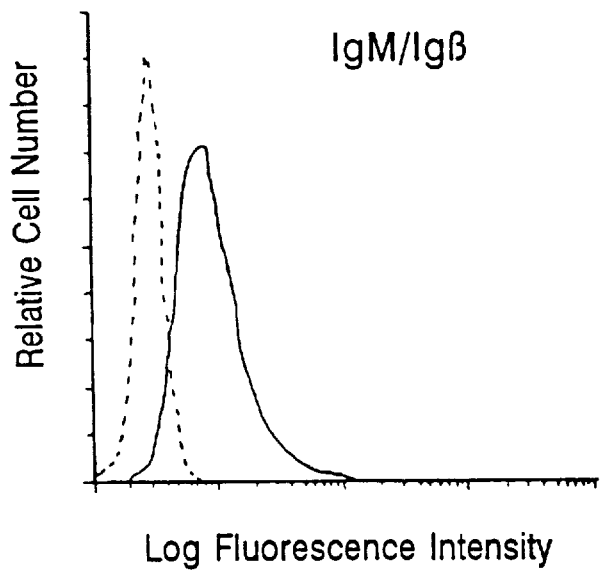

FIG. 7A. Cell surface expression of IgM/Ig-β on A20 cells.

Figure 7B:
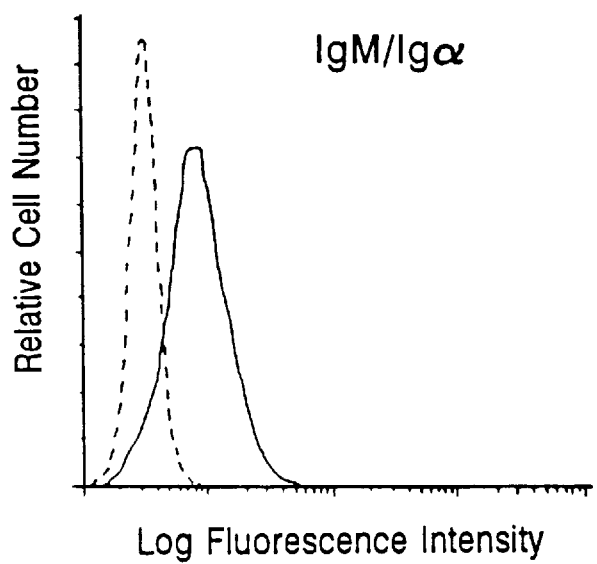

FIG. 7B. Cell surface expression of IgM/Ig-β on A20 cells. Chimeric IgM/Ig-α cDNA is composed of human K and β-chimeric chains against phosphorylcholine. The extracellular, transmembrane and cytoplasmic domains of the chimeric μ chain are derived from wild-type μ chain, mutated transmembrane μ chain (replacement of both tyrosine 587, and serine 588 with valine) and murine cytoplasmic Ig-α (amino acids 160–220), respectively. IgM/Ig-β is the same as IgM/Ig-α except that the cytoplasmic domain is composed of amino acids 181–228 murine Ig-β. These cDNAs were cloned into pfNeo vector. DNAs were transfected into A20 cells by electrophoresion, and resistant clones were checked by FACS analysis using rabbit anti-hIgM antibody.

Figure 7C:
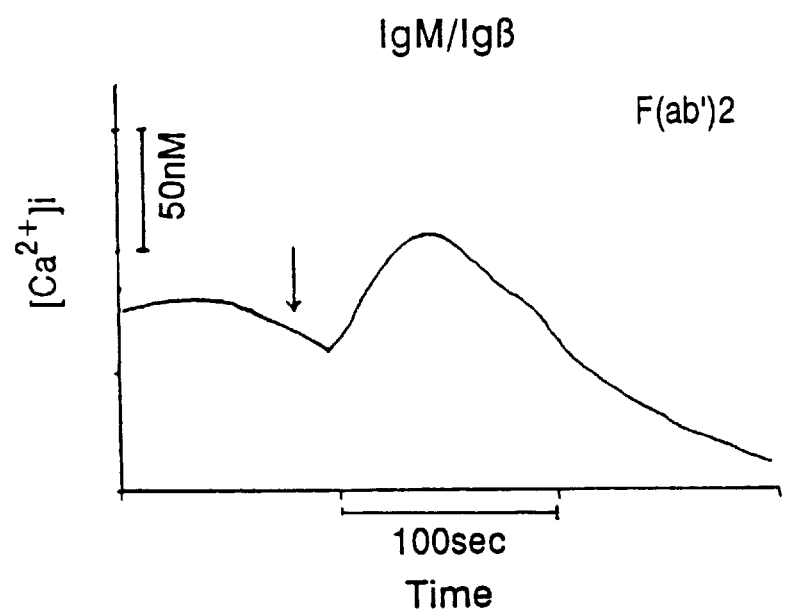

FIG. 7C. Ca$^{2+}$ mobilization stimulated through rabbit F(ab')$_2$ (50 mg/ml) fragment of chimeric anti-hIgM molecule IgM/Igβ by FcγRII. For description of Ca$^{2+}$ mobilization, see FIG. 5.

Figure 7D:
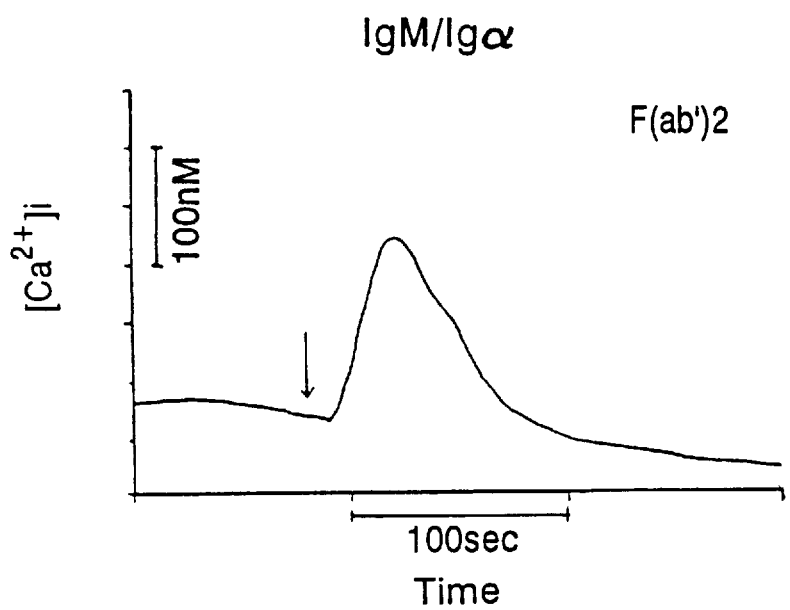

FIG. 7D. Ca$^{2+}$ mobilization stimulated through F(ab')$_2$ fragment of chimeric molecule IgM/Igα by FcγRII.

Figure 7E:
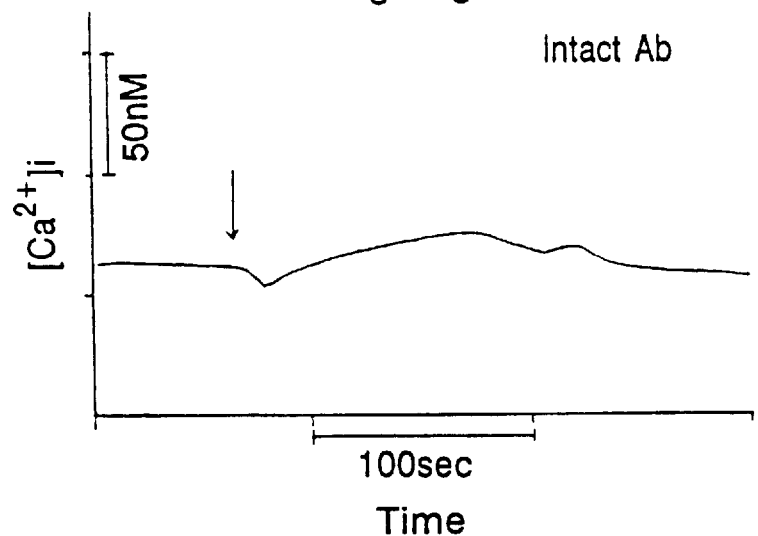

FIG. 7E. Ca$^{2+}$ mobilization stimulated through intact IgM/Igβ (80 mg/ml) by FcγRII.

Figure 7F:
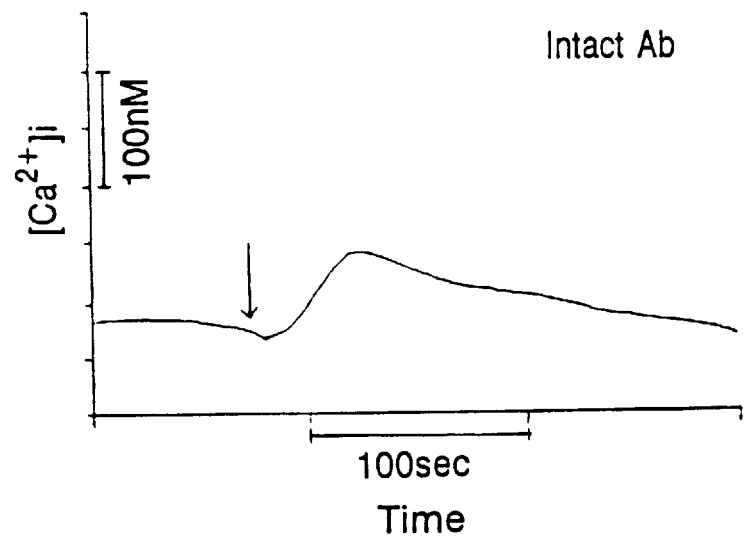

FIG. 7F. Ca$^{2+}$ mobilization stimulated through intact IgM/Igα by FcγRII.

Figure 7G:
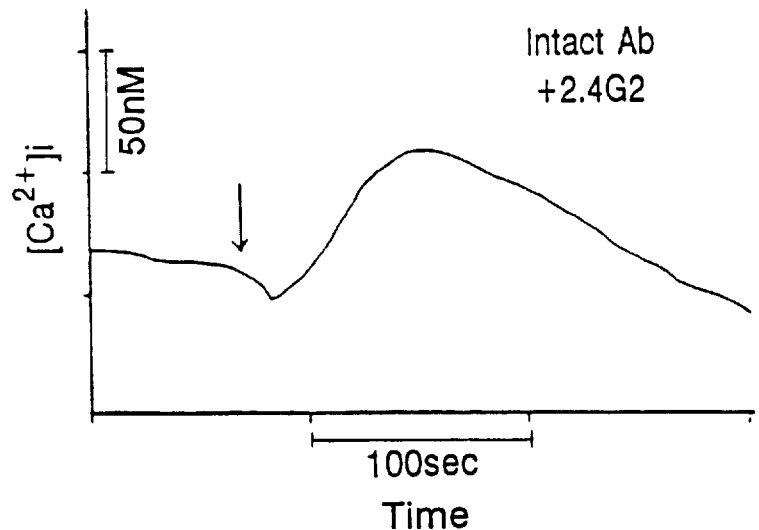

FIG. 7G. Ca$^{2+}$ mobilization stimulated through intact IgM/Igβ+2.4G2 by FcγRII. Cells were preincubated with 2.4G2 (5 mg/ml) for 5 min before application of intact antibody.

Figure 7H:
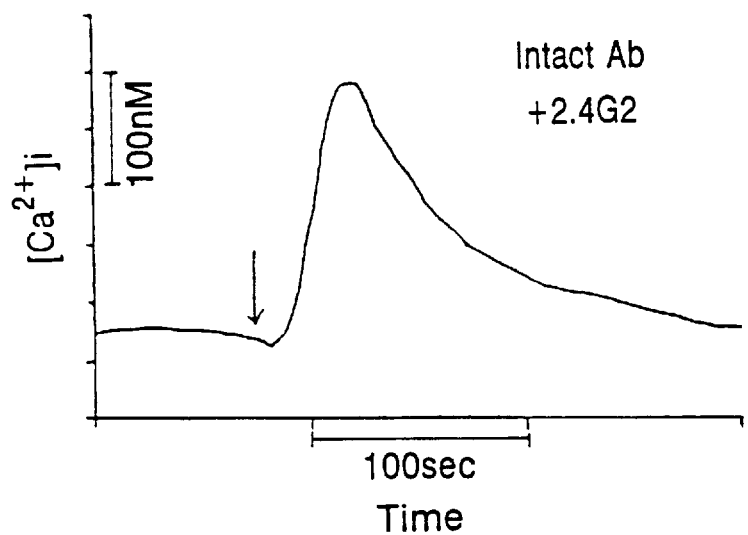

FIG. 7H. Ca$^{2+}$ mobilization stimulated through intact IgM/Igα+2.4G2 by FcγRII. Cells were preincubated with 2.4G2 (5 mg/ml) for 5 min before application of intact antibody.

Third Series of Experiments

Figure 8A:
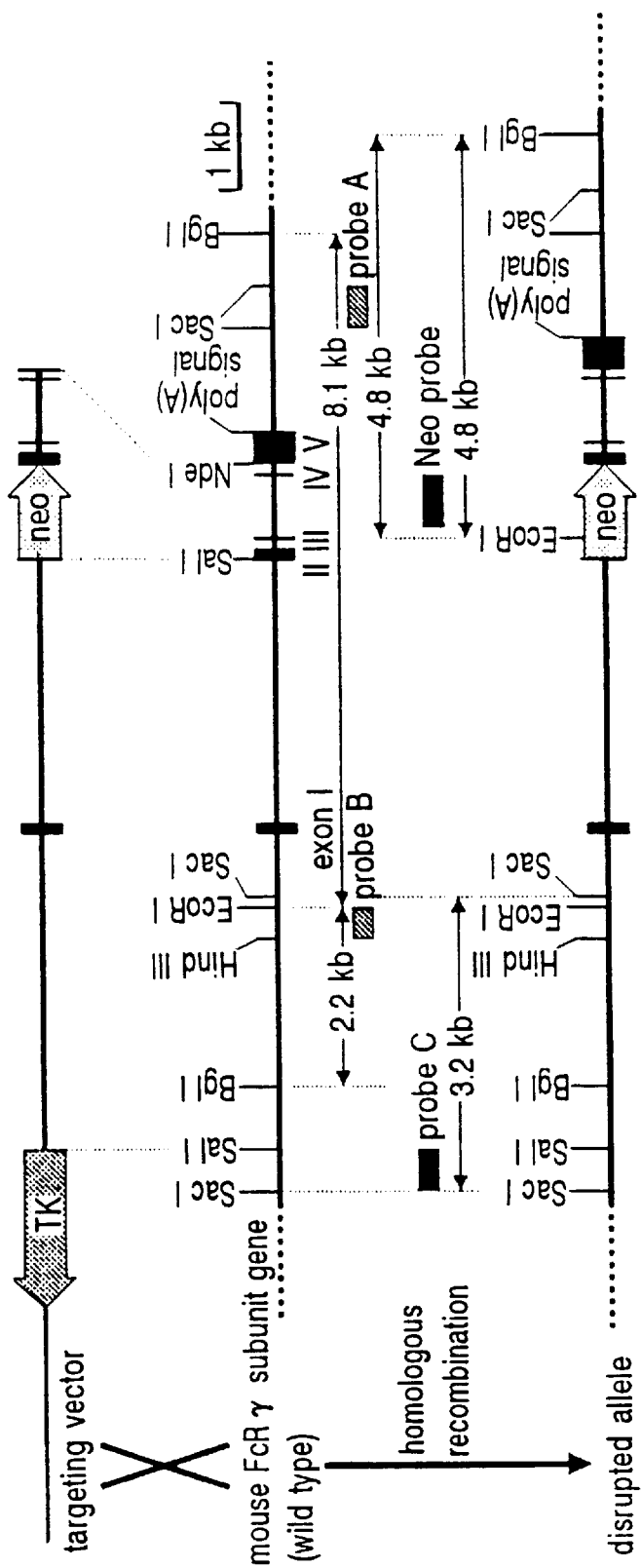
Figure 8B:
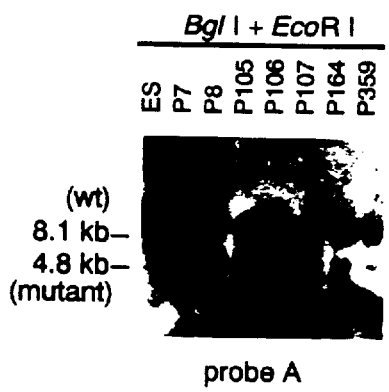
Figure 8C:
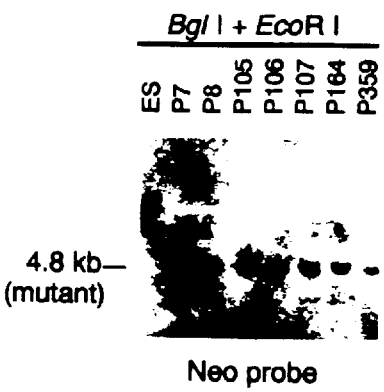
Figure 8D:
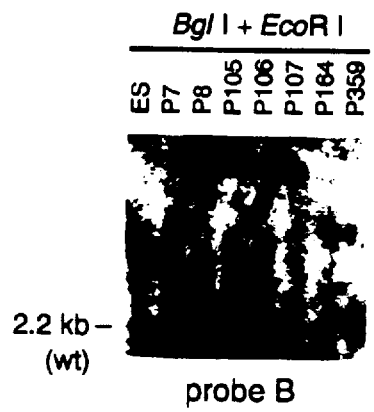
Figure 8E:
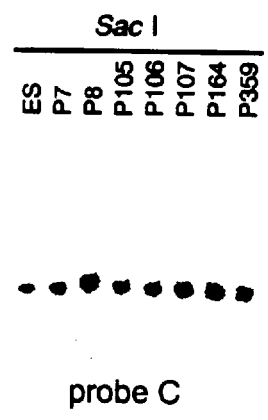

FIG. 8A. Design of the Targeting Vector.

The γ subunit locus (wild type allele), the targeting vector, and expected targeted allele are shown. The positions of the 3'-flanking probe (probe A), the internal probe (probe B), the 5'-flanking probe (probe C) and the neo probe are indicated.

FIGS. 8B–8E. Southern Blot Analysis of DNA from Targeted ES Cell Clones.

Southern blot analysis of targeted ES clones. DNA from seven clones (p7-P359) were analyzed using probes A,B,C and neo. Probe A detects a 8.1 kb BglI-EcoRI fragment from the wild type allele, whereas it detects a 4.8 kb band derived from the targetted allele, since the neomycin resistance gene introduced a new EcoRI site. The neo probe detects only a 4.8 kb fragment while probes B and C detect 2.2 and 3.2 kb fragments, respectively, derived from wild-type and target-ted alleles.

Figure 8F:
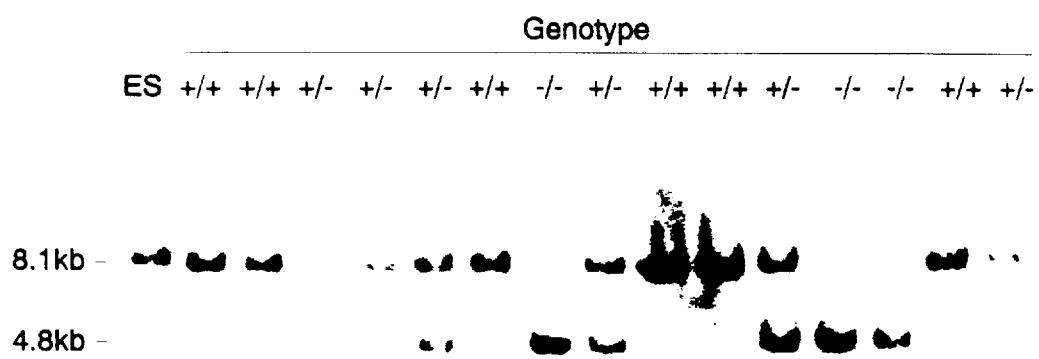

FIG. 8F. Southern blot analysis of genomic DNA from heterozygous intercrosses.

Genomic DNA was isolated from the litters of 15 mice from heterozygous intercrosses. DNA was digested with BglI and EcoRI, electrophoresed, and blotted with a 0.42 kb SalI-EcoRI fragment from the γ subunit cDNA. Fragments obtained from wild-type (8.1 kb) and targeted (4.8 kb) alleles are indicated. Lane 1 represents a digest of the wild-type ES cell genomic DNA.

Figures 9A, 9B:
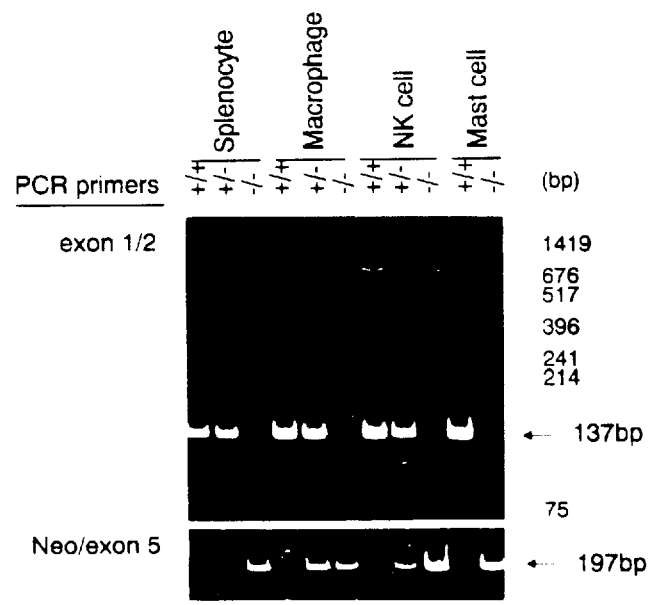

FIGS. 9A and 9B. Characterization of γ chain mRNA from FcRγ$^{n1}$.

Total RNA was isolated from activated macrophages, mast cells and NK cells and subjected to RT-PCR analysis as described in Experimental Procedures. The possible structure of a γ subunit-neomycin fusion transcript is depicted at the bottom, in which the distances between exons are indicated. PCR primers, indicated as short arrows, were used to amplify a fragment upstream or downstream from the insertion site of MC1-neo cassette. Amplified PCR products were electrophoresed on a 7.5% polyacrylamide gel. The sizes of amplified fragments are indicated in base pairs on right of each panel. +/+, wild type; +/–, heterozygote; –/– homozygote.

Figure 9C:
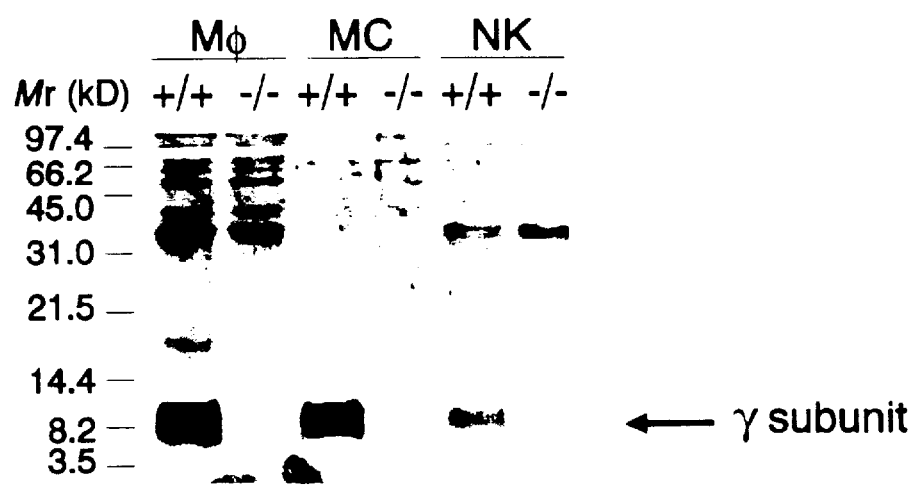

FIG. 9C. Characterization of γ chain protein from FcRγ$^{n1}$.

Western Analysis of γ Subunit Expression

Cell suspensions were prepared from activated macrophages (Mφ), mast cells (MC) and NK cells, and subjected to Western analysis. A 6–9 kD γ subunit polypeptide is detected in cells derived from wild-type and heterozygous mice, but is absent in the homozygous mutant mice which produce no detectable γ subunit.

FIGS. 10A–10C. Flow Cytometric Analysis of Fc Receptor Expression on Effector Cells.

FcγRII and III expression on thioglycollate-elicited peritoneal macrophages. Macrophages were stained with 2.4G2 and the macrophage marker Mac-1; 2.4G2 recognizes both FcγRII and III. Homozygous mutant mice have a 80% reduction in 2.4G2 staining (bold tracing).

FIGS. 10D–10F. Flow Cytometric Analysis of Fc Receptor Expression on Effector Cells.

FcγRII and III expression on bone marrow neutrophils. Neutrophils were obtained from the bone marrow and stained with 2.4G2 and the granulocyte specific marker, Gr-1. 2.4G2 staining is reduced by 50% in the homozygous mutant mice (bold tracing).

FIG. 10G–10I. Flow Cytometric Analysis of Fc Receptor Expression on Effector Cells. FcγRIII expression on IL-2-induced splenic NK cells. NK cells were prepared as described in Experimental Procedures and stained with 2.4G2 and the NK cell marker 4D11. 4D11 is expressed on 50% of NK cells in both wild-type and mutant mice, while 2.4G2 staining is undetectable in mutant mice (bold tracing).

FIG. 10J–10L. Flow Cytometric Analysis of Fc Receptor Expression on Effector Cells.

FcεRI expression on bone marrow derived mast cells. Cells were stained with FITC-IgE and the mast cell marker Ack 2. IgE staining is lost in the mutant mice (bold tracing), which retain Ack 2 staining. Identical results were obtained using mast cells purified from peritoneal lavage cells by Ficoll gradient centrifugation (not shown). Shaded regions correspond to control antibody staining; bold tracing indicated −/− staining, while light tracing corresponds to +/+ staining of the x-axis antibody.

Figure 11A:
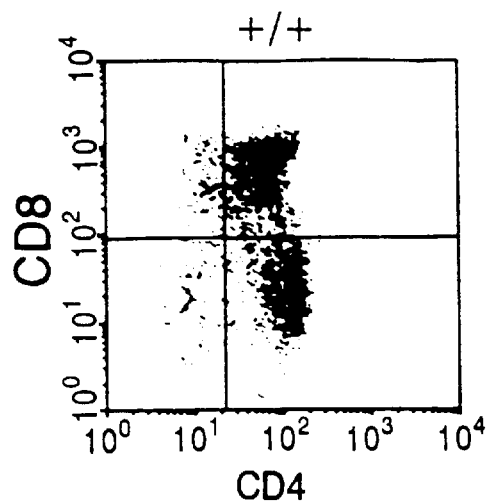
Figure 11B:
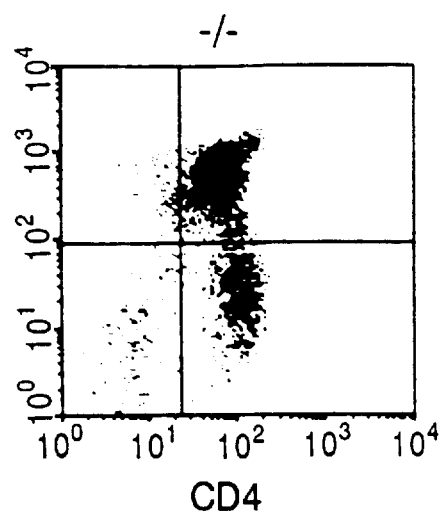

FIGS. 11A–11B. Flow Cytometric Analysis of Lymphocyte Populations in FcRγ$^{n1}$ mice.

Expression of CD4+CD8/CD3 populations in the thymus of wild-type and mutant mice. Thymocytes or splenic T cells from either 2 week old (not shown) or 10 week old mice were stained with mAbs to CD4, CD8 and TCR chains. No differences are apparent in these populations in mutant mice, when compared to wild-type.

Figure 11C:
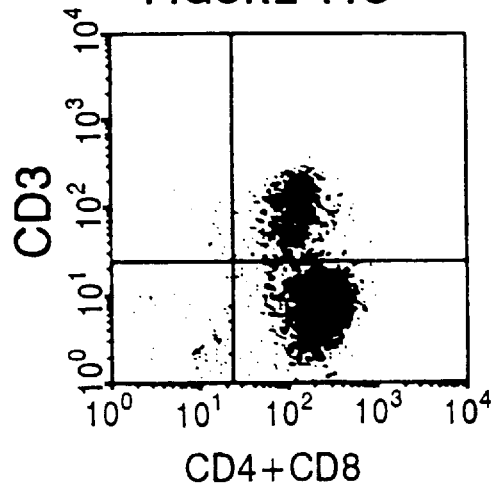
Figure 11D:
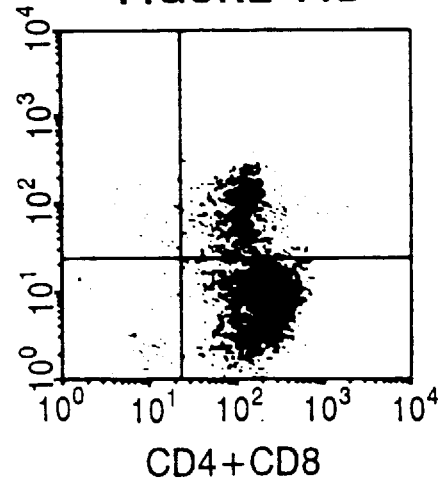

FIGS. 11C and 11D. Expression of CD4+CD8/CD3 populations in the thymus of wild-type and mutant mice. See description of FIG. 4A.

FIGS. 11E and 11F. Expression of TCR αβ in splenic T cells of mutant and wild-type mice.

FIGS. 11G and 11H.

Expression of FcγRII in splenic B cells of mutant and wild-type mice. The double negative population represent splenic T cells not stained by B220 or 2.4G2.

FIGS. 12A–H. Rosetting and Phagocytosis of IgG-opsonized Red Blood Cells by Activated Macrophages SRBCs were TNP-derivatized and coated with anti-TNP IgG1 or directly coated with anti-SRBC IgG2a. Rosetting was performed at 4° C. for 30 minutes; phagocytosis at 37° C. for 90 minutes. Unbound cells were removed by washing; non-internalized cells were lysed with distilled water. IgG1 binding is through FcγRII/III while IgG2a binding is through FcγRI. Mutant macrophages are non-phagocytic, while retaining IgG1 binding ability through FcγRII; binding of IgG2a through FcγRI is dramatically reduced. IgG2a binding was performed in the presence of 2.4G2 to control for FcγRII/III binding to this subclass.

FIG. 12A.
Rosetting of IgG1 opsonized SRBCs by +/+.
FIG. 12B.
Phagocytosis of IgG1 opsonized SRBCs by +/+.
FIG. 12C.
Rosetting of IgG1 opsonized SRBCs by −/−.
FIG. 12D.
Phagocytosis of IgG1 opsonized SRBCs by −/−.
FIG. 12E.
Rosetting of IgG2a opsonized SRBCs by +/+.
FIG. 12F.
Phagocytosis of IgG2a opsonized SRBCs by +/+.
FIG. 12G.
Rosetting of IgG2a opsonized SRBCs by −/−.
FIG. 12E.
Phagocytosis of IgG2a opsonized SRBCs by −/−.
FIG. 13A. Natural Killing Activities of Splenic NK Cells from Wild-Type and FcRγ$^{n1}$ mice Splenic NK cells generated after in vitro culture in the presence of exogenous IL-2 were tested for lytic activity against a set of targets including the NK-sensitive target YAC-1, the thymoma EL-4, and the TNP-derivatized EL-4.

Figure 13B:
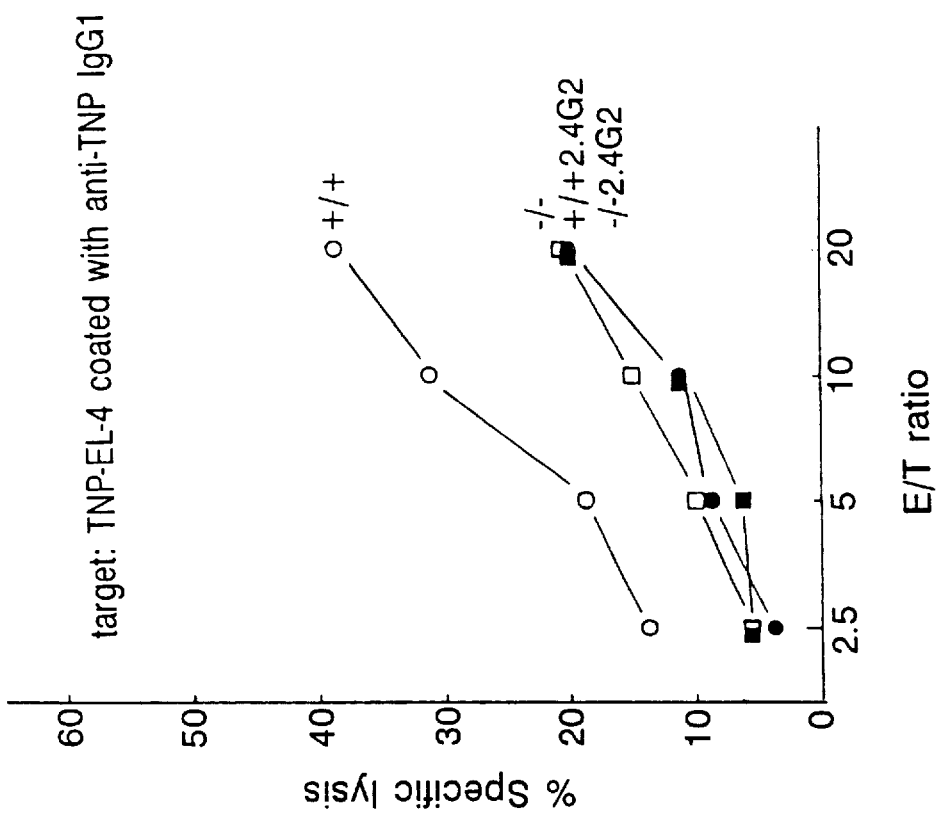
Figure 13A:
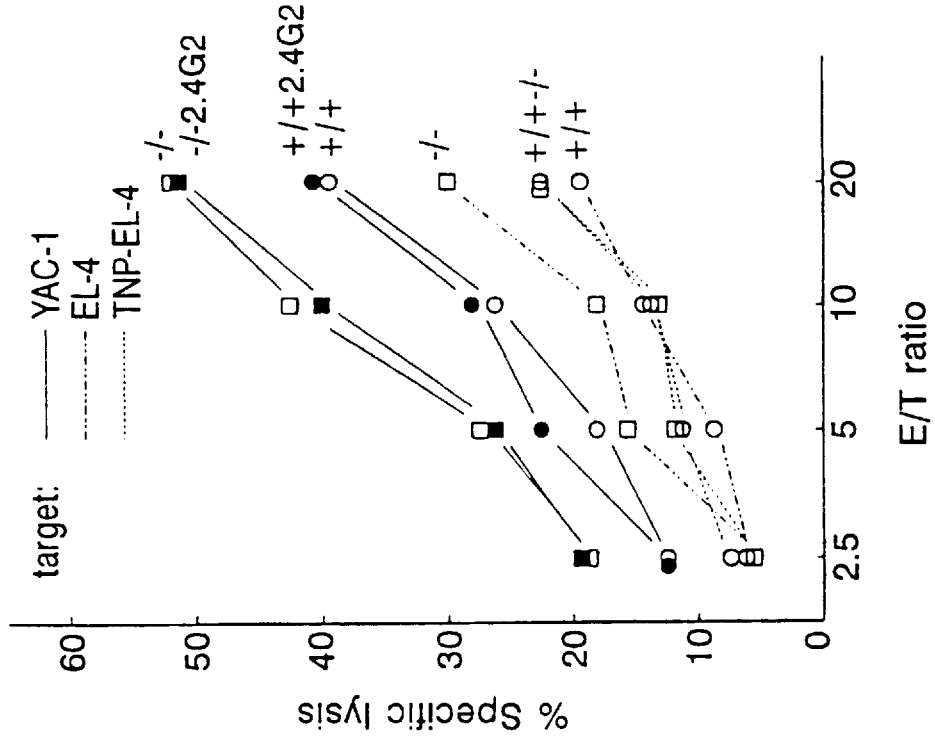

FIG. 13B. ADCC Activities of Splenic NK Cells from Wild-Type and FcRγ$^{n1}$ mice ADCC activities were tested on the following targets: TNP-derivatized EL-4 cells coated with an anti-TNP IgG1 antibody or TNP-derivatized, anti-TNP-coated EL-4 cells in the presence of the anti-FcγRII/III antibody 2.4G2.

Figure 14A:
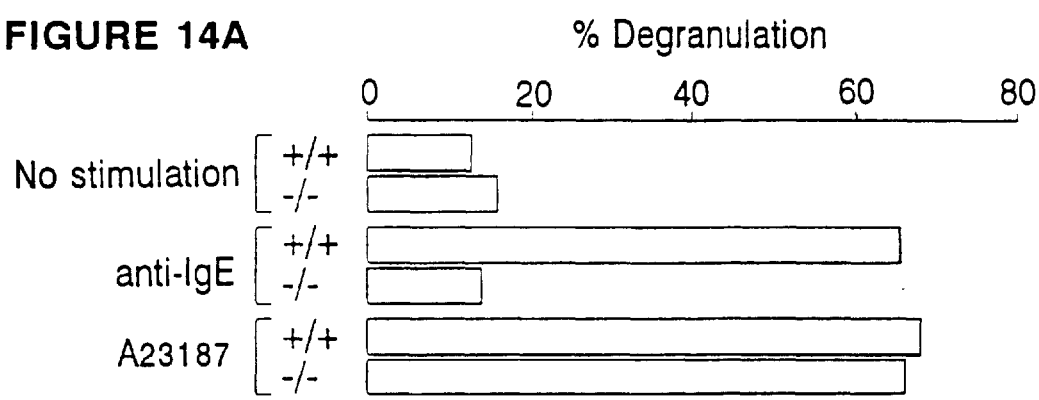

FIG. 14A. Functional Characterization of Mast cells from Wild-Type and FcRγ$^{n1}$ mice: Mast cell degranulation.

Bone marrow-derived mast cells were pre-sensitized with monoclonal murine IgE and subsequently degranulated by crosslinking with murine anti-IgE antibody. Maximal degranulation was determined using ionophore A23187.

Figure 14B:
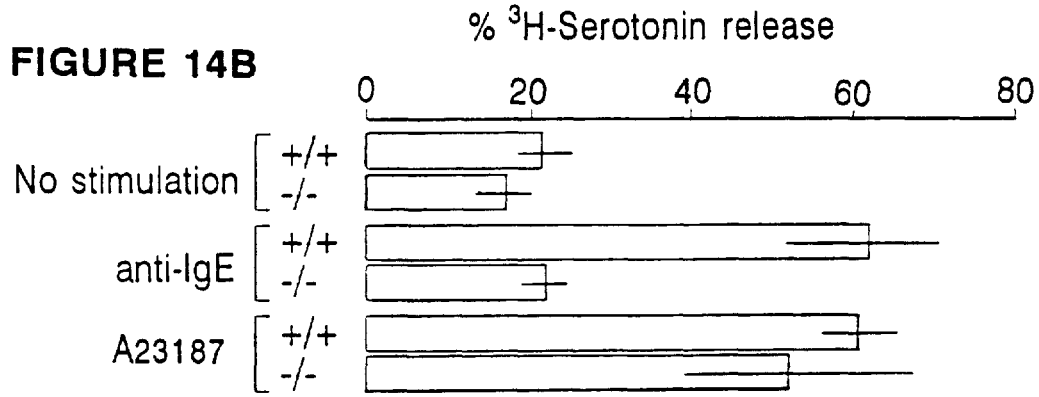

FIG. 14B. Functional Characterization of Mast cells from Wild-Type and FcRγ$^{n1}$ mice: Mast cell serotonin release.

Bone marrow-derived mast cells were preincubated with $^3$H-serotonin and then incubated with monoclonal murine IgE. $^3$H-serotonin released into the supernatant was quantitated after exposure to monoclonal anti-IgE or to ionophore A23187.

Figure 14C:

FIG. 14C. Functional Characterization of Mast cells from Wild-Type and FcRγ$^{n1}$ mice: RT-PCR analysis of IL-4 mRNA after crosslinking of IgE on mast cells.

Mast cells were prepared and sensitized as above and cells were collected and subjected to RT-PCR analysis for IL-4 mRNA as described in Experimental Procedures.

FIG. 14D. Functional Characterization of Mast cells from Wild-Type and FcRγ$^{n1}$ mice: Prostaglandin D$_2$ release from mast cells after crosslinking of IgE.

Bone marrow-derived mast cells were sensitized overnight with mouse monoclonal IgE. The cells were stimulated as above and culture supernatants were collected at various time intervals. Amount of prostaglandin D$_2$ released in the supernatant was determined by radioimmunoassay.

Fourth Series of Experiments

FIGS. 15A–15D The Arthus reaction at 8 hours in +/+ (FIGS. 15A–15B) vs. −/− (FIGS. 15C–15D) mice, histologic sections of skin stained with hematoxylin and eosin. FIGS. 15A–15C ("Control") injected intradermally with either normal saline/preimmune rabbit IgG prior to intravenous injection of 20 mg/kg ovalbumin, FIGS. 15B and 15D injected with 100 μg rabbit anti-ovalbumin IgG. Magnification of small vessel with marginating neutrophils is shown in inset.

FIGS. 16A and 16B

Edema from 2 hour Arthus reaction. FIG. 16A, µl edema in +/+ vs. –/– mice in typical 2 hour experiment, quantitated after IV injection of $10^6$ cpm $^{125}$I human serum albumin by direct measurement of cpm $^{125}$I in rabbit anti-ovalbumin (30 µg) injected skin, with negative control area subtracted out; results are representative of at least 30 skin samples. FIG. 16B shows Evans Blue extravasation in +/+ (top) vs. –/– (bottom) after inclusion of 2% Evans Blue in intravenous injectate. Upper left quadrant in each skin section injected with buffer alone, Rbα-OVA injected in other three quadrants. The horizontal bar represents the mean value.

Figure 17A:
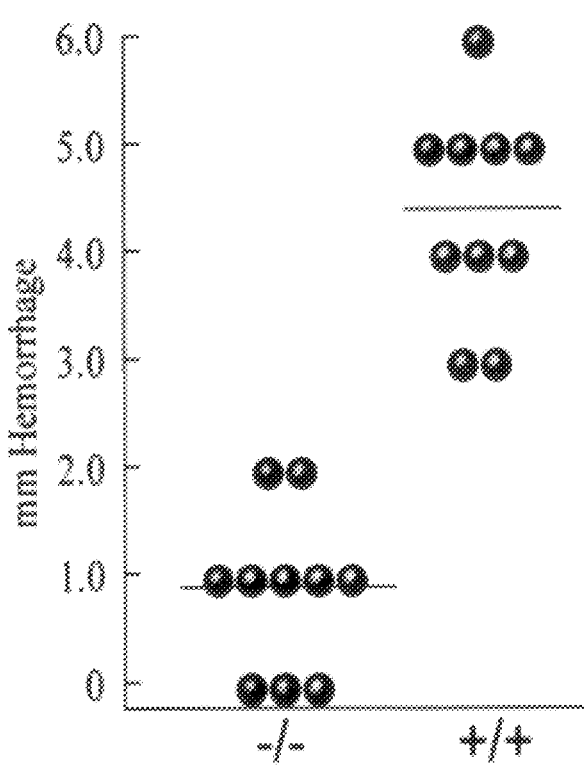
Figure 17B:
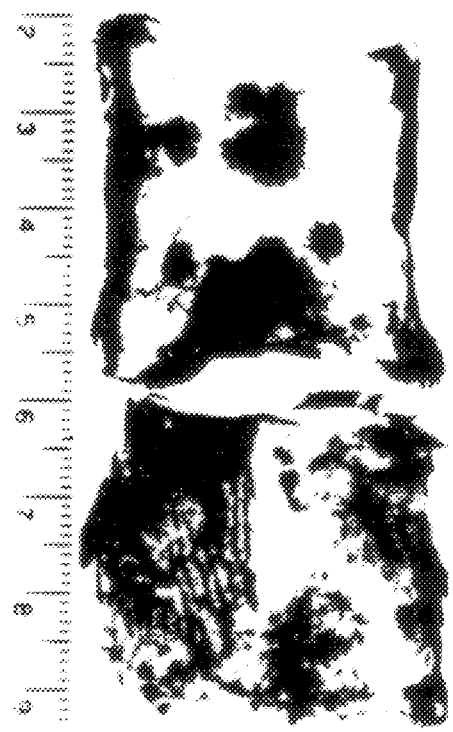

FIGS. 17A and 17B

Hemorrhage from 8 hour Arthus reaction. FIG. 17A, measurement of purpuric spots in representative 8 hour experiment using 30 kg antibody; FIG. 17B, photograph of inverted skin samples with +/+ at top and –/– at bottom. Negative control injections are in upper right, Rbα-OVA at other three sites.

FIG. 18

Myeloperoxidase from 8 hour Arthus reaction as measure of neutrophil infiltration. Myeloperoxidase was calorimetrically quantitated as previously described (12); experiment is representative of results from at least 20 skin samples in each group.

Figures 19A, 19B:

FIGS. 19A and 19B

Arthus reaction using mouse IgG2a. 100 µg affinity-purified monoclonal mouse IgG2a against TNP was injected ID and 20mg/kg DNP-coupled human serum albumin injected IV; animals were sacrificed at 8 hours. Skin samples were fixed in 10% buffered formalin and stained with hematoxylin and eosin.

Figure 20A:
Figure 20B:

FIGS. 20A and 20B Arthus reaction in –/– mice using IgG3 and zymosan. At left, 30 µg affinity purified monoclonal mouse IgG3 against TNP injected ID, with 20 mg/kg DNP-human serum albumin IV, animals were sacrificed at 8 hours post injection. At right, section of skin obtained 4 hours after ID injection of 250 kg zymosan.

FIGS. 21A and 21B Arthus reaction in complement depleted mice. Mice were injected three times intraperitoneally with 100 U/kg cobra venom factor at 8 hour intervals prior to performance of standard Arthus reaction. Representative sections taken at 8 hours from +/+ (left) and –/– (right) mice.

FIG. 22

The Fc receptor and the Arthus reaction. This model, delineated by solid arrows, proposes that immune complexes bind to Fc receptors on the effector cell, which then becomes activated to release mediators that ultimately result in the primary manifestations of the Arthus reaction. The pathway of the classical model of immune complex-mediated inflammation, by which complement binds directly to immune complexes causing its activation, is shown in dotted lines at left.

Figure 23:
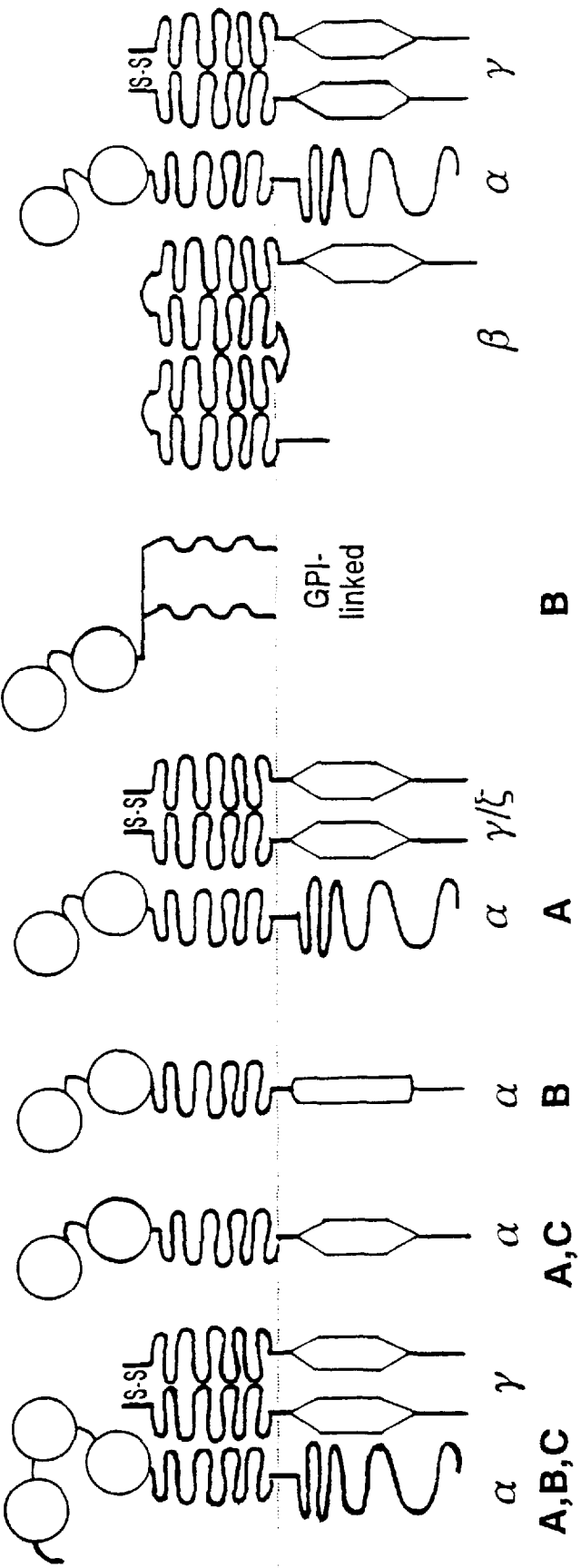
Figure 24A:
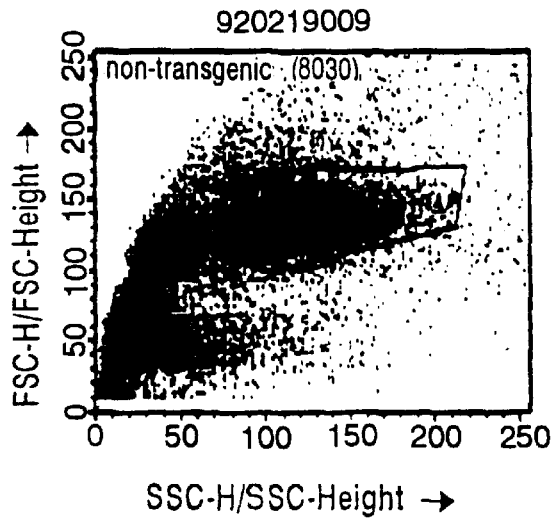
Figure 24B:
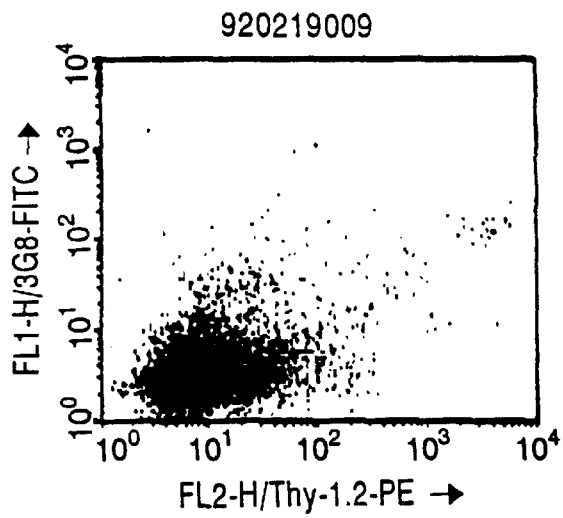
Figure 24C:
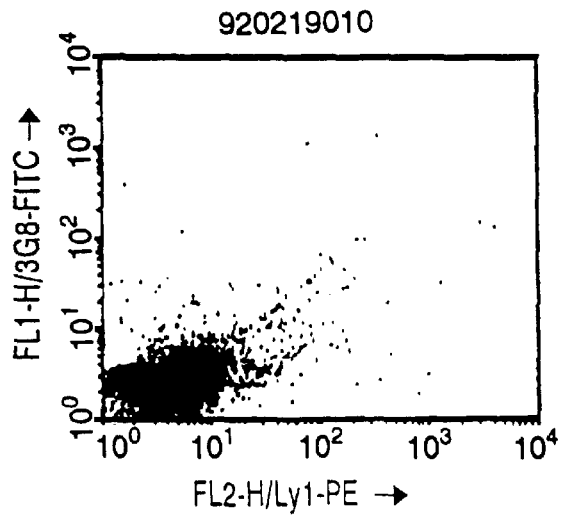
Figure 24D:
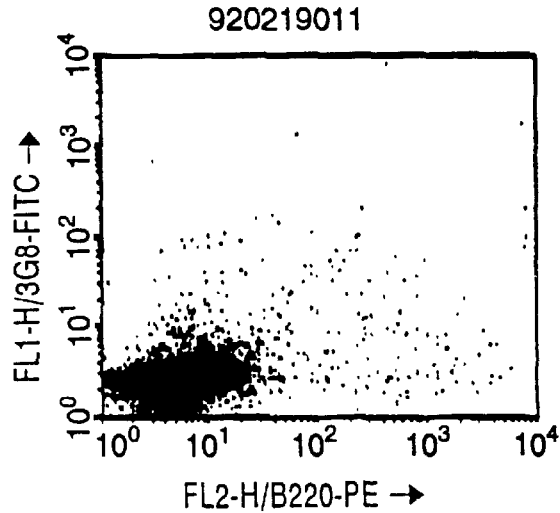
Figure 24E:
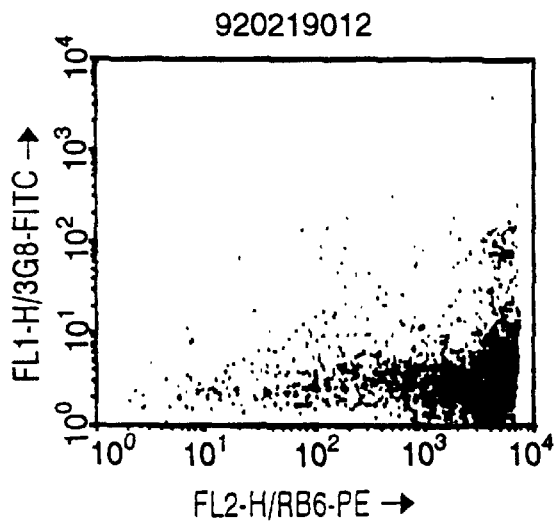
Figure 24F:
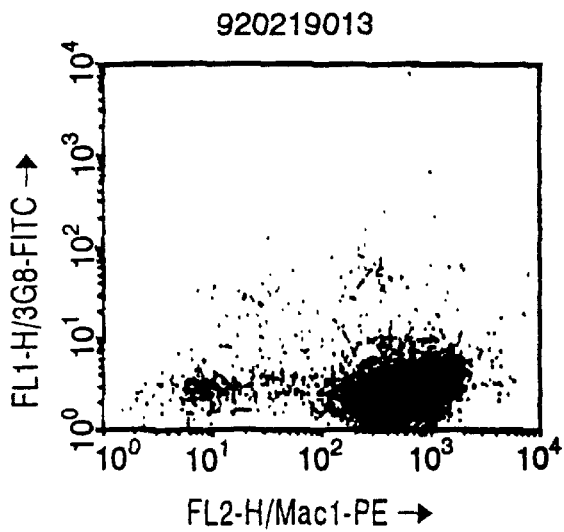
Figure 25A:
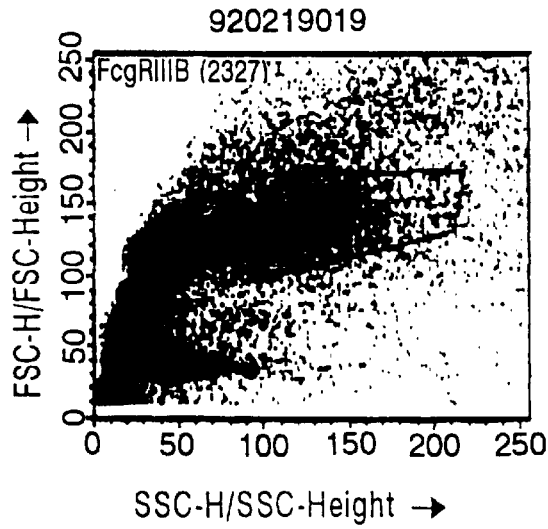
Figure 25B:
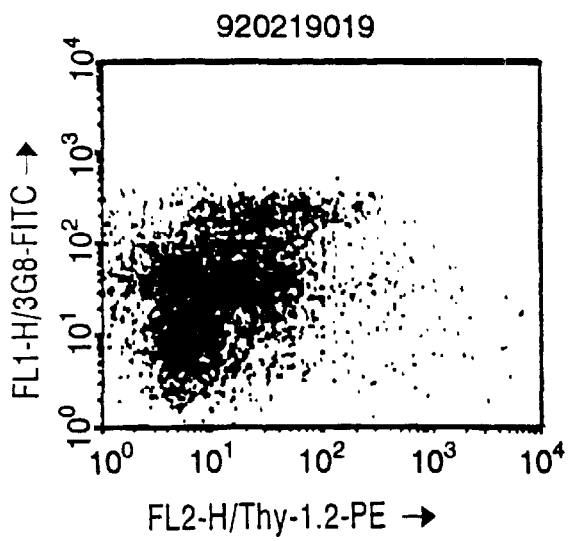
Figure 25C:
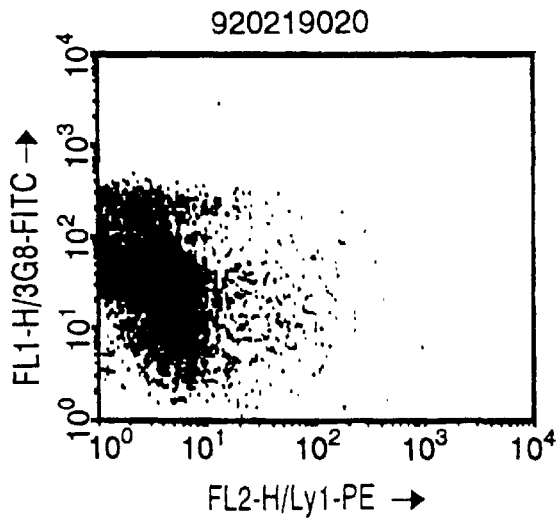
Figure 25D:
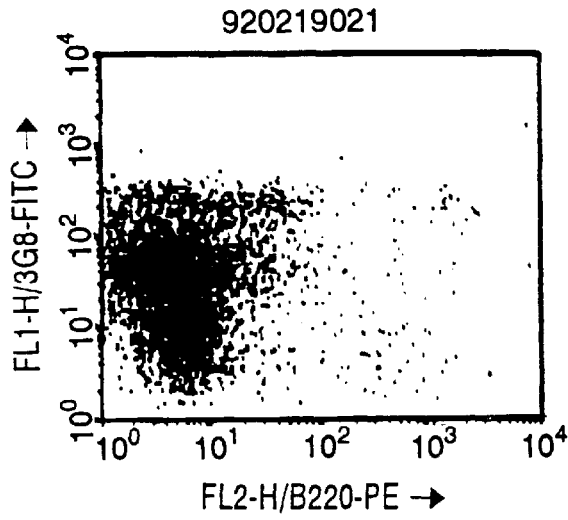

FIG. 23. Protein complexes of the human IgG and IgE Fc receptor family

Members of the Ig-superfamily of Fc receptors are shown. All are membrane spanning molecules, with the exception of FcγRIIIB, which is anchored to the membrane via a GPI tail. Individual subunits are given Greek symbols, e.g. α, β, γ etc. Multiple genes encoding homologous α subunits are referred to as A,B,C. Extracellular domains are indicated as blue spheres. Activation motifs (ARAM), found in the cytoplasmic domains are indicated as bullets, while the inhibitory motif of the B cell FcγRIIB is displayed as a cylinder.

Fifth Series of Experiments

FIGS. 24A–24F. Nontransgenic mouse. Plots show no 3g8 binding on a variety of cell lines.

FIGS. 25A–25F. Transgenic mouse expressing human FcγRIIIB. Shows 3G8 binding on a variety of cell lines.

DETAILED DESCRIPTION OF THE INVENTION

This invention provides a non-naturally occurring non-human vertebrate animal incapable of expressing a functional Fc receptor. In an embodiment of this invention the non-human vertebrate animal is a mammal. The mammal is preferably a rodent. Still more preferably the rodent is a hamster or a murine animal. Examples of murine animals include mice and rats.

The various techniques disclosed herein for mice can be applied to other animals including but not limited to, rats, dogs, sheep, cows, goats, hamsters and gerbils.

In an embodiment, the Fc receptor is a FcγRI, FcγRIIIA, or FcεRI. In a specific embodiment, the animal is incapable of expressing a functional Fc receptor gamma subunit.

In an embodiment, the Fc receptor is a Fc gamma receptor. In a specific embodiment, the Fc gamma receptor is FcγRI, such as for example FcγRIA. In a more specific embodiment, the animal is incapable of expressing a functional FcγRIA alpha subunit.

In another specific embodiment, the Fc gamma receptor is FcγRII, such as for example FcγRIIB. In a more specific embodiment, the animal is incapable of expressing a functional FcγRIIB alpha subunit.

In another specific embodiment, the Fc gamma receptor is FcγRIII, such as for example FcγIIIA. In a more specific embodiment, the animal is incapable of expressing a functional FcγRIIIA alpha subunit.

In another embodiment, the Fc receptor is FcεRI. In a more specific embodiment, the animal is incapable of expressing a functional FcεRI alpha subunit.

This invention provides the animal described above characterized by inability to display an inflammatory response to cytotoxic antibodies.

This invention provides the animal described above characterized by inability to display an inflammatory response to immune complex deposition. Examples of inflammatory response include anaphylaxis; hemorrhage; neutrophil infiltration; edema; phagocytosis; killer-cell mediated lysis; asthma; and rash.

This invention provides the animal described above characterized by inability of the mast cells of the animal to degranulate; by inability of the basophils of the animal to degranulate; by inability of the macrophages of the animal to mediate phagocytosis; by inability of the neutrophils of the animal to mediate phagocytosis; by inability of the neutrophils of the animal to mediate antibody-dependent cellular cytotoxicity; or by inability of the natural killer cells of the animal to mediate antibody-dependent cellular cytotoxicity.

This invention provides a mutated form of isolated animal genomic DNA encoding a functionally deficient Fc receptor. The DNA preferably encodes mammalian Fc receptor. Still more preferably, the DNA encodes rodent Fc receptor, for example mouse, rat or hamster Fc receptor.

In an embodiment the DNA encodes functionally deficient FcγRI, FcγRIIIA or FcεRI. In a specific embodiment, the DNA encodes functionally deficient Fc receptor gamma subunit.

In an embodiment, the DNA encodes functionally deficient Fc gamma receptor.

In a specific embodiment, the Fc gamma receptor is FcγRI. In a more specific embodiment, the Fc gamma receptor is FcγRIA. In an embodiment, the DNA encodes functionally deficient FcγRIA alpha subunit.

In a specific embodiment, the Fc gamma receptor is FcγRII. In a more specific embodiment, the Fc gamma receptor is FcγRIIB. In an embodiment the DNA encodes functionally deficient FcγRIIB alpha subunit.

In a specific embodiment, the Fc gamma receptor is FcγRIII. In a more specific embodiment, the Fc gamma receptor is FcγRIIIA. In an embodiment the DNA encodes functionally deficient FcγRIIIA alpha subunit.

In a specific embodiment, the Fc receptor is FcεRI. In an embodiment, the DNA encodes functionally deficient FcεRI alpha subunit.

In an embodiment the DNA comprises an insertional mutation, and preferably also contains an antibiotic resistance marker. In a specific embodiment, the insertional mutation is insertion of a poly(A) trap vector, for example pMC1-neo.

This invention also provides a vector comprising: the above-described DNA; and DNA flanking sequences adjacent to the DNA encoding functionally deficient Fc receptor, the flanking sequences being homologous to sequences adjacent to the genomic DNA encoding functional Fc receptor.

In a specific embodiment, the vector is a plasmid or a viral vector. In a preferred embodiment, the plasmid vector is pFCRγP.

This plasmid, pFCRγP, was deposited on Aug. 16, 1994 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pFCRγP was accorded ATCC Accession Number 75863.

This invention also provides a non-naturally occurring non-human vertebrate animal incapable of expressing a functional non-human Fc receptor capable of expressing a protein which comprises a domain of a human Fc receptor. The animal may be a mammal. The mammal may be a rodent, for example a mouse, rat or a hamster. As used herein, a Fc receptor domain refers to the shortest amino acid sequence which defines a functional motif; for example a ligand binding motif, receptor assembly motif, intracellular activation motif, or intracellular repression motif. The domain may be the entire extracellular or the entire intracellular portion of a Fc receptor or Fc receptor subunit.

In an embodiment, the protein comprises a human Fc receptor or subunit thereof.

In an embodiment, the subunit is human Fc receptor gamma subunit, alpha subunit, zeta subunit, or beta subunit.

In a specific embodiment, the Fc gamma receptor may be FcγRI, such as for example FcγRIA, FcγRIB or FcγRIC. In another specific embodiment, the Fc gamma receptor is FcγRII, such as for example FcγRIIA, FcγRIIB, or FcγRIIC. In another specific embodiment, the Fc gamma receptor is FcγRIII, such as for example FcγIIIA or FcγIIIB. In another embodiment, the Fc receptor is FcεRI.

This invention also provides an isolated DNA molecule comprising a cell type expression regulating sequence; and a sequence encoding a protein which contains a domain of a human Fc receptor or subunit thereof, under transcriptional control of the cell type expression regulating sequence.

In an embodiment of the above-described DNA, the encoded protein is a human Fc receptor or subunit thereof.

In an embodiment the subunit is human Fc receptor gamma subunit, FcεRI beta subunit, FCγRIII zeta subunit, or Fc receptor alpha subunit.

In more specific embodiments the alpha subunit is a FcγRI alpha subunit, for example a FcγRIA alpha subunit, a FcγRIB alpha subunit, or a FcγRIC alpha subunit; a FcγRIIIA alpha subunit; or a FcεRI alpha subunit.

In another embodiment the Fc receptor is FCγRII, for example FcγRIIA, FcγRIIB or FcγRIIC; or the Fc receptor is FcγRIIIB.

This invention provides a method for identifying a proinflammatory agent dependent on a functional Fc receptor, comprising: administering to a vertebrate animal capable of expressing a functional Fc receptor and to a vertebrate animal incapable of expressing a functional Fc receptor, an amount of the proinflammatory agent effective to induce an inflammatory response in the animal capable of expressing the functional Fc receptor; and determining less inflammatory response in the animal incapable of expressing the functional Fc receptor than in the animal capable of expressing the functional Fc receptor, thereby identifying the proinflammatory agent dependent on the functional Fc receptor. The animal is preferably a mammal, for example a rodent such as a mouse, rat or a hamster.

This invention also provides a method for identifying a proinflammatory agent not dependent on a functional Fc receptor, comprising: administering to a vertebrate animal incapable of expressing the functional Fc receptor an amount of the proinflammatory agent effective to induce an inflammatory response; and detecting an inflammatory response in the animal incapable of expressing the functional Fc receptor, thereby identifying the proinflammatory agent not dependent on the functional Fc receptor. In a specific embodiment, the animal incapable of expressing the functional Fc receptor displays substantially no inflammatory response to the proinflammatory agent. The animal is preferably a mammal, for example a rodent such as a mouse, a rat or a hamster.

In an embodiment of the above-described methods for identifying a proinflammatory agent, the Fc receptor is a mouse Fc receptor.

In another embodiment, a domain of the Fc receptor comprises a human Fc receptor domain. In a specific embodiment, the Fc receptor is a human Fc receptor.

In an embodiment, the Fc receptor is a FcγRI, FcγRIIIA, or FcεRI.

In an embodiment of the above-described method, the animal incapable of expressing the functional Fc receptor is incapable of expressing functional Fc receptor gamma subunit.

In another embodiment, the animal incapable of expressing the functional Fc receptor is incapable of expressing functional Fc receptor alpha subunit or functional Fc receptor beta subunit.

In an embodiment, the Fc receptor is a Fc gamma receptor. In a specific embodiment, the Fc receptor is FcγRI, for example FcγRIA, FcγRIB, or FcγRIC. In a specific embodiment, the Fc receptor is FcγRII, for example FcγRIIA, FcγRIIB, or FcγRIIC. In a specific embodiment, the Fc receptor is FcγRIII, for example FcγRIIIA or FcγRIIIB. In a specific embodiment, the Fc receptor is FcεRI.

The proinflammatory agent may be administered according to techniques known to those of skill in the art, for example intravenously, intraperitoneally, intrathecally, intradermally, intramuscularly, topically, orally, or by inhalation.

This invention provides the above-described method wherein the inflammatory response is anaphylaxis.

The proinflammatory agent may be IgE immune complex or IgG immune complex. In the above-described method the inflammatory response may be selected from the group consisting of edema, hemorrhage, and neutrophil infiltration.

The proinflammatory agent may be an IgG immune complex. The inflammatory response may be is type II acute inflammation.

In an embodiment, the proinflammatory agent is a cytotoxic autoantibody.

This invention provides a method of identifying an anti-inflammatory agent, comprising: administering to a test animal capable of expressing a protein which comprises a domain of a human Fc receptor an amount of a proinflammatory agent capable of inducing an inflammatory response in the animal in the absence of the anti-inflammatory agent, and an inflammation inhibiting effective amount of the anti-inflammatory agent; and determining decreased inflammatory response, thereby identifying the anti-inflammatory agent. The animal is preferably a mammal, for example a rodent such as a mouse, rat or hamster.

The proinflammatory agent and the anti-inflammatory agent may each independently be administered intravenously, intraperitoneally, intrathecally, intradermally, intramuscularly, topically, orally, or by inhalation.

In an embodiment, the inflammatory response is anaphylaxis.

The proinflammatory agent may be IgE immune complex or IgG immune complex. In the above-described method the inflammatory response may be selected from the group consisting of edema, hemorrhage, and neutrophil infiltration.

The proinflammatory agent may be an IgG immune complex. The inflammatory response may be is type, II acute inflammation.

In an embodiment, the proinflammatory agent is a cytotoxic autoantibody.

In an embodiment, the proinflammatory agent and the anti-inflammatory agent are administered simultaneously. In another embodiment the proinflammatory agent is administered after the anti-inflammatory agent. In another embodiment the anti-inflammatory agent is administered after the proinflammatory agent and decreases the inflammatory response induced by the proinflammatory agent.

In a specific embodiment the decreased inflammatory response is determined by comparison to a control animal capable of expressing which comprises a domain of a human Fc receptor to which the proinflammatory agent but not the anti-inflammatory agent has been administered.

This invention also provides a method for determining an anti-inflammatory agent dependent on a Fc receptor, comprising:

(a) administering to a first animal capable of expressing a functional Fc receptor and to a second animal incapable of expressing the functional Fc receptor an amount of the proinflammatory agent effective to induce an inflammatory response in the first animal and in the second animal, the inflammatory response being stronger in the first animal than in the second animal;

(b) administering to the inflamed first and second animals an amount of an anti-inflammatory agent effective to decrease the inflammatory response in the first animal; and (c) detecting decrease of the inflammatory response in the first animal and detecting no decrease of the inflammatory response in the second animal, thereby determing the anti-inflammatory agent dependent on the Fc receptor. The animal is preferably a mammal, for example a rodent such as a mouse, rat or hamster.

In an embodiment of the above-described method the animal is capable of expressing a protein which comprises a domain of a human Fc receptor.

The proinflammatory agent and the anti-inflammatory agent may be administered by techniques known to those of skill in the art. In an embodiment the proinflammatory and anti-inflammatory agents are each independently administered intravenously, intraperitoneally, intrathecally, intradermally, intramuscularly, topically, orally, or by inhalation.

In an embodiment, the inflammatory response is anaphylaxis. In a specific embodiment the proinflammatory agent is IgE immune complex or IgG immune complex.

In another embodiment the inflammatory response is selected from the group consisting of edema, hemorrhage, and neutrophil infiltration. In a specific embodiment the proinflammatory agent is an IgG immune complex.

In an embodiment the inflammatory response is type II acute inflammation. In a specific embodiment the proinflammatory agent is a cytotoxic autoantibody.

This invention also provides an anti-inflammatory agent identified by the above-described methods.

This invention also provides a pharmaceutical composition comprising the anti-inflammatory agent identified by the method described above, and a pharmaceutically acceptable carrier.

In an embodiment of the pharmaceutical composition the anti-inflammatory agent is a polypeptide. In a specific embodiment the polypeptide comprises an antibody Fc domain but no functional antigen binding site. In another specific embodiment the polypeptide is soluble and comprises a Fc receptor ligand binding domain. In another embodiment the polypeptide comprises a Fc receptor-specific antibody or F(ab)$_2$ fragment thereof. An oligopeptide which blocks immune complex binding to immunoglobulin Fc receptors is disclosed in U.S. Pat. No. 4,686,282 (Hahn, 1987). U.S. Pat. No. 5,198,342 (Maliszewski, 1933) discloses DNA encoding IgA Fc receptors.

This invention provides a method for inhibiting stimulation of Fc receptor-bearing cells in a subject, comprising administering to the subject an amount of the above-described anti-inflammatory agent effective to inhibit stimulation of the Fc receptor-bearing cells in the subject.

This invention also provides embodiments wherein the Fc receptor-bearing cells are mast cells, neutrophils, macrophages, natural killer cells, or basophils.

This invention also provides a method for treating a Fc receptor-dependent condition in a subject, comprising administering to the subject an amount of the above-described anti-inflammatory agent effective to treat the Fc receptor-dependent condition in the subject. In an embodiment, the subject is a mammal. Examples of suitable mammals include, but are not limited to, rodents, such as a mouse, rat or hamster, or humans.

This invention provides embodiments wherein the Fc receptor-dependent condition is type III inflammation, IgE-mediated allergy, asthma, anaphylaxis, autoimmune disease, IgG-mediated cytotoxicity, or rash.

This invention provides a method for identifying an agent capable of inhibiting a complex of: a protein and a ligand capable of binding to the protein in the absence of the agent, the protein comprising an extracellular domain of a Fc receptor or Fc receptor subunit. The method comprises: incubating a first incubation cocktail which contains the protein, the ligand, and the agent, and a second incubation cocktail which contains the protein and the ligand but not the agent; detecting the amount of protein-ligand complex in the first and second incubation cocktails; and determining less protein-ligand complex in the first cocktail than in the second cocktail, thereby identifying the agent capable of inhibiting a complex of the protein and the ligand.

In various embodiments the protein may be solubilized in aqueous solution, immobilized on a solid support, or positioned in a lipid bilayer, or positioned in a micelle. In a specific embodiment the lipid bilayer is a membrane.

This invention provides embodiments of the above-described invention in which the Fc receptor is a mammalian Fc receptor. In specific embodiments the mammalian Fc receptor is a murine Fc receptor, a hamster Fc receptor, or a human Fc receptor. The murine Fc receptor may be either a mouse Fc receptor or a rat Fc receptor.

In an embodiment the protein is a Fc receptor or subunit thereof.

In embodiments of the above-described invention the Fc receptor subunit is a gamma subunit, an alpha subunit, or a beta subunit.

In an embodiment the Fc receptor is a Fc gamma receptor. In an embodiment the Fc receptor is FcγRI, for example FcγRIA, FcγRIB, or FCγRIC. In another embodiment the Fc receptor is FcγRII, for example FcγRIIA, FcγRIIB, or FcγRIIC. In an embodiment the Fc receptor is FCγRIII, for example FcγRIIIA or FcγRIIIB. In another embodiment the Fc receptor is FcεRI.

In an embodiment the ligand is a polypeptide. In another embodiment the ligand is a Fc receptor-binding antibody. In specific embodiments the Fc receptor-binding antibody is an IgG, an IgE, or an IgA.

In an embodiment the ligand is labeled. In a specific embodiment the label is a radioactive label. An example of a radioactive label that may be used in this method is $^{125}$I.

In an embodiment of the above-described method the complex is detected by radioimmunoassay. In another embodiment the complex is detected by enzyme-linked immunosorbent assay (ELISA). Examples of useful enzymes for ELISA include horseradish peroxidase, alkaline phosphatase, or beta-galactosidase. ELISA is well known to those of skill in the art and is described, inter alia, in Sambrook, et al., Molecular Cloning: A Laboratory Manual, 2nd ed., (Cold Spring Harbor, 1989).

This invention provides a complex-inhibiting agent identified by the above-described method. This invention further provides a pharmaceutical composition comprising the complex-inhibiting agent identified by the above-described method and a pharmaceutically acceptable carrier.

Further anti-inflammatory agents and complex-inhibiting agents can be generated using molecular modeling techniques known to those of skill in the art. In one such approach, based on a known amino acid sequence of, for example a receptor ligand binding site or other functional motif, and three-dimensional coordinates from similar molecules, a three-dimensional structure is predicted.

One may also treat a subject, including a human subject, for a condition, including but not limited to an autoimmune condition or an inflammatory condition, using gene therapy, based on the results presented herein.

In an embodiment the complex-inhibiting agent is a polypeptide. In a specific embodiment of the pharmaceutical composition, the polypeptide comprises an antibody Fc domain but no functional antigen binding site.

This invention provides a method for inhibiting stimulation of Fc receptor-bearing cells in a subject, comprising administering to the subject an amount of the complex-inhibiting agent effective to inhibit stimulation of the Fc receptor-bearing cells in the subject.

In specific embodiments of this invention the Fc receptor-bearing cells are mast cells, neutrophils, natural killer cells, or basophils.

This invention also provides a method for treating a Fc receptor-dependent condition in a subject, comprising administering to the subject an amount of the anti-inflammatory agent identified by the above-described method effective to treat the Fc receptor-dependent condition in the subject.

In an embodiment of the above-described method the Fc receptor-dependent condition is type III inflammation, IgE-mediated allergy, asthma, anaphylaxis, autoimmune disease, IgG-mediated cytotoxicity, or a rash.

This invention provides a transgenic non-human animal or progeny thereof lacking one or more functional Fc receptors. In a preferred embodiment, the animal is selected from the group consisting of murine non-human animals.

In an embodiment, the Fc receptor comprises an IgG Fc receptor. In another embodiment, the Fc receptor comprises an IgG and an IgE Fc receptor.

In an embodiment, the non-human animal is characterized by its inability to elicit an antibody-mediated inflammatory or allergic response.

This invention provides an isolated nucleic acid molecule comprising a nucleotide sequence encoding a functionally deficient Fc receptor or portion thereof. In an embodiment, the Fc receptor comprises an IgG receptor. In another embodiment, the Fc receptor comprises an IgG and an IgE Fc receptor.

In an embodiment of the isolated nucleic acid molecule described above, the nucleic acid molecule encodes a portion of a Fc receptor which is functional. In another embodiment, the nucleic acid molecule encodes a portion of a Fc receptor which is non-functional.

This invention provides a non-human animal as described above which expresses a Fc receptor comprising a human Fc receptor or portions thereof.

In an embodiment, the Fc receptor is a functional receptor. In a specific embodiment, the Fc receptor comprises an IgG Fc receptor. In another embodiment the Fc receptor comprises an IgG and an IgE Fc receptor.

In a specific embodiment, the non-human animal is selected from the group consisting of murine non-human animals.

In an embodiment, the non-human animal is characterized by its ability to elicit an antibody-mediated inflammatory or allergic response. In another embodiment, the non-human animal is characterized by its inability to elicit an antibody-mediated inflammatory or allergic response.

This invention provides an isolated nucleic acid molecule comprising a nucleotide sequence encoding a protein comprising a human Fc receptor or portions thereof. In an embodiment, the nucleotide sequence encodes an Fc receptor capable of mediating an antibody-mediated inflammatory or allergic response. In a more specific embodiment, the Fc receptor comprises an IgG Fc receptor. In another embodiment, the Fc receptor comprises an IgG and an IgE Fc receptor.

This invention provides a method for identifying an inflammatory or allergenic agent comprising: administering to a first non-human animal which expresses a functional Fc receptor and to a second non-human animal which lacks a functional Fc receptor, said second non-human animal comprising a transgenic non-human animal or progeny thereof, an amount of an agent effective to induce an inflammatory or allergic response in said first non-human animal; and identifying said agent which induces less inflammatory or allergic response in said second non-human animal when compared to said inflammatory or allergic response of first non-human animal.

In an embodiment, the second transgenic non-human animal or progeny thereof lacks one or more functional Fc receptors. The Fc receptor may comprise an IgG receptor. It may also comprise an IgG and an IgE Fc receptor. In an embodiment, the first non-human animal is a transgenic non-human animal or progeny thereof. In an embodiment, the non-human animal is selected from the group consisting of murine non-human animals. In an embodiment, the second non-human animal is characterized by its inability to elicit an antibody-mediated inflammatory or allergic response.

This invention provides a method for identifying an inflammatory or allergenic agent comprising: administering to a transgenic non-human animal or progeny thereof which lacks a functional Fc receptor, an amount of an agent effective to induce an inflammatory or allergic response; and identifying the agent which induces an inflammatory or allergic response in the non-human animal.

In an embodiment, the non-human animal or progeny thereof lacks one or more functional Fc receptors. The Fc receptor may comprise an IgG receptor. It may also comprise an IgG and an IgE Fc receptor. In an embodiment, the first non-human animal is a transgenic non-human animal or progeny thereof. In an embodiment, the non-human animal is selected from the group consisting of murine non-human animals.

This invention provides a method for identifying an anti-inflammatory or anti-allergenic agent comprising:

a) administering to non-human animal which expresses a Fc receptor comprising a human Fc receptor or portions thereof, an effective amount of one or more first agents which induce an inflammatory or allergic response in the non-human animal;

b) administering to the non-human animal an effective amount of one or more second agents which reduce or inhibit the inflammatory or allergic response in the non-human animal induced by the first agent(s); and c) identifying one or more of said second agents which reduce or inhibit the inflammatory or allergic response in the non-human animal.

This invention provides a method for identifying an anti-inflammatory or anti-allergenic agent comprising:

a) administering to the non-human animal which expresses a Fc receptor comprising a human Fc receptor or portions thereof, an effective amount of one or more first agents which inhibit part or all of an inflammatory or allergic response in the non-human animal;

b) administering to the non-human animal an effective amount of one or more seond agents which are capable of inducing an inflammatory or allergic response in the non-human animal of step a) in the substantial absence of the first agent(s); and c) identifying one or more of said first agents which inhibit the inflammatory or allergic response in the non-human animal when one or more of the second agents are administered to the non-human animal.

This invention also provides a method for identifying an anti-inflammatory or anti-allergenic agent comprising: administering to the non-human animal lacking one or more functional Fc receptors and the non-human animal which expresses a Fc receptor comprising a human Fc receptor or portions thereof, an effective amount of an agent which induces an inflammatory or allergic response in the non-human animal lacking one or more functional Fc receptors; and identifying the agent which induces less inflammatory or allergic response in the non-human animal which expresses a Fc receptor comprising a human Fc receptor or portions thereof when compared to the inflammatory or allergic responsse of the non-human animal lacking one or more functional Fc receptors.

This invention provides a method for identifying an agent capable of inhibiting a complex of a protein and a ligand capable of binding to the protein in the absence of the agent, the protein comprising an extracellular domain of a Fc receptor or portion thereof, comprising: incubating a first incubation cocktail which contains the protein, the ligand, and the agent, and a second incubation cocktail which contains the protein and the ligand but not the agent; detecting the amount of protein-ligand complex in the first and second incubation cocktails; and determining less protein-ligand complex in the first cocktail than in the second cocktail, thereby identifying the agent capable of inhibiting a complex of the protein and the ligand.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Structural Diversity of Fc Receptors

Several different classes of receptors have the ability to interact with the Fc domain of immunoglobulins. These include the Ig transporters, exemplified by the poly Ig receptor for IgM and IgA and the IgG transporter of neonatal gut, (Mostov) and the lectin-like molecules which bind to IgE (Conrad). The largest and best characterized group, however, are the Ig Fc receptors which belong to the immunoglobulin supergene family. This group includes the high affinity receptor for IgE on mast cells and basophils, the high and low affinity receptors for IgG and the high affinity receptor for IgA. It is this class of receptors that is commonly meant when the term Fc receptors is used.

The general structural features of the IgG and IgE Fc receptors are summarized in FIG. 23. All are membrane glycoproteins composed of a ligand binding $\alpha$ subunit, which consists of immunoglobulin domains of the C2 class. The $\alpha$ subunits are highly conserved in their extracellular domains, ranging from 70–98% identity within the Fc$\gamma$R groups to 40% identity between the Fc$\gamma$Rs and Fc$\epsilon$RI. In general, Fc$\gamma$Rs interact with all subclasses of IgG, although fine specificity differences have been noted among the subclasses. Only Fc$\gamma$RI binds monomeric IgG, by virtue of a third extracellular Ig domain in the $\alpha$ subunit (Allen and Seed). Fc$\gamma$RII and III bind immunoglobulin with low affinity ($K_a=10^6$) thereby insuring that under physiological conditions these receptors interact exclusively with multivalent immune complexes. In contrast, Fc$\epsilon$RI binds monomeric IgE with very high affinity ($K_a=10^{10}$). The ligand binding promiscuity of these receptors illustrates a general feature of this class of immune receptors, in which the response of a particular cell to crosslinking by immune complexes is governed not by ligand specificity, like in the TCR or BCR, but by the unique transmembrane and cytoplasmic domains of the particular FcR expressed on those cells. Thus, common ligand binding domains are coupled to distinct intracellular domains which thereby transduce different signals in response to a single stimulus (Ravetch, et al.). This is perhaps best exemplified by FC$\gamma$RII. Human neutrophils express the IIA gene (Brooks, et al.; Stuart, et al.), which when crosslinked is responsible for cellular activation of those cells and the subsequent release of proinflammatory mediators. The IIB gene is expressed on B lymphocytes; its extracellular domain is 96% identical to IIA and binds IgG immune complexes in an indistinguishable manner (Brooks et al.; Stuart, et al.). Yet, rather than activating cells, crosslinking of IIB with the antigen receptor on B cells results in the delivery of a signal aborting B cell activation, proliferation and antibody secretion (Amigorena, et al.; Muta, et al). The significant differences between IIA and IIB, illustrated in FIG. 23, are contained exclusively within the cytoplasmic domain of the α subunit. IIA has an activation motif, indicated by the green bullet, while IIB has an inhibitory domain, denoted by the red cylinder. Further structural diversification of IIB results from alternative splicing of a cytoplasmic exon. The product of this alternative splicing has been demonstrated to effect the kinetics of internalization of the receptor on B cells, through the inclusion or exclusion of a cytoskeletal attachment domain (Miettenin, et al.).

Several of the Fc receptors are hetero-oligomeric complexes, such as the high affinity receptor for IgE, FcεRI, and the high and low affinity receptors for IgG, FcγRI (CD64) and III (CD16), respectively. These three receptors require an additional chain for their assembly and signalling: the homodimeric γ subunit (Blank, et al; Ra, et al; Lanier et al; Kurosaki and Ravetch; Ernst et al). The γ subunit and its homologous family member, the ζ chain, serve two distinct functions in the FcR complex: they are essential for cell surface assembly and mediate signalling into the interior of the cell. The ζ chain, first identified as a necessary component of the TCR/CD3 complex (Weissman, et al.), is also associated with FcγRIII on NK cells, where it forms either homodimeric or heterodimeric complexes with the γ chain (Anderson, et al.). Conversely, the γ chain has been found to be associated with the TCR/CD3 complex (Orloff et al.), particularly in gut intraepithelial lymphocytes (IELs) (Malissen, et al.; Ohno, et al.; Liu, et al.; Guy-Grand, et al.) and some CD8$^+$ subsets. Despite the fact that γ and ζ mediate assembly for both the TCR and FcR, these subunits differentiate between these receptor complexes through distinctive interactions (Kurosaki, et al). In the FcRs, γ or ζ assemble with the α subunit in the ER, sparing it from degradation (Kurosaki and Ravetch), while in the TCR, these same chains assemble with a hexameric complex of Ti chains and CD3 subunits in Golgi (Klausner). While the end result is the same, i.e. absence of γ and ζ leading to the loss of surface expression of TCR or FcRs, the interactions are distinct and have been exploited to map critical domains in the assembly of these receptor complexes. As will be discussed below, while the overall pathway of signalling from FcRs and TCR are analogous, important differences have been identified, pointing to distinct functional roles for each of these subunits in signalling from different receptor complexes. FcεRI, in addition to the γ subunit, assembles with a four membrane spanning protein, the β subunit. Its role in FcεRI function will be discussed further below.

The molecular genetics of the FcRs has been determined in several species, with the most detailed information existing for the human gene cluster (Qiu, et al; Brooks). A total of eight genes have been identified and mapped for the FcγRs; three genes for FcγRI, the high affinity receptor (A, B and C) (Ernst, et al), and five genes for the low affinity receptors FcγRII and III: FcγRII A, B and C (Qiu, et al) and FcγRIII A and B (Ravetch and Perussia). The low affinity FcγR genes and two of the genes for the IgE high affinity receptor, FcεRI α and γ subunits, are clustered on chromosome 1q22 (Brooks). This region of 1q22 is syntenic to mouse chromosome 1, where single genes for these receptors are found (Oakey, et al; Seldin, et al.). The three high affinity IgG FcRs also map to chromosome 1, but are more widely dispersed, encoded on 1p13 and 1q21. Consistent with the greater evolutionary distance between the high and low affinity FcγRs, the syntenic region on the mouse chromosome map is found on chromosome 3. Detailed YAC contigs for the human locus encoding the α subunits of FcγRII and FcγRIII indicated the likely manner in which duplication, recombination and diversification gave rise to this family of related ligand binding subunits (Qiu, et al.). Tight linkage of these Ig superfamily members with another, ancestral member of this family, the major myelin protein Po, further suggested that all of these molecules retain their capacity for homophilic interactions with related members of this supergene family. Linkage to this FcR locus has yet to be demonstrated to segregate with known inherited diseases of immune effector function or regulation. However, a locus on chromosome 11q, encoding the β subunit of the high affinity receptor for IgE, FcεRI, has recently been suggested to be a candidate gene for atopy (Shirakawa, et al.), a common phenotype in which individuals have increased serum IgE levels and sensitivity to allergens. A single amino acid substitution in one of the four transmembrane domains is found segregating with the atopic phenotype.

In Vivo Role of FcRS in Inflammation

It has been known for some time that crosslinking of IgE on mast cells by allergen results in the rapid degranulation of those cells and the subsequent physiologic sequelae recognized as the allergic response (Beaven and Metzger). This type of acute hypersensitivity, known as type I inflammation, is thought to be dependant only upon IgE , FcεRI and mast cells to mediate its response. Perturbations in any one of these three components should result in the loss of type I hypersensitivity responses. The critical role of FcεRI was established in experiments in which expression of this receptor was ablated by homologous gene replacement. The resulting mouse could mount neither cutaneous nor systemic anaphylaxis in response to IgE-mediated crosslinking (Dombrowicz et al.; Takai, et al). Those experiments demonstrated unequivocally the role of this high affinity IgE Fc receptor in mediating anaphylaxis, which could not be substituted for by other IgE binding molecules. Mice deficient in mast cells, such as the white-spotting (W) or steele (S) strains, by virtue of lacking either the mast cell growth factor c-kit or its ligand, respectively, are similarly unable to mount an effective IgE mediated anaphylactic response (Ha and Reed; Martin, et al.). While mast cells and FcRs are clearly critical to the anaphylactic response, IgE does not appear to be essential. Mice disrupted in their IgE gene are unable to mount an IgE antibody response to OVA, as might be expected, yet retain the capacity to display systemic anaphylaxis when a sensitized animal is challenged with antigen (Oettingen, et al.). The antibody class responsible for this type of systemic anaphylaxis is likely to be IgG, which triggers its response in the absence of complement, suggesting a direct involvement of IgG immune complexes with FcRs on effector cells. These observations on type I (allergic) inflammation are best understood in light of recent studies on IgG immune complex mediated inflammation, described below. Thus, these in vivo experiments demonstrated that in an IgE triggered response, the interaction of the IgE immune complex with its cognate FcR on the surface of mast cells was the critical initiating step in type I hypersensitivity, resulting in the subsequent changes in vascular permeability and its physiological consequences.

This conceptual framework also holds true for IgG immune complexes in their ability to trigger the classical quartet of symptoms of the inflammatory response: rubor (redness), dolor (pain), calor (heat) and tumor (swelling) or in its more contemporary phrasing, hemorrhage, neutrophil infiltration and edema. IgG immune-complexes are found in many autoimmune diseases, such as lupus and rheumatoid arthritis; together they comprise the type III hypersensitivity class of inflammation (Gallin). Several components have been described which are critical to this response—the IgG immune complex, complement and neutrophils. Depletion of any one of these components is known to result in an attenuated inflammatory response. Thus, mice strains deficient in either complement or neutrophils have significant reductions in the reaction used as model of type III inflammation, the Arthus reaction (Ward and Cochrane; Stetson). In vitro observations suggesting that complement directly binds to IgG immune complexes with direct activation of the complement cascade (Perlmutter and Colten), led to a model for how IgG immune complexes triggered inflammation. In this model complement is necessary to both initiate and amplify the inflammatory response, by generating neutrophil chemotactic factors which result in the influx of neutrophils to the site of IgG immune complex deposition in tissues. These neutrophils are then activated to release proteolytic enzymes and pro-inflammatory mediators by the combined action of complement and Fc receptors. Fc receptors for IgG, in this model of type III inflammation, are not required for the initial neutrophil infiltration observed in the Arthus reaction.

This model was tested in mice in which a homologous disruption of the γ chain resulted in a strain of animals unable to express FcγRI, FcγRIII or FcεRI (Takai, et al). When IgG immune complexes were allowed to be deposited in the skin of these animals, in a reverse passive Arthus reaction, the expected inflammatory response was abolished (Sylvestre and Ravetch). Edema, hemorrhage and neutrophil infiltration were all negligible as compared to their wild-type or heterozygous littermates or to animals deficient only in FcεRI. The absence of neutrophils was particularly surprising, indicating that FcγRs play a critical role in initiating the inflammatory cascade leading to neutrophil chemotaxis. Thus, despite an intact complement system and normal inflammatory responses to other stimuli, in the absence of FcγR triggering by immune complexes, the reaction does not initiate (FIG. 4). The FcγR responsible for this triggering of neutrophil chemotaxis and the subsequent inflammatory response is FcγRIII; the cell type responsible for this initiating event is likely to be the mast cell, based on the observations that the Arthus reaction is attenuated in W/W$^v$ mice (Zhang, et al). These studies suggest that, as in type I hypersensitivity, interaction of IgG immune complexes with their cognate Fc receptors on mast cells is a necessary step in initiating the response which results in the tissue injury observed in autoimmune diseases. The ability of IgE knockout mice to mount a comparable anaphylactic response is consistent with the notion that IgG immune complexes activate effector cells in inflammation and trigger the subsequent cellular events. The contribution of direct complement activation of neutrophil chemotaxis (dotted line) is minimal, based on the Arthus studies in FcγR deficient mice. However, complement is necessary to amplify the type III inflammatory reaction (although apparently not the type I allergic reaction mediated by IgE), since depletion of complement results in an attenuated Arthus reaction. How IgG immune complexes activate neutrophil chemotaxis and the role of mast cell activation in this type of inflammation are new and challenging questions which can now be addressed.

Interaction of immunoglobulins with specific target cells can result in the destruction of those cells by phagocytosis or killer cell mediated lysis (type II acute inflammation). The presence of cytotoxic autoantibodies in autoimmune hemolytic anemia, thrombocytopenia and related disorders indicates the significance of this pathway in the pathogenesis of several diseases. Here, too, the contribution of specific effector cells and soluble mediators have been determined primarily through depletion studies in vivo in available animal models. The role of specific receptors for immune complexes in these reactions has recently begun to be evaluated through the use of monoclonal antibodies to groups of Fc receptors. Those studies suggest that for some specific auto-antibodies, like a mouse anti-RBI of the 2a subclass, erythrophagocytosis is FcR mediated (Shibata, et al.). Clearly, the use of FcR deficient mice will greatly clarify the role of these receptors in reaction of this class of inflammation as well and will likely point to a role for these receptors in triggering cytotoxic antibody responses in general.

These studies on the role of FcRs in vivo suggests that immune complex triggered inflammation, long considered to be a reaction which initiates in the fluid phase through soluble mediators such as complement, is, in fact, a reaction which requires the interaction of soluble immune complexes with specific receptors on select cells. This step of the response, overlooked until quite recently, indicates a role for recognition events which are then amplified through the release of specific soluble mediators, like complement. Thus, Fc receptors would appear to be analogous in this respect to the antigen recognition receptors of lymphoid cells which amplify the exquisitely specific recognition signal by the release of lymphokines. This realization may begin to explain the evolution of the considerable structural diversity of this class of receptors and prompt the re-evaluation of antibody-driven immune responses considered to be independent of a specific cellular recognition step.

References for "Structural Diversity of FC Receptors" and "In Vivo Role of FcRs in Inflammation"

Alber, G., Miller, L., Jelsema, C. L., Varin-Blank, N. and Metzger, H. (1991) Structure-function relationships in the mast cell high affinity receptor for IgE: role of the cytoplasmic domains and of the β subunit J. Biol. Chem 266, 22613–22620.

Allen, J. M., and Seed, B. (1989) Isolation and expression of functional high affinity Fc receptor cDNAs. Science 243, 378–380.

Amigorena, S., Bonnerot, C., Drake. J. R., Choguet, D., Hunziker, W., Guillet, J.-G., Wester, P., Sautes, C., Mellman, I., and Fridman, W. H. (1992) Cytoplasmic domain heterogeneity and functions of IgG Fc receptors in B lymphocytes. Science 256, 1808–1812.

Anderson, P., Caligiuri, M., O'Brian, C., Manley, T., Ritz, J. and Schlossman, S. (1990) FcγRIII(CD16) is included in the ζ NK receptor complex expressed by human natural killer cells. Proc. Natl. Acad. Sci. USA 87, 2274–2278.

Beaven, M. A. and Metzger, H. (1993) Signal transduction by Fc receptors: The FcεRI case. Immunol. Today 14, 222–226.

Blank, U., Ra, C., Miller, L., White, K., Metzger, H., and Kinet, J-P. (1989) Complete structure and expression in transfected cells of high affinity IgE receptor. Nature 337, 187–189.

Brooks, D. G., (1994) Mapping loci encoding IgG receptors and Charcot-Marie-Tooth disease on human chromosome 1. Thesis, Cornell University Medical College/Sloan-Kettering Institute. New York, N.Y. 10021.

Brooks, D. G., Qiu, W. Q., Luster, A. D., and Ravetch, J. V. (1989) Structure and expression of human IgG FcRII (CD32): functional heterogeneity is encoded by the alternatively spliced products of multiple genes. J. Exp. Med. 170, 1369–1386.

Conrad, D. H. (1990) FcεRII/CD23: the low affinity receptor of IgE. Ann. Rev. Immunol. 8, 623–645.

Dombrowicz, D., Flamand, V., Brigman, K. K., Koller, B. H., and Kinet, J.-P. (1993) Abolition of anaphylaxis by targeted disruption of the high affinity immunoglobulin E receptor a chain. Cell 75, 969–976.

Eiseman, E. and Bolen, J. B. (1992) Signal transduction by the cytoplasmic domains of Fc epsilon RI-gamma and TCR-zeta in rat basophilic leukemia cells. J. Biol. Chem. 267, 21027–21032.

Ernst, L. K., Duchemin, A. M., and Anderson, C. L. (1993) Association of the high affinity receptor for IgG (FcγRI) with the γ subunit of the IgE receptor. Proc. Natl. Acad. Sci. USA 90, 6023–6027.

Ernst, L. K., van der Winkel, J. G., Chiu, I. M. and Anderson, C. L. (1992) Three genes for the human high affinity Fc receptor for IgG (Fcgamma RI) encode four distinct transcription products. J. Biol. Chem. 267, 15692–15700.

Gallin, J. I. Inflammation in Fundamental Immunology, third edition W. Paul ed. Raven Press, New York 1015–1032.

Guy-Grand, D., Rocha, B., Mintz, P., Malassis-Seris, M., Selz, F., Malissen, B., and Vassalli, P. (1994) Different use of T cell receptor transducing modules in two populations of gut intraepithelial lymphocytes are related to distinct pathways of T cell differentiation. J. Exp. Med. in press.

Guy-Grand, D. and Vassalli, P. (1993) Gut intraepithelial T lymphocytes. Curr. Opin. Immunol. 5, 247-.

Ha, T-Y and Reed, N. D. (1987) Systemic anaphylaxis in mast cell deficient mice of W/W$^v$ and Sl/Sl$^d$ genotypes. Exp. Cell. Biol. 55, 63-.

Hibbs, M. L., Selvaraj, P., Carpen, O., Springer, T., Kuster, H., Jouvin, M-H., Kinet, J-P. (1989) Mechanisms for regulating expression of membrane isoforms of FcγRIII. Science 246, 1608–1611.

Huizinga, T. W. J., van der Schoot, C. E., Joost, C., Klassen, R., Kleijer, M., vondem Borne, A. E. G. Kr., Roos, D., Tetteroo, P. A. T. (1988) The PI linked receptor FcRIII is released on stimulation of neutrophils. Nature 333, 667–669.

Irving, B. A. and Weiss, A. (1991) The cytoplasmic domain of the T cell receptor ζ chain is sufficient to couple to receptor associated signal transduction pathways. Cell 64, 891–901.

Iwashima, M., Irving, B. A., van Oers, N. S. C., Chan, A. C. and Weiss, A. (1994) Sequential interactions of the TCR with two distinct cytoplasmic tyrosine kinases. Science, 263, 1136–1138.

Jouvin, M-H., Adamczewski, M., Numerof, R., Letourneur, D., Valle, A. and Kinet, J-P. (1994) Differential control of the tyrosine kinases lyn and syk by the two signalling chains of the high affinity immunoglobulin E receptor. J. Biol. Chem 269, 5918–5925.

Keegan, A. D. and Paul, W. E. (1992) Multichain immune recognition receptors: similarities in structure and signalling pathways. Immunol Today 13, 63–68.

Klausner, R. D. (1989) Sorting and traffic in the central vacuolar system. Cell 57, 703–706.

Kurosaki, T., Gander, I., and Ravetch, J. V. (1991) A subunit common to an IgG Fc receptor and the T cell receptor mediates assembly through different interactions. Proc. Natl. Acad. Sci. USA 88, 3837–3841.

Kurosaki, T. and Ravetch, J. V. (1989) A single amino acid in glycosyl phosphatidylinositol attachment domain determines the membrane topology of FcγRIII. Nature 326, 292–295.

Lanier. L. L., Cwirla, S., Yu, G., Testi, R., and Phillips, J. H. (1989) Membrane anchoring of a human IgG Fc receptor determined by a single amino acid. Science 246, 1611–1613.

Lanier, L. L, Yu, G., and Phillips, J. H. (1989) Co-association of CD3γ with a receptor (CD16) for IgG on human natural killer cells. Nature 342, 803–806.

Lefrancois, L. (1991) Extrathymic differentiation of intraepithelial lymphocytes generation of a separate and unequal T cell repertoire? Immunol. Today 12, 436-.

Liu, C. P., Ueda, R., She, J., Sancho, J., Wang, B., Weddell, G., Loring, J., Kurahara, C., Dudley, E. C., Hayday, A., Terhost, C., and Huang, M. (1993) Abnormal T cell development in CD3-ζ$^{-/-}$ mutant mice and identification of a novel T cell population in the intestine. EMBO J. 12, 4863-.

Malissen, M., Gillet, A., Rocha, B., Trucy, J., Vivier, E., Boyer, C., Kontgen, F., Brun, N., Mazza, G., Spanopoulou, E., Guy-Grand, D. and Malissen, B. (1993) T cell development in mice lacking the CD3-ζ/η gene. EMBO J. 12, 4347-.

Martin, T. R., Ando, A, Takeishi, T., Katona, I. M., Drazen, J. M. and Galli, S. J. (1994) Mast cells contribute to the changes in heart rate, but not hypotension or death, associated with active anaphylaxis in mice. J. Immunol. in press.

Miettinen, H. M., Rose, J. K., and Mellman, I. (1989) Fc receptor isoforms exhibit distinct abilities for coated pit localization as a result of cytoplasmic domain heterogeneity. Cell 58, 317–326.

Mizoguchi, H., O'Shea, J. J., Longo, D. L., Loeffler, C. M., McVicar, S. W. and Ocha, A. C. (1992) Alterations in signal transduction molecules in T lymphocytes from tumor bearing mice. Science 258, 1795-.

Mostov, K. E. (1994) Transepithelial transport of immunoglobulins. Ann. Rev. Immunol. 12, 63–84.

Muta, T., Kurosaki, T. Misulovin, Z., Sanchez, M., Nussenzweig, M. C. and Ravetch, J. V. (1994) A 13 amino acid motif in the cytoplasmic domain of FcγRIIB modulates B-cell receptor signalling. Nature 368, 70–73.

Oakey, R. J., Howard, T. A., Hogarth, P. M., Tani, K., and Seldin, M. F. (1992) Chromosomal mapping of the high affinity Fcγ receptor gene. Immunogenetics 35, 279–282.

Oettengen et al. (1994) Nature, in press.

Ohno, H., Aoe, T., Ra, C., Yamamoto, T., and Saito, T. (1993) TCR isoform containing the Fc receptor chain exhibit structural and functional differences from isoform containing CD3ζ. Int. Immunol. 5, 1403-.

Ohno, H., Ono, S., Hirayama, N., Shimada, S. and Saito, T. (1994) Preferential usage of the Fc receptor γ chain in the T cell antigen receptor complex by γ/δ T cells localized in epithelia. J. Exp. Med. 179, 365–369.

Orloff, D. G., Ra, C., Frank, S. J., Klausner, R. D., and Kinet, J-P., (1990) The zeta and eta chains of the T cell receptors and the gamma chain of Fc receptors form a family of disulfide-linked dimers. Nature 347, 189–191.

Perlmutter, D. H. and Colten, H. R. (1986) Molecular immunology of complement biosynthesis: a model of single cell control of effector-inhibitor balance. Ann. Rev. Immunol. 4, 231–51.

Qiu, W. Q., de Bruin, D., Brownstein, B. H., Pearse, R., and Ravetch, J. V. (1990) Organization of the human and mouse low-affinity FcγR genes: evidence for duplication and recombination. Science, 248, 732–735.

Qian, D., Sperlino, A. I., Lancki, D. W., Tatsumi, Y., Barrett, T. A., Bluestone, J. A. and Fitch, F. W. (1993) The γ chain of the high affinity receptor for IgE is a major functional subunit of the T cell antigen receptor complex in γ/δ T lymphocytes. Proc. Natl. Acad. Sci. USA.

Ra, C., Jouvin, M-H., Blank, U., and Kinet, J-P. (1989) A macrophage Fcγreceptor and the mast cell receptor for immunoglobulin E share an identical subunit. Nature 341, 752–754.

Ravetch, J. V. (1994) Atopy and Fc receptors: mutation is the message? Nature Genetics 7, 117–118.

Ravetch, J. V. and Kinet, J-P (1991) Fc Receptors Ann. Rev. Immunol. 9, 457–92.

Ravetch. J. V., Luster, A. D., Weinshank, R. L., Pavlovec, A., Portnoy, D., Hulmes, J., Pan, Y-C., and Unkeless, J. C. (1986) Structural heterogeneity and functional domains of murine immunoglobulin G Fc receptors. Science 234, 718–725.

Ravetch, J. V. and Perussia, B. (1989) Alternative membrane forms of FcγRIII on human NK cells and neutrophils: cell type specific expression of two genes which differ in single nucleotide substitutions. J. Exp. Med. 170, 481–497.

Rodenwald, H-R., Moingeon, P., Lucich, J. L., Dosiou, C., Lopez, P. and Reinherz, E. L. (1992) A population of early fetal thymocytes expressing FcγRII/III contains precursors of T lymphocytes and natural killer cells. Cell 69, 139–150.

Romeo, C. and Seed, B. (1991) Cellular immunity to HIV activated by CD4 fused to T cell or Fc receptor polypeptides. Cell 64, 1037–1046.

Seldin, M. F., Prins, J. B., Rodrigues, N., Todd, J. A. and Meisler, M. H. (1993) Encyclopedia of the mouse genome III. October 1993. Mouse chromosome 3. Mammal. Genome 4, 1–10.

Selvaraj, P., Rosse, W. F., Silber, R., and Springer, T. A. (1988) The major Fc receptor in blood has a phosphatidylinositol anchor and is deficient in paroxysmal nocturnal hemoglobinuria. Nature 333, 565–567.

Shibata, T., Berney, T., Reininger, L., Chicheportiche, Y., Ozaki, S., Shirai, T. and Izui, S. (1990) Monoclonal anti-erythrocyte autoantibodies derived from NZB mice cause autoimmune hemolytic anemia by two distinct mechanisms. Int. Immunol. 2, 1133–1141.

Shirakawa, T., Li, A., Dubrowitz, M, Dekker, J. W., Shaw, A. E., Faux, J. A., Ra, C., Cookson, W. O. C. M. and Hopkin, J. (1994) Association between atopy and variants of the β subunit of the high-affinity immunoglobulin E receptor. Nature Genetics 7, 125–130.

Stetson, C. A. (1951) J. Exp. Med. 94, 349-.

Stuart, S. G., Simister, N. E., Clarkson, S. B., Shapiro, M. and Mellman, I. (1989) The low affinity Fc receptor for human IgG (hFcRII) exists as multiple isoforms. EMBO J. 8, 3657–3666.

Su, Y., Brooks, D. G., Li, L., Lepercq, J., Trofatter, J. A., Ravetch, J. V. and Lebo, R. V. (1993) Myelin protein zero gene mutated in Charcot-Marie-Tooth type IB patients. Proc. Natl. Acad. Sci. USA 90, 10856–10860.

Sylvestre, D. L. and Ravetch, J. V. (1994) Fc receptors initiate the Arthus reaction: redefining the inflammatory cascade. Science, in press.

Takai, T., Li, M., Sylvestre, D., Clynes, R. and Ravetch, J. V. (1994) FcR chain deletion results in pleitropic effector cell defects. Cell 76, 519–529.

Ward, P. A. and Cochrane, C. G. (1964) Fed. Proc. Amer. Soc. Exp. Biol. 23, 509.

Weiss, A. and Littman, D. R. (1994) Signal transduction by lymphocyte antigen receptors. Cell 76, 263–274.

Weissman, A. M., Baniyash, M., Hou, D., Samuelson, L. E., Burgess, W. H. and Klausner, R. D. (1989) Molecular cloning of the zeta chain of the T cell antigen receptor. Science 239, 1018–1021.

Wirthmueller, U., Kurosaki, T., Murakami, M. S. and Ravetch, J. V. (1992) Signal transduction by FcγRIII is mediated through the γ chain. J. Exp. Med. 175, 1381–1390.

Zhang, Y., Ramos, B. F., and Jakchik, (1992) Neutrophil recruitment by tumor necrosis factor from mast cell immune complex peritonitis. Science. 258, 1957–59.

First Series of Experiments

FcγRIIIA (CD16) binds IgG immune complexes with low affinity and mediates the antibody-dependent cytotoxicity of NK cells (1). This receptor is a multimeric complex composed of three functionally and biochemically distinct proteins: IIIAα, a 254 amino acid transmembrane-spanning glycoprotein containing the extracellular ligand binding domain, IIIAγ and IIIAζ, membrane-spanning subunits responsible for both assembly and signal transduction (1). The γ and ζ chains are members of a family of homologous proteins present as homo- or heterodimers, first described as subunits of the high affinity Fc receptor for IgE, FcεRI, and of the T cell antigen receptor/CD3 (TCR/CD3) complex (2). Ligand binding and crosslinking of FcγRIII induce NK cell activation with release of intracytoplasmic granules and upregulation of genes encoding surface activation molecules and cytokines relevant to NK cell biology and functions (3). The early biochemical events induced in NK cells upon engagement of FcγRIII include tyrosine phosphorylation of intracellular substrates ζ and γ chains, phospholipase C (PLC)-γ1 and PLC-γ2, phosphatidylinositol-3 (PI-3) kinase), hydrolysis of membrane phosphoinositides ($PIP_2$), increased $[Ca^{2+}]_i$ and activation of PI-3 kinase (4). The observation that treatment of NK cells with tyrosine kinase inhibitors blocks both FcγRIII-induced hydrolysis of membrane $PIP_2$ and subsequent increase in $[Ca^{2+}]_i$, (4) and later activation events (5) has indicated the involvement of a tyrosine kinase (s) in initiating and/or mediating FcγRIII which could account for its ability to activate cells upon crosslinking. Results from experiments with chimeric molecules containing and γ cytoplasmic domains linked with extracellular domains of heterologous molecules support the hypothesis that a non-receptor kinase(s) associates with FcγRIII possibly via the γ or ζ subunits (6). In cells expressing these chimeric molecules, stimulation of the extracellular domains results in signal transduction.

In order to determine how FcγRIII stimulates protein tyrosine phosphorylation in NK cells, the hypothesis that FcγRIII interacts directly with protein tyrosine kinases in these cells was tested.

Expression of src-related kinases was analyzed in homogeneous NK cell populations obtained from short term (10 d) cocultures of peripheral blood lymphocytes (PBL) with irradiated RPMI-8866 B lymphoblastoid cells (7). The NK cell preparations are >95% homogeneous and have phenotypic and functional properties identical to those of freshly isolated NK cells except that they express late activation antigens and are more readily activatable (7). These NK cells expressed several src-related tyrosine kinases, including $p53^{lyn}$ and $p56^{lyn}$, $p56^{lck}$, p60, and $p62^{fyn}$, as measured by kinase-autophosphorylation in immune-complex protein kinase assays (FIG. 1A). Upon stimulation of FcγRIII with the anti-receptor monoclonal antibody 3G8, rapid activation of at least one of the src-related kinases, $p56^{lck}$, was detected, that was rapidly activated, as analyzed by in-vitro kinase assay on $p56^{lck}$ immunoprecipitates isolated from cells after receptor stimulation (FIG. 1B). Increased $p56^{lck}$ autophosphorylation and phosphorylation of the exogenous substrate enolase was detected as early as 10 s after receptor stimulation. These results are consistent with those previously reported using CD3. Jurkat cells expressing transfected FcγRIIIAα chain in association with endogenous (4), and indicate that $p56^{lck}$ is functionally associated with FcγRIII in primary NK cells.

To determine how $p56^{lck}$ is stimulated upon FcγRIII crosslinking, the receptor from digitonin lysates of NK cells was precipitated and assayed for tyrosine kinase activity in the immunoprecipitates. Tyrosine kinase activity was coprecipitated with FcγRIII and resulted in the phosphorylation of the chain subunit. Phosphorylated chain was preferentially observed within the FcγRIII immunoprecipitate when reprecipitated with anti-$p56^{lck}$ or anti-antibodies (FIG. 2A). These data clearly indicate that is a substrate for $p56^{lck}$-dependent tyrosine phosphorylation and strongly suggest that $p56^{lck}$ coprecipitates with FcγRIII. To determine directly whether $p56^{lck}$ and FcγRIII are physically associated, anti-$p56^{lck}$ immunoblotting was performed on immunoprecipitates isolated from NK cells using FcγRIII ligands on NK cells were solubilized in 1% digitonin to preserve the association of FcγRIIIA subunits. $p56^{lck}$ was specifically detected in immunoprecipitates isolated with either anti-receptor antibody (3G8) (FIG. 2B) or the natural ligand immune complexes (heat-aggregated IgG) (FIG. 2C). Aggregates lacking Fc did not yield $p56^{lck}$ complexes, and isotype-matched anti-CD56 antibodies yielded significantly lower amounts of them. Western blot analysis with an anti-CD16 rabbit polyclonal antibody confirmed that both FcγRIIIAα and chain are present in the 3G8 and the aggregated IgG, but not in the F(ab')$_2$ precipitates (data not shown). The stoichiometry of the FcγRIII-$p56^{lck}$ association appears low: $\leq 1\%$ of total cellular $p56^{lck}$ was coprecipitated with FcγRIII (FIG. 2B, panel B). Similar low levels of association have been reported between TcR and tyn in T cells (8) and may reflect instability of receptor subunits upon detergent extraction. Increased $p56^{lck}$-FcγRIII association could not be demonstrated upon receptor crosslinking (data not shown).

To directly assess which FcγRIII subunit is responsible for the association with $p56^{lck}$ anti-$p56^{lck}$ immunoblotting experiments were performed on immunoprecipitates isolated with anti-polyclonal antisera. NK cells were lysed in 2% NP-40 to reduce possible nonspecific precipitation of $p56^{lck}$ Using a large number of NK cells and a sensitive detection system (Enhanced Chemiluminescence, ECL) a small fraction of total cellular $p56^{lck}$ was detected in the anti-precipitates (FIG. 2D; compare anti-$p56^{lck}$ precipitates with anti-ζ). In addition, a phosphoprotein with molecular mass similar to phospho-ζ(~21kD) was detected in the respective $p56^{lck}$ immunoprecipitates isolated from either digitonin- and, to a lesser extent, NP-40-solubilized NK cells as analyzed by in vitro kinase assays (not shown).

To confirm that $p56^{lck}$ associates with and to determine whether this association is direct or is, in part, mediated by additional proteins, experiments were performed using COS cells cotransfected with various src-family related kinase cDNA (mouse fyn, human yes, and human lck) and a cDNA encoding a chimeric protein composed of the extracellular region of FcγRIIIAα and the transmembrane and cytoplasmic regions of human ζ (IIIA/ζ). Transfected cells were lysed in 3% NP-40, immunoprecipitates were collected using either anti-antibody coupled-Sepharose or control antibody-Sepharose and subjected to immunoblotting with the respective anti-src-related kinase antibody. Coprecipitation of IIIA/ and $p56^{lck}$, but not fyn or yes (FIGS. 3A–3C) or src (not shown), was detected. Similar experiments in COS cells cotransfected with $p56^{lck}$ and γ cDNAs revealed association of these two proteins, although to levels lower than those observed with (FIG. 3D).

Results indicated that the src-related kinase $p56^{lck}$ associates both functionally and physically with the FcγRIIIA complex on NK cells. This association appears to be mediated in part via the chain. The results of ζ/γ/$p56^{lck}$ cotransfection experiments in COS cells prove that $p56^{lck}$ and either ζ or γ subunits can associate via direct interaction. Although the molecular basis of the association remains to be determined, it is likely to depend, in part, on the antigen receptor homology 1 motifs (ARH1) of ζ/γ which are conserved sequences [(ASP or GLU)-X$_7$-(ASP or GLU)-TYR-X-LEU-X$_7$-TYR-X$_2$-(LEU or ILE) (SEQ ID NO:2–9)] found in many receptor signal transducing chains, including TCRζ, η, γ, and ε, FcεRI β and γ chains, B cell antigen receptor chains Ig-α (mb1) and Ig-β (B29), and human FcγRIIA (9). Evidence to support the contention that these sequences mediate coupling of receptors to signaling pathways has been provided for the B cell antigen receptor chains Ig-α and Ig-β (10). Differential binding patterns of the ARH1 regions in these proteins for cytoplasmic effectors were observed, indicating that the presence of an ARH1 motif is insufficient for binding cytoplasmic effector molecules but that additional chain-specific residues determine binding specificity and a single motif can bind more than one effector molecule (10). Preliminary data indicates that the $p56^{lck}$-ζ interaction depends on the presence of ARH1 motifs in, and deletion of one or more of them results in a proportionally decreased association (not shown). This may also explain, in part, the detection of lower levels of $p56^{lck}$ associated with γ chain (a single ARH1 motif) as compared to ζ(3 ARH1 motifs). The $p56^{lck}$ domain involved in this interaction has not been defined. It is likely to differ from that involved in the interaction between $p56^{lck}$ and CD4, shown to depend on the NH$_2$-terminal sequence of this molecule (11), because no sequence homology is found between the ARH1 motif and CD4.

Functional interaction between $p56^{lck}$ and the ζ/γ subunit is supported by observations in T cells. Elegant studies using $p56^{lck}$-deficient cell lines (which endogenously express fyn) strongly support a role for $p56^{lck}$ in signal transduction via the TCR and in cell-mediated cytotoxic responses (12). Cytotoxic functions are restored upon re-expression of $p56^{lck}$ and, most interestingly in regard to NK cells, appear independent of CD4 or CD8 engagement (12). Although cotransfection experiments in COS cells demonstrate a direct interaction of $p56^{lck}$ and ζ/γ, additional proteins may be necessary to mediate optimal association or disassociation of these two molecules in primary cells. The situation in NK cells may be analogous to that observed in T cell lines. A 70 kD protein (ZAP-70) has been observed to associate with ζ in the Jurkat T cell line upon TCR/CD3 stimulation (13). Proteins of similar size are rapidly phosphorylated upon engagement of the B cell antigen receptor complex (p72$^{syk}$), the FcεRI complex (14), and FcγRIII in NK cells (4, and unpublished data). Although the role of these 70–72 kD proteins/kinases is unknown, they may function to stabilize the primary interaction of ARH1 containing subunits with src-related protein tyrosine kinases.

References and Notes of the First Series of Experiments

1. J. V. Ravetch and J. P. Kinet, *Annu. Rev Immunol.* 9, 457 (1991).
2. D. G. Orloff, C. Ra, S. J. Frank, R. D. Klausner, J. P. Kinet, *Nature* 347, 189 (1990).
3. I. Anegon, M. C. Cuturi, G. Trinchieri, B. Perussia, *J. Exp. Med* 167, 452 (1988); M. C. Cuturi et al., *J. Exp. Med.* 169, 569 (1989).
4. L. Azzoni, M. Kamoun, T. Salcedo, P. Kanakaraj, B. Perussia, J. Exp. Med in press (1992); M. A. Cassatella et al., *J. Exp. Med.* 169, 549 (1989); P. Kanakaraj et al., in preparation.
5. J. J. O'Shea, D. W. McVicar, D. B. Kuhns, J. R. Ortaldo, *J. Immunol.* 148, 2497 (1992).
6. B. A. Irving and A. Weiss, *Cell* 64, 891 (1991); Romeo and Seed, *Cell* 64, 1037 (1991); F. Letourneur and R. D. Klausner, *Proc. Natl. Acad. Sci.* 88, 8905 (1991); E. Eiseman and J. B. Bolen, *J. Biol. Chem.* 267, 21027 (1992); C. Romeo, M. Amiot, B. Seed, *Cell* 68, 889 (1992).
7. B. Perussia et al., *Nat. Immun. and Cell Growth Requl.* 6, 171 (1987).
8. L. E. Samelson, A. F. Phillips, E. T. Loung, R. D. Klausner, *Proc. Natl. Acad. Sci. U.S.A.* 87, 4358 (1990).
9. M. Reth, *Nature* 338, 383 (1989); A. M. K. Wegener et al., *Cell* 68, 83 (1992).
10. M. R. Clark et al., *Science* 258, 123 (1992).
11. A. S. Shaw et al., *Cell* 59, 627 (1989); J. M. Turner et al., ibid. 60, 755 (1990); A. S. Shaw et al., *Mol. Cell. Biol.* 10, 1853 (1990).
12. D. B. Straus and A. Weiss. *Cell* 70, 585 (1992); L. Karnitz et al., *Molec. and Cellul. Biol.* 12, 4521 (1992).
13. A. C. Chan, B. A. Irving, J. D. Fraser, A. Weiss, *Proc. Natl. Acad. Sci. U.S.A.* 88, 9166 (1991); R. L. Wange, A. N. Tony Kong, L. E. Samelson, *J. Biol. Chem.* 267, 11685 (1992).
14. J. E. Hutchcroft, M. L. Harrison, R. L. Geahlen, *J. Biol. Chem.* 266, 14846 (1991); J. E. Hutchcroft, R. L. Geahlen, G. G. Deanin, J. M. Oliver, *Proc. Natl. Acad. Sci. U.S.A.* 89, 9107 (1992).
15. M. P. Cooke and R. M. Perlmutter, *New Biol.* 1, 66 (1989).
16. J. Sukegawa et al., *Molec. Cellul. Biol.* 7, 41 (1987).
17. Y. Koga et al., *Eur. J. Immunol.* 16, 1643 (1986).
18. M. Mishina et al., *EMBO J.,* 1, 1533 (1982).
19. T. Kurosaki, I. Gander, J. V. Ravetch, *Proc. Natl. Acad. Sci. USA* 88, 3837 (1991).
20. J. Sukegawa et al., *Oncogene* 5, 611 (1989).
21. Y. Mori et al., *Japan J. Cancer Res.* 82, 909 (1991).

Second Series of Experiments

Surface immunoglobulin complex is composed of antigen recognition substructure, membrane immunoglobulin (mIg) and associated signal transduction subunit, Ig-α (mb-1) and Ig-β (B29). These mIg-associated chains contain within their cytoplasmic domains a conserved motif of six precisely spaced amino acids, the antigen receptor homology 1 motif (ARH1), which carries sufficient structural information to activate signaling pathways. Engagement of the surface immunoglobulin complex trigger B-cell differentiation and proliferation through activation of tyrosine kinase(s), mobilization of intracellular $Ca^{2+}$, and activation of protein kinase C. Crosslinking FcγRII with the surface immunoglobulin complex confers a dominant inhibition signal that prevents or aborts the activation. Here, it is shown that FcγRII modulates mIg induced $Ca^{2+}$ mobilization by inhibiting $Ca^{2+}$ influx from the outside, whereas the activation pattern of tyrosine phosphorylation is not altered by the cross-linking FcγRII with mIg. A 13 residue motif of the cytoplasmic domain of FcγRII was able to be appended to the intracellular domain of other proteins to inhibit the $Ca^{2+}$ mobilization upon the stimulation of the mIg. Calcium mobilization induced by chimeric IgM/Ig-α and IgM/Ig-β molecules in which the cytoplasmic domain of mIgM were substituted with the corresponding Ig-α and Ig-β, was modulated by the cross-linking FcγRII with these receptors. These data suggest that the 13 residue motif in FcγRII modulates the $Ca^{2+}$ signaling activated by the ARH1 motif in Ig-α and Ig-β subunits of surface immunoglobulin complex.

Figure 5B:
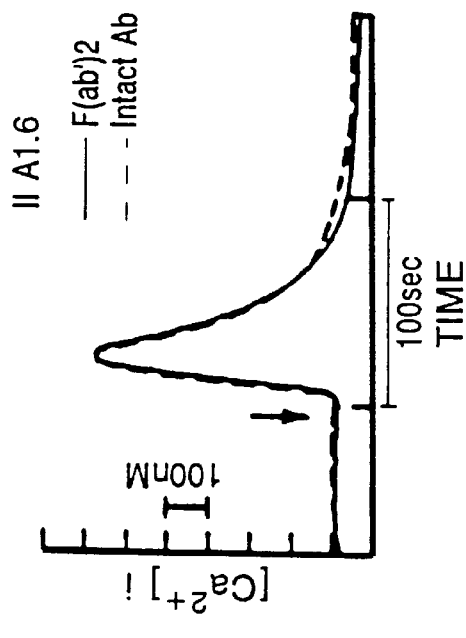
Figure 5D:
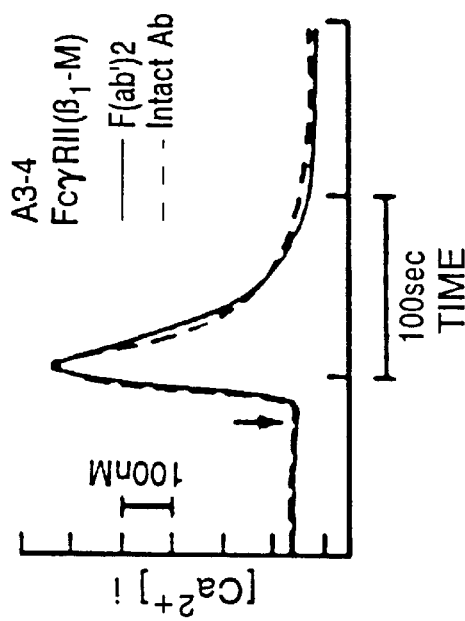
Figure 5A:
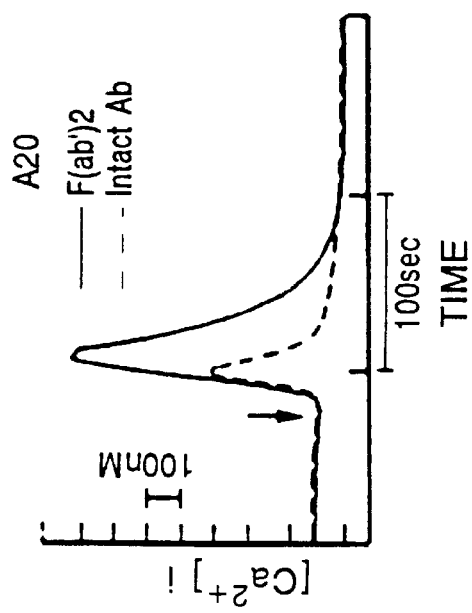
Figure 5C:
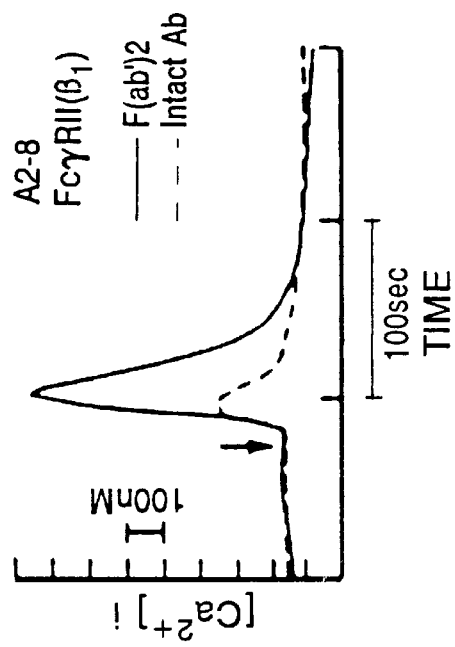
Figure 5E:
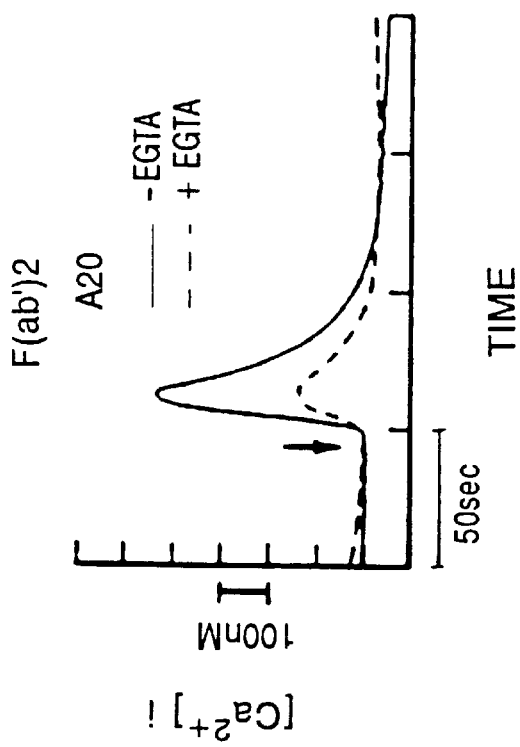
Figure 5F:
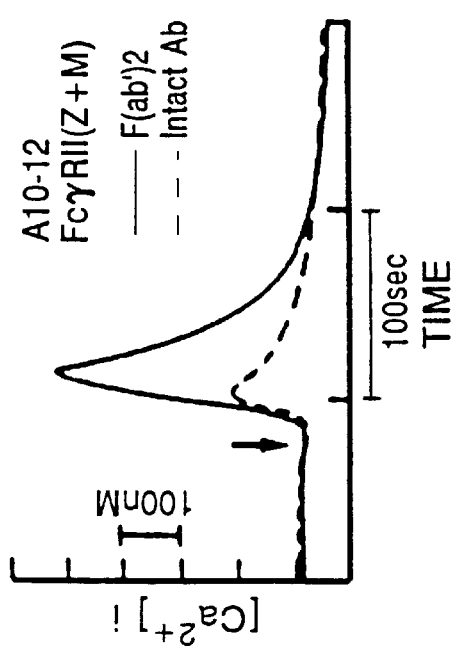
Figure 5G:
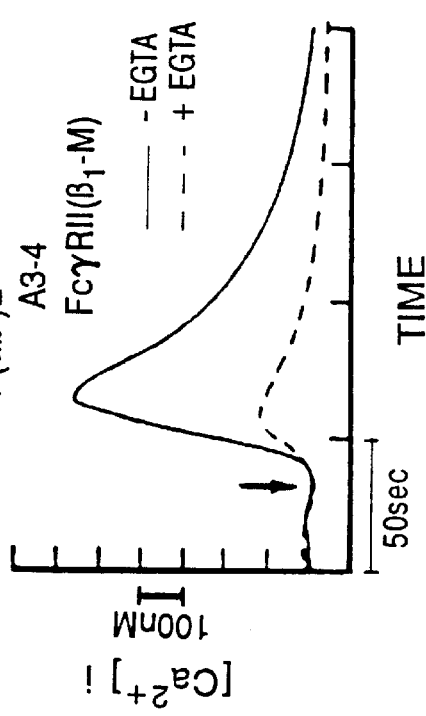
Figure 5H:
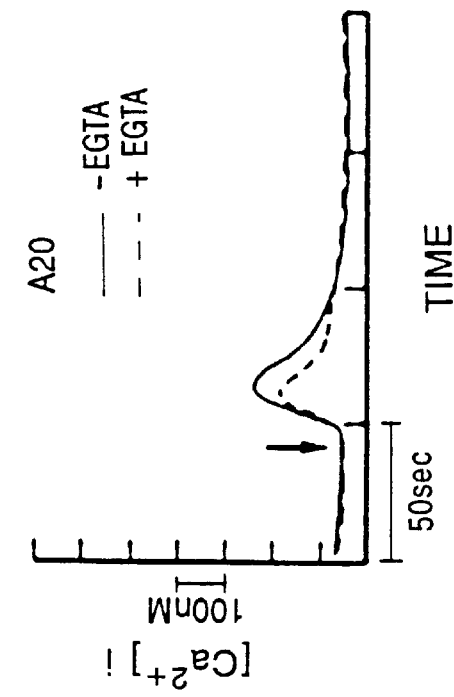
Figure 5J:
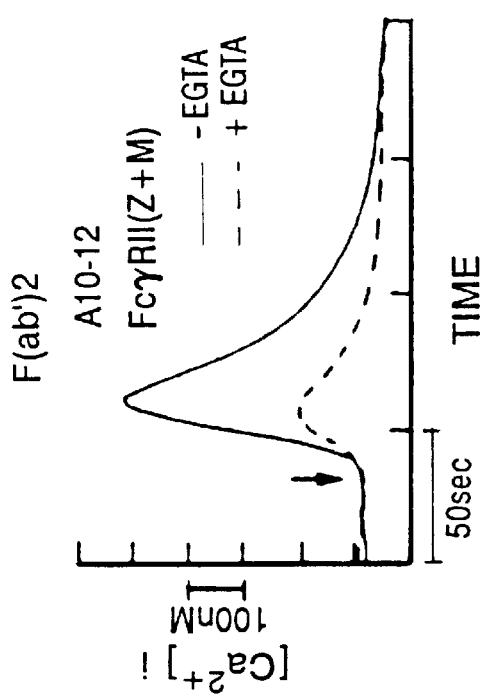
Figure 5I:
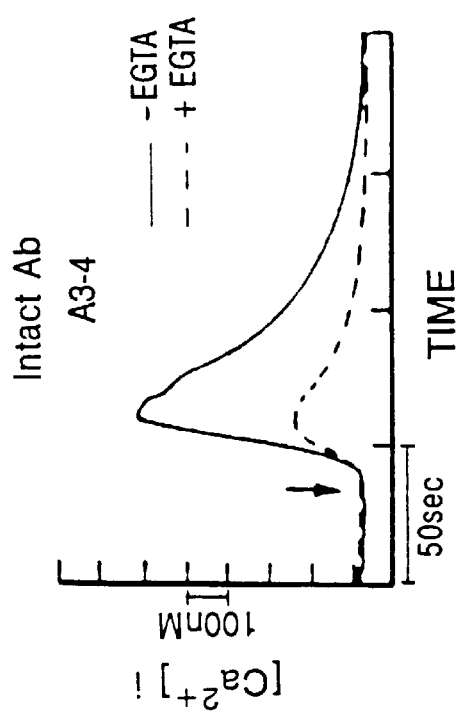
Figure 5K:
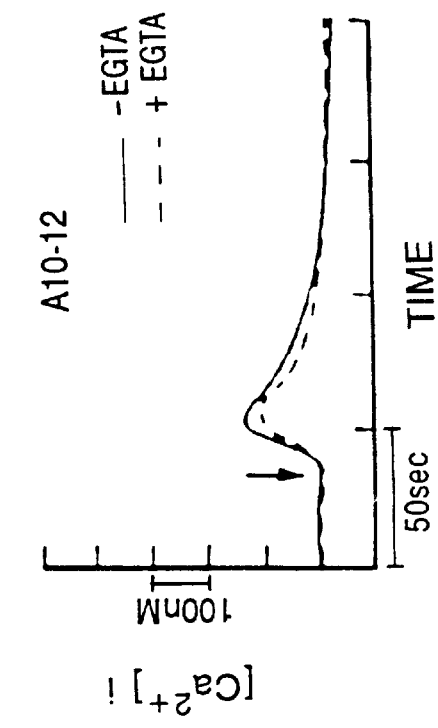

FcγRII (β1 isoform) is expressed at high levels on B cells where they are involved in modulating B cell activation by surface immunoglobulin complex. Typically, cross-linking of mIg by antigen or anti-Ig F(ab')$_2$ antibody induces a transient increase in cytosolic free $Ca^{2+}$, a rise in inositol-3-phosphate (IP$_3$), activation of protein kinase C and enhanced protein tyrosine phosphorylation. Experiments were done to determine which of the proximal events induced by the stimulation of mIg is inhibited by the crosslinking FcγRII together with mIg. By adding anti-mIg (whole IgG directed towards the mIg), which cross-linked surface FcγRII with mIg, inhibited the $Ca^{2+}$ mobilization in the A20 B-lymphoma cell line (FIG. 5A). This inhibition was reversed in the presence of 2.4G2 mAb which prevented the binding of the intact Fc domain of the anti-mIg to FcγRII (data not shown). Stimulation of mIg evokes both $Ca^{2+}$ release from intracellular stores and $Ca^{2+}$ influx from the outside. To distinguish which $Ca^{2+}$ movements is modulated by cross-linking FcγRII with mIg, A20 cells were stimulated in the presence or absence of EGTA. EGTA incubation decreased the $Ca^{2+}$ mobilization upon the cross-linking of mIg with anti-mIg F(ab')$_2$ almost 4-fold, whereas even in the presence of EGTA, $Ca^{2+}$ mobilization induced by adding whole anti-mIg was almost the same (FIG. 5B). This result indicates that the $Ca^{2+}$ modulation by FcγRII is primarily due to the inhibition of $Ca^{2+}$ influx across the plasma membrane. Comparison of tyrosine phosphorylated proteins of A20 cell lysates stimulated by whole or F(ab')$_2$ anti-mIg antibody showed no significant change. And also did not detect difference of the stimulation of tyrosine phosphorylation of phospholipase C-γ1 by whole or F(ab')$_2$ antibodies (data not shown). Since phospholipase C-γ1 is presumably involved in IP$_3$ formation, and IP$_3$ induces the $Ca^{2+}$ mobilization from the intracellular compartment, this observation supports the previous conclusion that FcγRII modulates mainly $Ca^{2+}$ influx from the outside upon the engagement of mIg.

To define the functional region(s) within the FcγRII cytoplasmic domain responsible for inhibition signal of $Ca^{2+}$ mobilization via membrane immunoglobulin complex, cDNA encoding 13 residues internal deletion of FcγRII cytoplasmic domain was transfected into IIA1.6 cell line, FcγRII negative mutant of the A20 B-cell lymphoma (FIG. 4A). The designated clone was selected based on high level of surface expression assayed by flow cytometry (FIG. 4B). In contrast to the wild type of FcγRII, this internal deletion mutant showed no modulation of $Ca^{2+}$ influx by cross-linking FcγRII together with mIg (FIG. 5A). To determine whether this 13 residue segment of FcγRII cytoplasmic domain is sufficient to inhibit the $Ca^{2+}$ mobilization, the fusion construct in which the first 18 residue and the following 13 residue of the cytoplasmic domain, are derived from the ζ chain of TCR/CD3 complex and FcγRII respectively (FIG. 4A), was transfected into IIA1.6 cell line. This fusion receptor was able to inhibit the $Ca^{2+}$ mobilization by cross-linking FcγRII with mIgG and also this modulation was due to blocking the $Ca^{2+}$ influx from the outside the cells (FIG. 5A and 5B). These results demonstrate that the 13 residue motif in the cytoplasmic domain of FcγRII has a sufficient structural information to inhibit mIg induced $Ca^{2+}$ mobilization.

As late responses, analyzation of the effect of the 13 residue segment of FcγRII on the modulation IL-2 secretion via mIg. As expected, wild type FcγRII modulated IL-2 secretion by crosslinking FcγRII with mIgG, whereas the 13 residue deleted FcγRII abolished this modulation. The fusion receptor FcγRII(Z+M) showed the significant modulation, however compared with the wild type FcγRII, the modulation extent was almost half (FIG. 7). This weak modulation by FcγRII (Z+M) was not due to the cell surface density of FcγRII(Z+M), shown by flow cytometric analysis (FIG. 4B). These results suggest that the 13 residue segment in the cytoplasmic domain of FcγRII is required for the modulation of late responses, but for complete modulation of late responses, possibly other cytoplasmic region(s) of FcγRII is also necessary.

Surface immunoglobulin complex is composed of membrane immunoglobulin (mIg) and associated signal transduction subunit Ig-α (mb1) and Ig-β (B29). The ARH1 motif located in the cytoplasmic domain of these associated chains was shown to carry sufficient structural information to activate signaling pathway. However, recent in vitro and in vivo experiments have demonstrated that the cytoplasmic domains of Ig-α and Ig-β interact with different cytoplasmic effector proteins, resulting in the differential biological capability. To asses directly whether FcγRII modulates Ig-α and Ig-β dependent signaling, the chimeric IgM/Ig-α and IgM/Ig-β constructs in which the extracellular and transmembrane domains are derived from mIgM and the cytoplasmic domain from Ig-α and Ig-β, were transfected into A20 B cell lymphoma. To avoid the association of these chimeric molecules with endogenous Ig-α and Ig-β, introduction of the mutations (tyr-ser to val-val) in the transmembrane domain of mIgM. It was already shown that the introduction of non-polar groups such as val-val in place of tyr-ser in the transmembrane domain of mIgM produces a receptor that can no longer associate with Ig-α and Ig-β. Even though the cell surface expression of IgM/Ig-α and IgM/Ig-β was not so high (FIG. 7A), crosslinking of these chimeric molecules with anti-IgM F(ab')$_2$ evoked $Ca^{2+}$ mobilization. Crosslinking FcγRII with IgM/Ig-α and IgM/Ig-β inhibited this $Ca^{2+}$ mobilization and in the presence of 2.4G2, this inhibition was reversed (FIG. 7B and 7C). These results indicate that FcγRII prevents mIgM induced $Ca^{2+}$ activation presumably through the ADH1 motif located in the cytoplasmic domain of Ig-α and Ig-β.

It is well known that the early biochemical events induced in B cells upon engagement of surface lmmunoglobulin complex include tyrosine phosphorylation of intracellular substrates, hydrolysis of phosphoinositides, increased intracellular $Ca^{2+}$. Although there are several suggestions that FcγRII interacts with elements in the mIg signaling pathway, the molecular nature of the inhibitory FcγRII-mediated signal on B cell activation is unknown. Results show that $Ca^{2+}$ influx across the plasma membrane induced by mIg is primarily inhibited by the cross-linking FcγRII together with mIg. The $Ca^{2+}$ mobilization from the intracellular compartment is not modulated. This conclusion is strengthened by the observation that stimulation of tyrosine phosphorylated of PLC-γ1 and IP$_3$ turnover was not modulated by the crosslinking FcγRII with mIg. Any significant difference of induction of tyrosine phosphorylation by assessing the cell lysates with anti-phosphotyrosine antibody, was not detected, suggesting that FcγRII does not modulate overall induction of tyrosine phosphorylation by engagement of surface immunoglobulin complex.

The results presented here suggest that the active site of FcγRII to inhibit mIg-induced $Ca^{2+}$ mobilization is a 13 residue short linear peptide sequence. It appears likely that the interaction of this motif with one or at most few proteins suffices to mediate $Ca^{2+}$ modulation. Since recent reports showed that the interaction of SH2 containing proteins with peptides is through phosphotyrosine and isoleucine binding pockets spaced by two amino acids, next focus will be destined to the involvement of phosphotyrosine included in this 13 residue motif.

As a simple model system, transfection of IgM/Ig-α and IgM/Ig-β chimeric molecule, whose ADH1 motif in the cytoplasmic domains of Ig-α and Ig-β is presumably involved solely in the receptor activation, was performed. $Ca^{2+}$ mobilization induced by these chimeric molecules was significantly modulated by cross-linking FcγRII with IgM/Ig-α and IgM/Ig-β, indicating that FcγRII inhibit both Ig-α and Ig-β dependent $Ca^{2+}$ signaling.

Third Series of Experiments

SUMMARY

The γ subunit of immunoglobulin Fc receptors is an essential component of the high affinity receptor for IgE (FcεRI), the low affinity receptor for IgG (FcγRIII) and is associated with the high affinity receptor for IgG (FcγRI) and the T cell receptor/CD3 complex. It is required both for receptor assembly and signal transduction. Targetted disruption of this subunit results in immunocompromised mice. Activated macrophages from γ-chain deficient mice unexpectedly lack the ability to phagocytose antibody-coated particles, despite normal binding. Defects in NK cell mediated antibody-dependant cytotoxicity and mast cell mediated allergic responses are evident in these animals, establishing the indispensable role of FcRs in these responses. However, loss of γ chain does not appear to perturb T cell development since both thymic and peripheral T cell populations appear to be normal. These mice thus represent an important tool for evaluating the role of these receptors in humoral and cellular immune responses.

The structural heterogeneity of Fc receptors for IgG, in which the IgG immune complex interacts with a diverse array of related receptors, and the overlapping pattern of FcR expression on effector cells has precluded detailed determination of the specific functions of individual receptors in mediating effector responses in vivo. A mouse strain has been created genetically deficient in the γ subunit by homologous recombination in ES cells in order to determine the roles of FcγRIII and FcεRI in effector responses to IgG and IgE, respectively. Selective ablation of this chain has indeed resulted in the loss of these receptors on NK cells, macrophages, and mast cells. The functional deficit, however, is more pronounced than would have been predicted from in vitro reconstitution studies alone. Inflammatory macrophages are unable to mediate phagocytosis through FcγRI, II or III, indicating an unexpected pleiotropic role of this subunit. These mice thus provide the first clear mutations with which it can determined that the distinct roles of these structurally similar receptors in mediating effector responses in host defense.

RESULTS

Targted Disruption of the γ Subunit Gene in ES Cells

The γgenomic locus was cloned from a λ library constructed from DNA isolated from 129/Ola mice. The γ subunit gene was shown to be organized in 5 exons (FIG. 1A) with the same intron-exon organization and sequence as has been described for the human counterpart (Kuster, et al. 1987).

To construct an efficient targeting vector for γ locus, employment of the poly(A) trap vector pMC1-neo (Thomas and Capecchi, 1987), which was inserted into the second exon of the γ subunit genomic subclone (FIG. 8A). This insertion creates a new stop codon 239 bp downstream of the integration site; a homologous recombination event at the γ locus would generate a nonfunctional polypeptide. The γ subunit homologous recombination construct, pFCRγP, contains 7.1 kb of homology 5' and 1.2 kb 3' of the neo insertion (FIG. 8A).

pFCRγP was electroporated into E14 ES cells, and the transfected population was selected with G418 and FIAU. 18 homologous integration events were identified by Southern blot analysis, nine of which were chosen for further characterization (FIGS. 8B–8E) and were determined to result from a single integration event that occurred at the γ subunit locus. The mutant allele will be referred to as FcRγ$^{n1}$. Chimeras were established with eight of these clones, according to standard methods. Two of seven male chimeras transmitted the mutant allele to their offspring (FIG. 8F). Homozygous FcRγ$^{n1}$ animals were present at the expected frequency, indicating that disruption of the γ subunit locus did not result in embryonic lethality. The homozygous mutant mice appeared grossly normal and were fertile.

One of the transfected ES cell lines, Fcγ$^{n1}$, was deposited on Aug. 16, 1994 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. ES cell line Fcγ$^{n1}$ was accorded ATCC Accession Number CRL 11700.

Verification of the FcRγ$^{n1}$ Null Allele: RNA Analyses

RT-PCR analysis of macrophage, NK cell and mast cell RNA isolated from wild-type, heterozygous, and homozygous mutant mice was performed to determine the expression of γ chain RNA. A 137-bp fragment specific for a transcript containing exon 1 and 2 sequences, which is located upstream of neo integration site, was observed in wild-type and heterozygous animals, whereas homozygous mutant mice had no detectable fragment in macrophages, and a faint band in mast and NK cells (FIGS. 9A and 9B). Similar results were obtained using primers specific for exons 1 and 5. PCR analysis using neo and exon 5 primers detected the expected 197-bp fragment in macrophages from homozygous as well as heterozygous animals (FIG. 9A). Intact γ message could not be detected in RNA isolated from brain, thymus, heart, lung, spleen, and kidney (data not shown).

Mutant Mice Lack Wild-Type γ Subunit Polypeptide

Protein extracts were prepared from macrophages, NK, and mast cells and subjected to Western blot analysis with an anti-γ chain antibody. FIG. 9B shows that the band of 6–9 kD expected for the γ subunit protein (Alcaraz et al., 1987) was present in cells from wild-type but not from those of homozygous mutants. No abnormal γ subunit cross-reacting proteins were detected in cells from homozygous mice even in a 6-fold longer exposure (data not shown). Thus, it is concluded that the targeted mutation resulted in a mutant allele that does not produce a γ subunit protein.

Flow Cytometric Analysis of FcγRIII and FcεRI Expression

To determine if theγ chain disruption indeed resulted in the loss of expression of FcγRIII and FcεRI, macrophages, neutrophils, mast cells, and splenic NK cells were harvested from the γ-deficient mice and their wild-type or heterozygous littermates. Thioglycollate-elicited peritoneal macrophages (TEM) were stained with a monoclonal antibody, 2.4G2, which recognizes both low affinity FcγRs (II and III) and counterstained with a macrophage marker, Mac-1. As seen in FIGS. 10A–10C, macrophages derived from +/+ and +/– mice are positive for both 2.4G2 and Mac-1, while the –/– mice show an 80% reduction in 2.4G2 staining, without a reduction in Mac-1 staining, suggesting the loss of FcγIII, with retention of FcγII on these macrophages.

Bone marrow derived neutrophils were characterized by flow cytometry using 2.4G2 and a granulocyte marker Gr-1. Wild-type (+/+) as well as heterozygous (+/–) mice show a double positive population of cells (FIG. 10D–10F); homozygous (–/–) mice have equivalent Gr-1 staining, with 2.4G2 staining reduced by 50%.

NK cells express only FcγRIII (Perussia et al., 1989); loss of γ chain would either result in the total ablation of surface expression of this FcγR or normal levels of expression if ζ chain is able to substitute for γ subunit efficiently. IL-2 stimulated splenic NK cells were stained with 2.4G2 to detect FcγRIII expression and with a murine NK cell specific mAb, 4D11, which stains 50% of NK cells. As shown in FIGS. 10G–10I, the NK cells isolated from the homozygous γ-deficient mice are not stained with 2.4G2, yet retain their 4D11 staining profile. Littermate control wild type mice are 4D11 and 2.4G2 positive.

Both peritoneal and bone-marrow derived mast cells were stained with FITC-labelled IgE and a monoclonal antibody to c-kit, Ack2. FIGS. 10J–10L shows that mast cells isolated from –/– mice lack IgE binding as a result of the loss of FcεRI. These cells also have reduced expression of FcγRIII, detected by reduced 2.4G2 staining (data not shown).

These data indicate that loss of γ chain results in the loss of FcγRIII and FcεRI expression on cells where those receptors are normally present. FcγRII expression on B lymphocytes is unchanged (FIGS. 11G and 11H). Analysis of T cell populations from the thymus (FIGS. 11A–11D) and spleen (FIG. 11E–11H) of 2 week old and 10 week old γ-deficient mice have not revealed any distortion in the normal ratios of CD4 and CD8 cells (FIGS. 11A and 11B)

and TCR αβ (FIGS. 11C and 11D). Both mutant and wild type animals display 70% double positive, 22% Cd4⁺ CD8⁻, 6% CD4⁻ CD8⁺ and 2% CD4⁻ $^{CD}8^-$. In contrast to the T cell populations in γ-chain deficient mice, ζi-chain knockout mice show impaired development of CD4 and CD8 single positive cells and peripheral T cells have few T cell receptors (Love et al., 1993).

Phagocytic Activity is Absent in γ-Deficient Mice

FcγRIII, in common with FcγRI and II, mediates ADCC, phagocytosis, release of inflammatory mediators and degranulation when crosslinked with antigen-antibody complexes. Since the deletion of γ chain in mouse resulted in the marked reduction or total loss of FcγRIII, functional characterization of the macrophage, NK and mast cells from these γ-deficient animals were studied to determine the contribution of FcγRIII to these physiological responses to IgG immune complexes.

FcR-mediated phagocytosis was assessed by the ability of TEM to internalize sheep red blood cells (SRBC) opsonized with IgG. (FIGS. 12A–12H). IgG2a opsonized RBC are bound and internalized preferentially by the high affinity FcγRI, while IgG1 and 2b are only bound and internalized by the low affinity receptors (Weinshank et al., 1988). As shown in FIG. 12A and E, macrophages from wild-type (+/+) mice displayed robust binding of IgG opsonized SRBCs of G1 and 2a subclasses. Heterozygous mice displayed identical binding (not shown) and IgG2b binding was comparable to IgG1 in all cases (not shown). These bound opsonized particles were efficiently internalized, as shown in 5B and 5F. Macrophages from homozygous mutant (−/−) mice bind IgG1-opsonized SRBC (SC), due to retained expression of FcγRII (FIGS. 10A–10C). This binding is completely blocked by mAb 2.4G2. These same macrophages failed to demonstrate IgG2a binding (5G), indicating an unexpected loss of FcγRI binding activity. This is not the result of loss of FcγRI a chain expression, since these macrophages express equivalent levels of mRNA for this chain, when compared to wild-type mice (data not shown). Rather it indicates a functional dependance of the high affinity FcγRI for γ chain either for facilitating surface expression or ligand binding for this receptor. Despite the efficient binding of SRBC to −/− macrophages through FcγRII, these cells fail to internalize such opsonized particles, indicating a more global defect in FcR mediated phagocytosis. Deletion of γ chain thus has a pleiotropic effect on macrophage FcR mediated ligand binding and phagocytosis beyond what might be expected by the loss of FcγRIII.

ADCC Activity, but not Natural Killing, in NK Cells was Severely Abrogated in FcRγ$^{n1}$ Mice Natural killing activity, as measured against the YAC-1 tumor target, was normal for wild-type and mutant NK cells either freshly isolated from the spleen or purified over glass wool and cultured in IL-2 for 7 days (FIG. 13A). The El-4 target is less sensitive to NK lysis in both wild-type and mutant cell preparations. Deletion of γ chain thus has no effect on natural killing of tumor targets, consistent with the evidence that receptors other than FcγRIII mediate this process. ADCC activity against TNP-derivatized and anti-TNP IgG1-coated EL-4 target, however, was markedly diminished in NK cells from γ-deficient mice, while wild-type NK cells showed clear ADCC activity against the same target cells; this ADCC activity was completely blocked by the monoclonal antibody 2.4G2 (FIG. 13B). These results indicate that ADCC activity is almost totally lost in NK cells in these mutant mice due to loss of functional FcγRIII expression.

Characterization of Mast Cell Functions

Mast cells were first sensitized with monoclonal mouse IgE and then triggered with monoclonal anti-mouse IgE antibody. Degranulation, ³H-serotonin release, IL-4 production and prostaglandin D₂ release of these cells were measured for wild-type as well as γ-deficient mice (FIGS. 14A-14D). As expected, degranulation and serotonin release from γ-deficient mast cells were only negligible above background, while +/+ mast cells responded well to IgE-crosslinking (FIG. 14A & B). Similarly, the amount of an IL-4-specific 267 bp cDNA fragment was markedly increased after stimulation of mast cells from wild-type mice (FIG. 14C). In contrast, mast cells from γ-deficient mice showed apparently no response to crosslinking stimulation. Finally, prostaglandin D₂ release into the culture supernatant was significantly reduced in mutant mast cells, as compared to wild-type cells (FIG. 14D). Thus, by several criteria, assessing early and late activation responses of mast cells to IgE crosslinking, the mutant mice fail to respond.

IgE-Mediated Anaphylaxis is Absent in FcRγ$^{n1}$ Mice

IgE mediated anaphylaxis is thought to be dependant upon FcεRI triggering of mast cells, although the role of other cell types and other IgE binding molecules to this in vivo response is debated. To address this question, mutant and wild-type mice were challenged in a passive cutaneous anaphylaxis (PCA) model. The characteristic increase in vascular permeability triggered by mast cell degranulation is readily visualized by Evans blue extravasation. Wild-type and heterozygous mice mount a prompt PCA reaction in response to IgE crosslinking. In contrast, homozygous deficient animals are unable to mount a PCA reaction.

Discussion

Gene targeting in embryonic stem cells was used to generate a mouse strain carrying a mutation in γ subunit of FcRs, a subunit also found associated with TCR/CD3. Mice homozygous for this mutation failed to express mRNA or protein for the γ subunit. Based on previous reconstitution studies in transfected cells, it was expected that this mutation would result in the loss of surface expression for FcγRIII and FcεRI. Since these receptors are restricted in their cell-type expression, antibody-dependant effector pathways involving mast cells, macrophages, neutrophils and NK cells would be expected to be affected. In addition, abnormalities in either T cell development or function might be manifested by these animals, resulting either from the loss of FcγRIII from an early thymocyte population or a requirement for γ chain as a component of TCR/CD3 in some T cells. Deletion of the homologous ζ chain does result in such T cell developmental abnormalities (Love et al., 1993). Homozygous γ-deficient mice are viable up to six months and fertile, demonstrating that the γ subunit is not required for normal mouse development.

In contrast with the absence of obvious developmental abnormalities, γ subunit-deficient mice clearly show several types of immunodeficiency, resulting from defects in FcR-mediated effector functions. While these experiments were undertaken to precisely define the role of each of these FcRs in antibody-mediated effector responses, study results revealed that these mice are more profoundly immunocompromised than could have been predicted from prior in vitro studies.

The data presented here reveal four marked differences between the mutant mice and their wild-type littermates. First, macrophages have lost their phagocytic activity against IgG-opsonized SRBC. Although homozygous mutant mice did exhibit significant binding capacity to SRBC opsonized with IgG1 and 2b subclasses of mouse immunoglobulin as assessed by a resetting assay, but they did not show any activity to ingest them, indicating that homozygous mutant mice still have FcγRII but this receptor's contribution to macrophage phagocytic function is lost due to γ-chain deletion. No evidence to date suggests that γ chain associates with this FcγRII (referred to as IIB), the only FcγRII gene found in the mouse and the only FcγRII gene conserved between mouse and man. IIB has been shown to undergo alternative splicing generating proteins with variant cytoplasmic domains (Ravetch, et al., 1986) which target the receptor to different intracellular compartments upon endocytosis of immune complexes (Miettinen, et al., 1989). Macrophages express the IIB2 form of this gene, which localizes to coated pits while B lymphocytes preferentially express IIB1. The failure of γ-deficient mice to mediate phagocytosis through IIB2 may suggest a functional coupling of this receptor to a common signalling subunit, or indicate that IIB2 in vivo functions only as an inhibitory receptor, as has been demonstrated for B cells. Distinguishing between these two alternatives is now in progress.

Second, functional expression of FcγRI is greatly diminished on macrophages from γ-deficient mice. This receptor binds IgG2a with high affinity and cannot be inhibited by a mAb directed against FcγRII and III, 2.4G2. Mutant macrophages fail to bind IgG2a coated SRBCs through this receptor, indicating a functional requirement for the γ subunit. Previous studies have demonstrated the ability of FcγRI to be expressed in heterologous cells, like COS-7, in the absence of other subunits (Allen and Seed, 1989). The cell surface molecule expressed on those transfected cells retains its ability to bind IgG2a. Thus, the failure of macrophages isolated from -deficient mice to bind IgG2a through FcγRI was unexpected. Since no antibody reagents exist which recognize this murine receptor, it cannot determine if γ chain is required for cell-surface expression of this receptor in macrophages, or is required for ligand binding when expressed on its native cell. The observation that γ chain associates with human FcγRI in a myelomonocytic cell line, suggests that the transfection results in COS-7 cells do not mimic the native receptor in macrophages. Since FcγRI is functionally absent from the γ-deficient cells, the net result of γ deletion is an animal whose macrophages are unable to mediate phagocytosis of IgG opsonized particles. These mice will be invaluable in determining the contribution of phagocytosis of IgG opsonized pathogens in the normal immune response.

Third, freshly isolated or IL-2 stimulated NK cells from γ-deficient mice have lost the ability to mediate ADCC, while retaining natural cytolytic activity against tumor targets like YAC-1. This defect in ADCC is the result of the loss of expression of FcγRIII, since NK cells do not express any of the other known FcRs. These results eliminate any possibility of other surface components of NK cells substituting for FcγRIII in ADCC. The absolute requirement for γ chain expression in the mouse is to be contrasted with the situation in human NK cells, where ζ chain can efficiently substitute for γ chain. Thus, mice can assemble only two types of FcγRIII—αγ$_2$ and αγζ while human NK cells have been shown to possess an additional receptor complex composed of αζ$_2$. No functional differences have been observed between human and mouse NK cells in mediating ADCC, suggesting that the role of ζ chain is not critical to this response. No differences in the number of NK cells or their distribution was observed in these mutant mice, further indicating that the FcγRIII$^+$ early thymocyte population defined previously (Rodenwald, et al., 1992) is not required for NK cell development.

Fourth, mast cells from γ-deficient mice have lost their response to IgE crosslinking and fail to mediate the classic allergic responses of mast cells. These cells are do not degranulate, secrete prostaglandin D$_2$, induce IL-4 synthesis or release serotonin upon IgE stimulation and crosslinking. When these mice are challenged in a passive cutaneous anaphylaxis assay, they fail to mount a response, further indicating the significance of this receptor in mediating the anaphylaxic response. These functional defects in mast cells are likely to be the direct result of the loss of FcεRI expression on those cells. The possibility cannot be rule out that concomitant loss of FcγRIII from mast cells may contribute to this deficiency, it is unlikely to play a significant role since that receptor has been shown to mediate only low affinity binding to IgE. That the γ chain may contribute to these mast cell defects in a pleiotropic manner, affecting receptors other than FcεRI similar to what has been observed in macophages, remains a possibility, which can be resolved by comparing FcRγ$^{n1}$ mice with those whose loss of FcεRI results from the deletion of the ligand binding α subunit of this receptor. In those mice, the same functional defects are seen (Kinet, personal communication), thus firmly establishing the essential role of FcεRI in mediating mast cell responses to IgE and in vivo anaphylaxis.

In marked contrast to the defects in innate immunity resulting from FcR perturbation, T cell development appears to be grossly normal. The same populations of cells were observed in thymocytes and peripheral T cells from 2 week or 10 week old mice in the γ-deficient animals and their wild-type littermates. This chain, while found associated with TCR/CD3 in some populations of T cells, is clearly not critical for normal T cell development, in contrast to what has been reported in ζ-deficient animals. This preliminary analysis of T cell populations in these mutant mice further suggests that the dominant FcγRIII$^+$ population of early thymocytes (day 14.5–16.5), is not essential for progression through the normal T cell developmental program. Whether specific defects in T cell populations which appear to use the γ chain exclusively are found in these animals remains to be determined.

These mice therefore will enable studies to be performed evaluating the contribution of IgG and IgE triggered effector responses to a variety of pathogens and will aid in further defining the role of this subunit in both T cell and effector cell pathways.

EXPERIMENTAL PROCEDURES

Construction of the Targeting Vector pFCRγP

Phage clones spanning the mouse FcR γ subunit gene were isolated from the genomic library of 129/Ola origin (te Riele et al., 1990) using a mouse γ subunit cDNA probe (Ra et al., 1989). EcoRI fragments were subcloned into plasmid vectors, and exons and flanking sequences were partially sequenced. The sequences determined were found to be identical to that described by Ra, et al., 1989. The localization of each exon was determined by polymerase chain reaction using specific primers for exons 1 and 2, or by comparing the genomic sequences with the restriction map. The targeting vector pFCRγP was made by subcloning a 1.1 kb XhoI-SalI fragment containing 5' upstream sequences, exon 1 and 5' part of exon 2 of the murine γ subunit gene into the XhoI site of pMC1-neo (Stratagene) to create pMC1-γ-neo. A 3.9-kb SalI fragment spanning the 3' part of exon 2 to sequences 5' of exon 5 of the γ gene was subcloned into the SalI site of pMC1-γ-neo to create pMC1-neo-FCRg. The resulting insert was integrated into the XhoI site of pIC19R-MC1tk (Marsh et al., 1984; Thomas and Capecchi, 1987) to give pFCRγP as shown in FIG. 8A. The vector was linearized at a unique ClaI site within the polylinker of the plasmid.

Monoclonal Antibodies

The following primary antibodies were used in this study: 2.4G2 (anti-FcgRII/III, Unkeless, 1979); TIB191 (anti-TNP IgG1 from the ATCC); IGEL (anti-TNP IgE from the ATCC); anti-SRBC IgG2a (S-S.1), IgG2b(N-S.8.1), IgG3 (NS.7)all obtained from the ATCC; RM4-5 (anti-CD4), 53–6.7 (anti-CD8), H57-597 (anti-TCRαβ), DNL-1.9 (anti-B220), RB6-8C5 (anti-granulocyte), 145-2C11 (anti-CD3) all from Pharmingen; M1/70 (anti-Mac-1), 30-H12 (anti-Thy1.2) from Boehringer Mannheim; 4D11 (anti-LGL-1), kindly provided by Dr. Llewellyn Mason; Ack2 (anti-ckit) kindly provided by Dr. S. Nishikawa.

Cell Cultures and Transfections

The ES cell line E14 (Hooper, et al., 1987) was maintained in Dulbecco's modified Eagle's Medium (DMEM) containing 15% heat-inactivated fetal calf serum (FCS), 0.1 mM 2-mercaptoethanol, 2 mM glutamine, 0.1 mM non-essential amine acids (Gibco-BRL), and 1000 U/ml recombinant leukemia inhibitory factor (ESGRO; Gibco-BRL) on feeder layers from primary embryonic fibroblasts in a 37° C., 5% $CO_2$ humidified incubator. ES cells ($1\times10^7$) in 600 μl of phosphate buffered saline (PBS; $Ca^{2+}$ and $Mg^{2+}$ free) containing 50 μg of linearized targeting vector were electroporated at 800 V with a 3 μF capacitance in a 0.4 cm wide cuvette (Bio-Rad Gene Pulser). After approximately 10 min, the cells were plated on 60 mm dishes with neo-resistant embryonic fibroblast feeder layer cells. The selection was started 24 hr later with 300 μg/ml G418 alone or together with 0.2 μM FIAU. Colonies were picked and transferred to individual wells of 96-well dishes. Each clone was subsequently transferred to 1 well of 24-well dishes and grown to confluence. At this point, one-third of each clone was frozen at −80° C., and the remainder was used to prepare DNA for Southern analysis.

Embryo Injection and Mouse Breeding

C57BL/6 blastocysts (3.5 days post coitum) were flushed from the uterus of naturally mated females in DMEM containing 10% FCS. ES cells (10–20 cells) from each clone were microinjected into the blastocoele of each blastocyst, which were reimplanted into the uterus of day 2.5 pseudopregnant foster mothers. The E14 ES cell line was originally derived from an XY blastocyst of the 129/Ola strain (Hooper et al., 1987). Chimeric animals were then detected by the presence of agouti patches on the non-agouti (black) fur and were mated with non-agouti C57BL/6 animals. Germline transmission was scored by the presence of agouti offspring in the litter. Agouti $F_1$ offspring from chimera and C57BL/6 crosses were genotyped by genomic blotting of DNA prepared from tail biopsies. Animals heterozygous for the FcRγ$^{n1}$ mutation were crossed to heterozygous siblings. $F_2$ offspring from these crosses were genotyped by genomic blotting to distinguish heterozygotes from homozygotes.

Southern Blot Analysis and Genotyping of Progeny

DNA was isolated from the E14 cell line and from each of the G418- and FIAU-double resistant ES cell clones. DNA was subjected to restriction enzyme digestion with BglI and EcoRI. Each digest was fractionated on a 0.7% agarose gel, transferred to GeneScreen (DuPont), and hybridized with 0.5 kb SacI fragment (FIGS. 8A–8F). In addition, blots were also screened with a neo, HSV-tk probe, 0.34 kb SacI-SalI fragment(probe C) and 0.33 kb HindIII-EcoRI fragment (probe B) from γ subunit genomic clone (FIGS. 8A–8F). For Southern analysis for genotyping progeny, DNA was prepared from tail tips of weaned mice at 3-weeks of age. Genomic DNA was digested with BglI and EcoRI and subjected for gel electrophoresis and transferred as above and probed with a 0.42 kb SalI-EcoRI γ subunit cDNA fragment (Ra, et al., 1989)

Flow Cytometric Analysis

Single-cell suspensions from bone marrow, spleen, thymus and peritoneal cavity of mice from 2 weeks to 3 months of age were prepared as described below. Aliquots of $10^6$ cells were stained for 30 minutes at 40° C. with FITC or PE conjugated antibodies as noted in the text. Unconjugated monoclonal antibodies were revealed by FITC- or PE-conjugated goat anti-mouse IgG F(ab). Cells were washed twice in PBS containing 1% BSA and 0.1% sodium azide after each incubation and fixed in PBS, 0.1% sodium azide and 1% formaldehyde. Fluorescence intensity was measured on a FACScan flow cytometer using FACScan research software (Becton, Dickinson and Co.). Dead cells were eliminated from the analysis on the basis of forward and sideways light scatter.

Preparation of IL-2-Activated Splenocytes

Spleens of wild-type and mutant mice were removed aseptically and crushed with the hub of a syringe and a stainless steel tea filter in medium (NK medium) consisting of RPMI1640 with 0.1 mM nonessential amino acids and 1 mM sodium pyruvate, $5\times10^{-5}$M 2-mercaptoethanol, 100 U/ml penicillin, 100 μg/ml streptomycin, 2 mM glutamine, and 10 heat-inactivated FCS (HyClone). The whole spleen cell suspension was passed through stainless mesh, the erythrocyte lysed by Tris/$NH_4Cl$ and the remaining cells centrifuged and washed with NK medium and then passed through a nylon wool column. The nylon-passed cells were resuspended at $5\times10^6$ cells/ml and cultured for 4 to 7 days in NK medium supplemented with 1000 U/ml recombinant IL-2 (Gibco-BRL) and 1 μg/ml indomethacin (Sigma). Fresh medium was added at a 1:1 volume every 3- to 4-days. The cells were harvested at the end of the incubation, washed and used for the flow cytometric analysis or $^{51}$Cr-release cytotoxicity test.

RT-PCR Analysis

Total RNA was prepared from single cell suspensions according to Chomczynski and Sacchi (1987) using RNAzol (Cinna/Biotecx Laboratories, Houston, Tex.). First-strand cDNA synthesis from total RNA derived from $5\times10^5$ cells was performed using SuperScript reverse transcriptase (Gibco-BRL) and oligo(dT) primers. Oligonucleotide primers complementary to regions of the exons 1 and 5 (FIGS. 8A–8F) ) were incubated with one-twentieth of reverse transcribed RNA mixture and subjected to 30 cycles of amplification using standard PCR protocols. PCR products were analyzed on a 7.5% polyacrylamide gel and visualized with ethidium bromide staining. Primer sequences for PCR amplification were as follows: 5'-GAGATCATCGG CATTTTGAAC-3' (SEQ ID NO: 10) and 5'-CTTG GACTCATTCATGGTGCA-3' (SEQ ID NO: 11) for IL-4 cDNA (Noma, et al., 1986, Lee et al., 1986) generating a 267 bp fragment; 5'-CCAGGATGATCTCAGCCG-3' (SEQ ID NO: 12) and 5'-ACAGTAGAGTAGGGTAAG-3' (SEQ ID NO: 13) for γ subunit cDNA corresponding to exons 1 and 2 generating a 137 bp fragment; 5'-CTTCCTCGTGCTTT ACGGTATC-3' (SEQ ID NO: 14) and 5'-CTTCAGAGTC TCATATGT-3' (SEQ ID NO: 15) for neo-γ-subunit fusion cDNA (FIGS. 9A–9C) generating a 197 bp fragment.

IL-4 mRNA Induction and Prostaglandin $D_2$ Release from Mast Cells

Bone marrow cells were flushed out of the femurs and tibias of mice using a 23-gauge needle, resuspended and then washed in PBS. The cells were cultured in MC medium consisting of 10% WEHI-3A culture supernatant or recombinant IL-3, 10% heat-inactivated FCS, RPMI1640 medium, 4 mM glutamine, non-essential amino acids, $10^{-5}$M 2-mercaptoethanol, 1 mM sodium pyruvate, 100 U/ml penicllin, 100 μg/ml streptomycin, replacing the medium every 3 to 4 days. The bone-marrow derived, IL-3 induced mast cells were suspended at $5 \times 10^5$ cells/ml in MC medium and mixed with ¼ volume of culture supernatant of mouse anti-TNP IgE-producing hybridoma, IGEL, at 37° C. for 18 hr in 95% air-5% $CO_2$. The cells were washed, resuspended at $4 \times 10^5$ cells/ml and divided into 24-well culture plates at 1 ml/well with anti-mouse IgE monoclonal antibody at 10 μg/ml. The cells and culture supernatant were collected at various time intervals and stored at –80° C. until use. The cell pellet was used for RT-PCR assay to determine IL-4 mRNA induction (Plaut, et al., 1989), and culture supernatant was subjected for the radioimmunoassay of prostaglandin $D_2$ (Amersham).

Degranulation and $^3$H-serotonin release assay was performed using monoclonal mouse IgE as sensitizing antibody and anti-mouse IgE as stimulating antibody as previously described (Daeron, et al., 1992). Briefly, BM derived mast cells ($1 \times 10^6$) were incubated overnight with mouse IgE monoclonal Ab at 4 μg/ml and washed. In the serotonin release assay, they were incubated with 5 $\mu C_1/ml^3$H-serotonin for 14 hr at 37° C. and washed extensively. Cells were then stimulated with anit-mouse IgE monoclonal Ab at 10 μg/ml and incubated for 60 minutes. Maximal release was determined using A23187 as a nonspecific ionophore.

Macrophage Cultures

Mice were injected intraperitoneally with 1 ml of 5% thioglycollate, and peritoneal exudate cells were harvested 3 days later. The cells were suspended in alpha-modified MEM (α-MEM) supplemented with 10% heat-inactivated FCS, to a concentration of $1 \times 10^6$ cells/ml. They were plated in 24-well culture plates at 1 ml/well and incubated for 6 hr at 37° C. in 95% air-5% $CO_2$. Following this, the nonadherent cells were removed by rinsing the monolayers with PBS and the thus purified macrophages were subjected to the assays described below.

Preparation of Opsonized Erythrocytes, Rosetting and Phagocytosis Assays

Sheep red blood cells (SRBC; Gibco) were first derivatized with the hapten trinitrophenyl (TNP) as described (Rodewald, et al., 1992). They were then incubated with the culture supernatant of TIB191 (anti-TNP IgG1). Alternatively, intact SRBC were incubated with culture supernatant of hybridomas S-S.1,N-S.8.1 and N-S.7 (anti-SRBC IgG2a, 2b, and IgG3, respectively). These antibodies for opsonization were used at non-agglutinating titers. Opsonized SRBC were added to macrophage monolayers prepared as described above and incubated either for 30 minutes at 40° C. for determination of rosetting or for 90 min at 37° C. in 95% air-5% $CO_2$, and then washed extensively with PBS for determination of phagocytosis. For estimation of phagocytosis activity, they were further washed in distilled water to hypotonically lyse extracellularly rosetted SRBC. The cells were then fixed in 0.25% glutaraldehyde and were photographed or counted for the number of rosetted and phagocytic cells using phase contrast microscopy.

Cytotoxicity Assays

Cytotoxicity assays using IL-2-induced splenic NK cells were performed in 96-well U-bottom plates (Corning) according to Rodewald et al. (1992). Target cells were labeled with $^{51}$Cr (DuPont-NEN, Boston, Mass.) at 100 μCi per $10^6$ cells for 1 hr at 37° C., washed twice, and used in a standard 4 hr $^{51}$Cr-release assay with $5 \times 10^3$ target cells per well. Maximum isotope release was measured by incubating the target cells in 1% Nonidet P-40. Spontaneous release was measured by incubation of the target cells in culture medium alone. Results are expressed as the mean of percent-specific lysis of triplicate samples (with S.D, $\leq$10%). NK activity was evaluated using various effector:target ratios against either the conventional NK target cell line YAC-1 (murine B lymphoma) or EL-4 (murine thymoma). For ADCC assays, EL-4 cells were $^{51}$Cr-labeled, treated with 30 mM 2,4,6-trinitrobenzene sulfonic acid (ICN Biochemicals) in PBS for 5 min at room temperature, washed and incubated for 30 min with an anti-TNP antibody (IgG1, clone 1B7.11 [ATCC, Rockville, Md.]) using culture supernatant (1:128 final concentration). Cells were washed extensively, and used as targets as above. For the blocking of FcγRII/III function, effector NK cells were incubated with 2.4G2 at 10 μg/ml for 30 min prior to the cytotoxicity assays: the blocking antibody was not removed before the assay. TNP derivatization or treatment with an anti-TNP antibody had no effect on spontaneous release of radioactivity.

Immunoblot Analysis $4 \times 10^6$ cells of thioglycollate-elicited peritoneal macrophages, IL-3-induced bone marrow mast cells and IL-2-induced splenic NK cells were suspended in 30 μl of gel-loading buffer, and 15 μl ($2 \times 10^5$ cell equivalents) was loaded on a 15% SDS-polyacrylamide gel. Following electrophoresis, protein was transferred to nitrocellulose for 18 hr at 20 V, and the blot was blocked 1 hr in PBS containing 5% non-fat milk powder and 0.1% Tween 20. FcR γ subunit was detected by incubating the blot first with the rabbit anti-mouse γ chain antiserum (Kurosaki and Ravetch, 1989), then washed extensively in PBS containing 0.1% Tween 20, and incubated with horseradish peroxidase-conjugated anti-rabbit antibody in PBS plus 0.1% Tween 20. After washing excess antibody away, the filter was developed using the Enhanced Chemiluminescence (ECL) detection system (Amersham).

Passive Cutaneous Anaphylaxis

Eight week old γ-deficient mice and their littermate controls were lightly anesthetized and injected intradermally in the left ear with 20 ng of monoclonal mouse anti-DNP IgE (Sigma) diluted in 20 μl DMEM; the right ear was injected with DMEM alone. The next day, the mice were injected i.v. with 100 μg DNP-human serum albumin (Sigma) in 100 μl 0.9% NaCl; 1% Evans blue dye (Sigma) was added to permit visual localization of increased vascular permeability. The reaction was quantitated at 60 minutes post injection.

References for Third Series of experimentEs

Alcaraz, G., Kinet, J.-P., Liu, T. Y., and Metzger, H. (1987) Further characterization of the subunits of the receptor with high affinity for immunoglobulin E. Biochemistry 26 2569–2575.

Allen, J. M. and Seed, B. (1989) Isolation and expression of functional high affinity Fc receptor complementary DNAs, Science, 243, 378.

Askenase, P. W., and Heyden, B. J. (1974) Ctyophilic antibodies in mice contact-sensitized with oxazolone. Immunochemical characterization and preferential binding to a trypsin-sensitive macrophage receptor. Immunol. 27 563–576.

Beaven, M. A., and Metzger, H. (1993) Signal transduction by Fc receptors: the FcεRI case. Immunol. Today 14 222–226.

Brooks, D. G., Qiu, W. Q., Luster, A. D. and Ravetch, J. V. (1989) Structure and expression of human IgG FcRII (CD32). J. Exp. Med. 170 1369–1386.

Chomczynski, P., and Sacchi, N. (1987) Single step method of RNA isolation by acid quanidinium-thiocyanate-phenol-chloroform extraction. Anal. Biochem. 162 156–159.

Coolidge, B. and Howard, R. (1979) in Animal Histology Procedures, NIH publication #80–275 p. 137.

Daeron, M., Bonnerot, C., Latour, S., and Fridman, W. H. (1992) Murine recombinant FcγRIII but not FcγRII, trigger serotonin release in rat basophilic leukemia cells. J. Immunol. 149 1365–1373.

Diamond, B., Bloom, B. R., and Scharff, M. D. (1978) The Fc receptors of primary and cultured phagocytic cells studied with homogeneous antibodies. J. Immunol. 121 1329–1333.

Ernst, L. K. Duchemin, A. M. and Anderson, C. L. (1993) Association of the high affinity receptor for IgG with the gamma subunit of the IgE receptor PNAS 90, 6023.

Heusser, C. H., Anderson, C. L., and Grey, H. M. (1977) Receptors for IgG: subclass specificity of receptors on different mouse cell types and the definition of two distinct receptors on a macrophage cell line. J. Exp. Med. 145 1316–1327.

Hooper, M., Hardy, K., Handyside, A., Hunter, S. and Monk, M. (1987) HPRT-deficient (Lesch-Nyhan) mouse embryos derived from germline colonization by cultured cells. Nature 326 292–295.

Kurosaki, T., Gander, I., and Ravetch, J. V. (1991) A subunit common to an IgG Fc receptor and the T-cell receptor mediates assembly through different interactions. Proc. Natl. Acad. Sci. USA 88 3837–3841.

Kurosaki, T., Muta, T., Sanchez, M., Misulovin, z., Nussenzweig, M. and Ravetch, J. V. (1993) A 13 amino acid motif in the cytoplasmic domain of FcγRIIB modulates B cell receptor signalling. Nature, in press.

Kurosaki, T., and Ravetch, J. V. (1989) A single amino acid in the glycosyl phosphatidylinositol attachment domain determines the membrane topology of FcγRIII. Nature 342 805–807.

Kuster, H., Thompson, H., and Kinet, J.-P. (1990) Characterization and expression of the gene for the human Fc receptor γ subunit. J. Biol. Chem. 265 6448–6452.

Lanier, L. L., Yu, G., and Phillips, J. H. (1989) Co-association of CD3ζ with a receptor (CD16) for IgG Fc on human natural killer cells. Nature 342 803–806.

Lee, F. (1986) Isolation and characterization of a mouse interleukin cDNA clone that expresses B-cell stimulating factor 1 activities and T cell and mast cell stimulating activities. Proc. Natl. Acad. Sci. USA 83 2061–2065.

Love, P. E., Shores, E. W., Johnson, M. D., Tremblay, M. L., Lee, E. J., Grinberg, A. , Huang, S. P., Singer, A., and Westphal, H. (1993) T cell development in mice that lack the ζ chain of the T cell antigen receptor complex. Science 261 918–921.

Marsh, J. L., Erfle, M., and Wykes, B. J. (1984) The pIC plasmid and phage vectors with versatile cloning sites for recombinant selection by insertional inactivation. Gene 32 481–485.

Mason, L. et al. (1989) in Natural Killer Cells and Host Defense, 5th Int. NK Cell Workshop ed. Ades, E. and Lopez, C. Basel, Karger pp. 33–38.

Matsuda, H. Watanabe, N., Kiso, Y., Hirota, S., Ushio, H., Kannan, Y., Azuma, M., Koyama, H., and Kitamura, Y. (1990) Necessity of IgE antibodies and mast cells for manifestation of resistance against larval *Haemophysalis longicornis* ticks in mice. J. Immunol 144 259–262.

Mercep, M., Weissman, A. M., Frank, S. J., Klausner, R. D., and Ashwell, J. D. (1990) Activation-driven pro-grammed cell death and T cell receptor ζγ expression. Science 246 1162–1165.

Miettinen, J. M., Rose, J. K. and Mellman, I. (1989) Fc receptor isoforms exhibit distinct abilities for coated pit localization due to cytoplasmic domain heterogeneity, Cell 58, 317.

Nathan, C. F., Murray, H. W., and Cohn, Z. A. (1980) The macrophage as an effector cell. N. Eng. J. Med. 303 622–626.

Noma, Y. (1986) Cloning of cDNA encoding the murine IgG1 induction factor by a novel strategy using SP6 promoter. Nature 319 640–646.

Parker, C. W. (1987) Lipid mediators produced through the lipoxygenase pathway. Annu. Rev. Immunol. 5 65–84.

Perussia, B., Tutt, M. M. Qiu, W. Q., Kuzel, W. A., Tucker, P. W, Trinchieri, G., Bennet, M., Ravetch, J. V. and Kumar, U. (1989) Murine natural killer cells express functional Fcγ Receptor II encoded by the FcγRα gene. J. Exp. Med. 170 73–86.

Plaut, M., Pierce, J. H., Watson, C. J., Janley-Hyde, J., Nordan, R. P., and Paul, W. E. (1989) Mast cell lines produce lymphokines in response to cross-linkage of FcεRI or to calcium ionophores. Nature 339 64–67.

Qiu, W. Q., de Bruin, D., Brownstein, B. H., Pearse, R., and Ravetch, J. V. (1990) Organization of the human and mouse low-affinity FcγR genes: duplication and recombination. Science 248 732–735.

Ra, C., Jouvin, M.-H., Blank, U., Kinet, J.-P. (1989) A macrophage Fcγ receptor and the mast cell receptor for IgE share an identical subunit. Nature 341 752–754.

Ra, C., Jouvin, M.-H. E., Kinet, J.-P. (1989) Complete structure of the mouse mast cell receptor for IgE (FcεRI) and surface expression of chimeric receptors (rat-mouse-human) on transfected cells. J. Biol. Chem. 264 15323–15327.

Ravetch, J. V., Anderson, C. L. (1990) in Fc receptors and the action of antibodies chapter VI FcγR family: proteins, transcripts, and genes. ed. H. Metzger.

Ravetch, J. V., and Kinet, J.-P. (1991) Fc receptors. Annu. Rev. Immunol. 9 457–492.

Ravetch, J. V., Luster, A. D., Weinshank, R., Kochan, J., Pavlovec, A., Portnoy, D. A., Hulmes, J., Pan, Y.-C. E. and Unkeless, J. C. (1986) Structural heterogeneity and functional domains of murine immunoglobulin G Fc receptors. Science 234 718–725.

Rodewald, H.-R., Moingeon, P., Lucich, J. L., Dosiu, C., Lopez, P., and Reinherz, E. L. (1992) A population of early total thymocytes expressing FcγRII/III contains precursors of T lymphocytes and natural killer cells. Cell 69 139–150.

Romeo, C., and Seed, B. (1991) Cellular immunity to HIV activated by CD4 fused to T cell of Fc receptor polypeptides. Cell 64 1037–1046.

Stuart, S. G., Simister, N. E., Clarkson, S. B., Shapiro, M., and Mellman, I. (1989) The low affinity Fc receptor for human IgG (hFcRII) exists as multiple isoforms. EMBO J. 8 3657–3666.

te Riele, H., Maandag, E. R., Clarke, A., Hooper, M., and Bens, A. (1990) Consecutive inactivation of both alleles of the pim-1 proto-oncogene by homologous recombination in embryonic stem cells. Nature 348 649–651.

Thomas, K. R., and Capecchi, M. R. (1987) Site-directed mutagenesis by gene targeting in mouse embryo-derived stem cells. Cell 51 503–512.

Uher, F. Lamers, M. C., and Dickler, H. B. (1985) Antigen-antibody complexes bound to B-lymphocyte Fcγ receptors regulate B-lymphocyte differentiation. Cell. Immunol. 95 368–379.

Unkeless, J. C. (1979) Characterization of a monoclonal antibody directed against mouse macrophage and lymphocyte Fc receptors. J. Exp. Med. 150 580–596.

Weinshank, R. L., Luster, A. D., and Ravetch, J. V. (1988) Function and regulation of a murine macrophage-specific IgG Fc receptor, FcγR-α. J. Exp. Med. 163 1909–1925.

Weissman, A. M., Baniyash, M., Hou, D., Samelson, L. E., Burgess, W. H., and Klausner, R. D. (1989) Molecular cloning of the zeta chain of the T cell antigen receptor. Science 239 1018–1021.

Wirthmueller, U., Kurosaki, T., Murakami, M. S. and Ravetch, J. V. (1992) Signal transduction by FcγRIII (CD16) is mediated through the γ chain. J. Exp. Med. 175 1381–1390.

Fourth Series of Experiments

SUMMARY

Antibody-antigen complexes are potent initiators of the inflammatory response and thus are central to the pathogenesis of autoimmune tissue injury. The canonical model by which immune complexes stimulate the inflammatory cascade holds that complement binds to and is activated by immune complexes; this then triggers a proteolytic cascade which culminates in edema, hemorrhage, polymorphonuclear cell infiltration and subsequent tissue damage. This pathway has been reinvestigated using the classical experimental model of inflammation, the Arthus reaction, in a murine strain in which a gene required for Fc receptor expression has been deleted (FcRγ$^{-1}$). Unexpectedly, these mice are unable to mount an effective inflammatory response when challenged with antibody-antigen complexes, despite an intact complement cascade and normal inflammatory responses to other stimulatory agents. Based on these results, a new model of immune complex-triggered inflammation is proposed in which the inflammatory reaction is initiated by cell-bound Fc receptors and is then propagated and amplified by released cellular mediators and activated complement. The identification of Fc receptor engagement as a critical step in the initiation of immune complex-mediated inflammation offers a new mechanistic paradigm of the inflammatory cascade and provides further confirmation for treating immunological injury, such as inflammation, allergy and autoimmune disease, by inhibiting the interaction of antibody-antigen complex with Fc receptors.

A strain of mice genetically deficient in the γ-subunit of the Fc receptor complex (10) has been recently developed, thereby eliminating the expression of FcγRIII and the high affinity receptor for IgE, FcεRI, and functionally limiting the expression of FcγRI. In vitro studies have demonstrated that macrophages from these mice are unable to phagocytose antibody-coated targets and that NK cells fail to mediate ADCC, consistent with a pleitropic defect in immune complex-triggered effector responses. In vivo, the loss of FcεRI results in animals unable to mount cutaneous or systemic anaphylactic responses to IgE triggered mast cell activation.

This genetically defined strain of mice has been used to evaluate the role of specific Fc receptors in the Arthus reaction. When challenged with IgG immune complexes, these animals mount a markedly diminished inflammatory reaction, despite a normally functioning complement system. Concurrent complement depletion in the Fc deficient mice completely abrogates the mild residual response. These unexpected results indicate that complement, long thought to be the key initiator of immune complex-triggered inflammatory responses, is a necessary, but not sufficient component of this cascade. Engagement of Fc receptors by immune complexes on the surface of effector cells is an early and critical step in this physiologically significant reaction.

The Arthus Reaction. Mice deficient for the γ chain of FcR (−/−), along with heterozygous (+/−) or wild-type (+/+) littermates, were injected intravenously with 20 mg/kg chicken egg ovalbumin (OVA), followed by intradermal injections of either rabbit α-ovalbumin IgG (Rb α-OVA), preimmune rabbit IgG or buffer alone, as previously published (11). The animals were sacrificed at 2, 4, 8 and 12 hours post challenge, and the injected skin was removed and examined histologically for the three hallmarks of inflammation—edema, hemorrhage and neutrophil infiltration. As seen in FIGS. 15A–15D, the skin from the −/− mouse shows a dramatic reduction in these parameters when compared with its +/+ counterpart; the reaction in +/− vs. +/+ was similar both qualitatively and quantitatively (not shown). Consistent with numerous previous studies of the reverse passive Arthus reaction (2, 3, 5, 6, 7, 8), in the absence of specific antibody to ovalbumin, little or no detectable inflammatory reaction was observed (not shown). The residual response seen is likely to be the result of non-specific tissue trauma or direct complement activation, since it is independent of the formation of immune complexes and observed in response to normal rabbit serum (not shown). As shown below, this residual response is eliminated by depletion of complement with cobra venom factor.

Blinded histologic scoring for a series of at least 30 skin sections in each group on a scale of 1+ to 4+ revealed a consistent and parallel reduction of all three parameters in the −/− vs +/+ mice at all time points measured; edema peaked at two to four hours, whereas hemorrhage and neutrophil infiltration were maximal at 8 hours, consistent with previously reported results (11).

The edema was further quantitated both visually, using Evans Blue, and with intravenously injected $^{125}$I-bovine serum albumin, which allows direct measurement of the volume of extravasated serum in the inflammatory lesion and which was more sensitive at later time points.

FIGS. 9A–9C, left, shows a representative 2 hour experiment quantitating total edema. On the right are photographs (+/+, top; −/−, bottom) of inverted skin samples at this time point; both show the early and distinct difference in edema formation between the −/− and the +/+ mice.

Hemorrhage was quantitated macroscopically by measuring the size of the purpuric spot in inverted skin sections. FIG. 17A, left, shows the numerical values of hemorrhage seen during a representative 8 hour experiment, and on the right are photographs of the inverted skin from a similar experiment. As can be seen, there are dramatic differences in both the size and intensity of the hemorrhagic lesions; these differences were also present at 4 and 12 hours (not shown).

Figure 18:
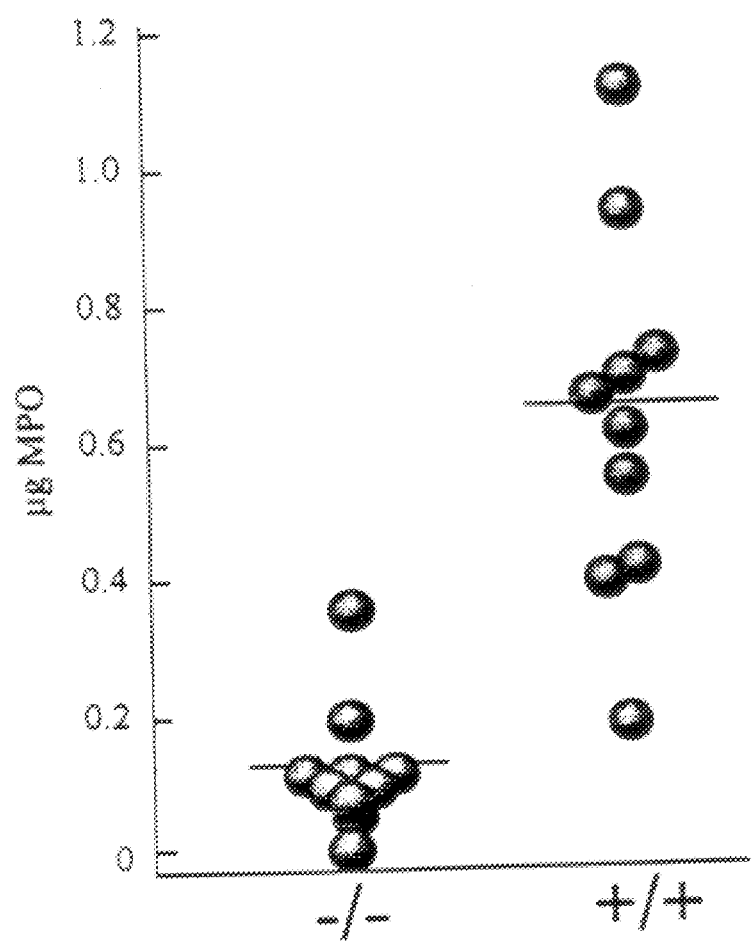

Because myeloperoxidase (MPO) is an enzyme present in abundance in the primary granules of neutrophils (and to a very minor extent in myeloid cells) its calorimetric measurement has been used to accurately quantitate neutrophils in both tissues and fluids (12). After verifying that the myeloperoxidase content of −/− and +/+ neutrophils was not significantly different, myeloperoxidase was extracted from injected areas of skin and quantitated using purified MPO as a standard. The MPO values from a representative 8 hour experiment are displayed in FIG. 18 and demonstrate the substantial difference between the −/− and +/+ mice, which was present at similar, albeit somewhat reduced, values at 4 and 12 hours as well.

The lack of Arthus response in the −/− mice was not due to a lag in kinetics, since minimal inflammation was seen at up to 24 hours. In addition, the differences seen were not dependent on type of antibody used. Purified mouse monoclonal IgG2a to TNP, known to elicit an attenuated inflammatory response relative to heterologous antibody, nonetheless showed a detectable and consistent deficit in the −/− mice. In contrast, the IgG3 subclass of antibody, which does not interact with FcγRI, II or III elicited the expected mild and indistinguishable response in the two mouse strains.

To determine if the complement system is intact in the −/− mice, total hemolytic complement levels were determined with the use of sheep red blood cells (SRBC) coated with rabbit anti-SRBC antibodies. Both +/+ and −/− animals had comparable and insignificantly different amounts of hemolytic complement, averaging 82±30 and 187±76 U/ml, respectively. The expression and function of the C3bi receptor, CR3, was characterized on −/− and +/+ macrophages. FACS analysis of macrophages derived from these two populations of mice demonstrated identical levels of CR3 expression. Similarly, SRBCs opsonized with C3bi were internalized normally by both +/+ and −/− macrophages. Consistent with these observations, the complement cascade was able to function normally in vivo. Intradermal injection of zymosan, which activates complement independently of immune complexes, through the "alternative pathway", showed vigorous and indistinguishable inflammatory responses. The inflammatory deficit displayed by the −/− mice can therefore be attributed to the lack of Fc receptors in these animals.

These studies consistently demonstrated that FcR deficient mice have substantially diminished reverse passive Arthus reactions in response to Rb α-OVA/OVA immune complexes. The lack of response in the −/− mice was not due to a lag in the kinetics of the response, since animals sacrificed at up to 24 hours still revealed minimal evidence of inflammation (not shown). In addition, the differences in inflammatory response were not dependent on the antibody used. Purified monoclonal mouse IgG2a anti-TNP, known to elicit an attenuated inflammatory response relative to heterologous antibody (7), nonetheless showed a detectable and consistent deficit in the −/− mice, as seen in FIGS. 19A and 19B. In contrast, the IgG3 subclass of antibody does not interact with FcγRI, II or III (7, 13) and would therefore be expected to elicit an equivalent response in the two mouse strains. As shown in FIG. 20A, left, −/− mice responded to IgG3 immune complexes with a mild inflammatory response indistinguishable from the +/+ littermates (not shown).

Other Inflammatory Parameters. Based on the results presented here, Fc receptor engagement by immune complexes is a critical step in the initiation of an antigen-antibody mediated inflammatory response. Since complement activation has been thought to be the key step in the initiation of the Arthus reaction, and since a defective complement system in the −/− mice is an alternative explanation for the results obtained, experiments to document an intact complement system were performed. First, total hemolytic complement levels were determined in −/− and +/+ mice, using sheep RBC's sensitized with rabbit anti-SRBC antibodies as targets (14). Both +/+ and −/− animals had comparable levels of hemolytic complement, averaging 82±30 and 187±76 U/ml, respectively. The ability of the complement cascade to function in vivo was next determined by challenging these animals with intradermal zymosan, which activates complement independent of immune complexes, via the "alternative pathway" (15). As seen in FIG. 20B, right, zymosan induced a dramatic inflammatory response in the −/− mice, which was indistinguishable from that of the +/+ mice (not shown). The data presented in FIG. 20 indicate that inflammatory responses to stimuli which do not interact with Fc receptors, like zymosan or mouse IgG3, are intact in the −/− mice. The defect displayed by these animals in mounting an inflammatory response to IgG immune complexes is therefore most likely the result of deletion of Fc receptors for these immune complexes. The role of complement in the initiation of this response was further assessed by complement depleting +/+ and −/− mice with cobra venom factor (7, 16) and then performing a reverse passive Arthus reaction. As shown in FIGS. 21A and 21B, the +/+ mice show the previously reported attenuation in the inflammatory response, whereas the residual inflammatory response found in the −/− mice was completely ablated, despite the fact that both had levels of hemolytic complement not significantly different from that of heat-inactivated (i.e. complement depleted) serum. From these studies it appears that the role of complement in initiating the immune complex mediated inflammatory response is secondary to that of Fc receptor engagement, although it is undoubtedly necessary for its full expression.

Neutrophils are another key element in the Arthus reaction, and a defect in neutrophil chemotaxis and function might thus be expected to cause an abnormal Arthus reaction. This is not the cause of the attenuated neutrophil response, however, because equivalently vigorous neutrophil exudation into the peritoneum of both +/+ and −/− mice was observed 4 hours after inducing nonspecific inflammation with intraperitoneal thioglycollate. In response to this inflammatory challenge +/+ mice generated $48.7 \times 10^6$ cells of which 64% were PMNs, while −/− mice had $46.3 \times 10^6$ cells, of which 59% were PMNs (17).

Deletion of the γ chain of the Fc receptor complex results in the loss of surface expression of FcγRI, FcγRIII and the IgE high affinity receptor, FcεRI. In order to eliminate the unlikely possibility that the absent IgE receptor is responsible for the attenuated response, the reverse passive Arthus reaction was performed on mice which lack only the α-subunit of this receptor yet have a normal complement of FcγR's (18). In these FcεRI deficient animals, a vigorous reverse passive Arthus reaction was elicited, comparable in magnitude to +/+ mice (not shown). Thus, while FcεRI is absolutely critical to the IgE mediated cutaneous and systemic anaphylaxis reactions (10, 18, 19), it is not necessary for inflammatory responses triggered by IgG immune complexes. The γ chain is also known to associate with the T cell receptor/CD3 complex. As shown (10), no defect in thymic or peripheral T cells are observed in the −/− mice, due to retention of the ζ chain, which can substitute for the function of the γ chain in TCR/CD3 assembly and signalling. No other immune receptors have been identified which require the presence of γ chain for their expression or function. In particular, none of the complement receptors assemble with this chain (20) and their ability to signal in vivo, as demonstrated in FIG. 20, argues against a defect in their function in the −/− mice.

Defining a new model of immune complex-mediated inflammation. While these studies strongly suggest a central role for the IgG Fc receptors in initiating the immune complex inflammatory response, the relevant Fc receptor-bearing cell types which are involved cannot be definitively assigned at this time. Several lines of evidence, however, suggest that the mast cell, which expresses FcγRII and FcγRIII, is a likely candidate. First, mast cells are found in high density in the skin and are favorably positioned around blood vessels; thus they are easily accessible to circulating immune complexes (9, 21). Second, mast cells have been shown to be important in the expression of such inflammatory processes as leukocyte infiltration and edema; in addition, they are known to store and release a variety of pro-inflammatory mediators, such as histamine, platelet-activating factor, leukotrienes, cyclooxygenases, and TNF-α, which can activate endothelium and can stimulate the production of neutrophil chemoattractants (21, 22). Third, indirect evidence from Benacerraf, et. al. (23) has shown that in response to circulating immune complexes, there is a striking increase in endothelial permeability in the skin and stomach, sites where mast cells are located in abundance. And last, recent work on mast cell deficient mice (11) has demonstrated that the attenuated reverse passive Arthus reaction in these mice is reconstituted by local replacement of wild-type mast cells.

While it is true that the FcRγ deficient mice are missing both FcγRI and FcγRIII, and that both receptors may contribute to the reaction, it is more likely that FcγRIII is the relevant receptor. FcγRI is a high affinity receptor, preferentially binding monomeric IgG, while FcγRIII interacts only with immune complexes and is expressed at high density on mast cells and macrophages. Preferential engagement of FcγRIII is observed when IgG immune complexes are presented to mast cells and macrophages, triggering their activation in vitro (9, 24).

Figure 22:
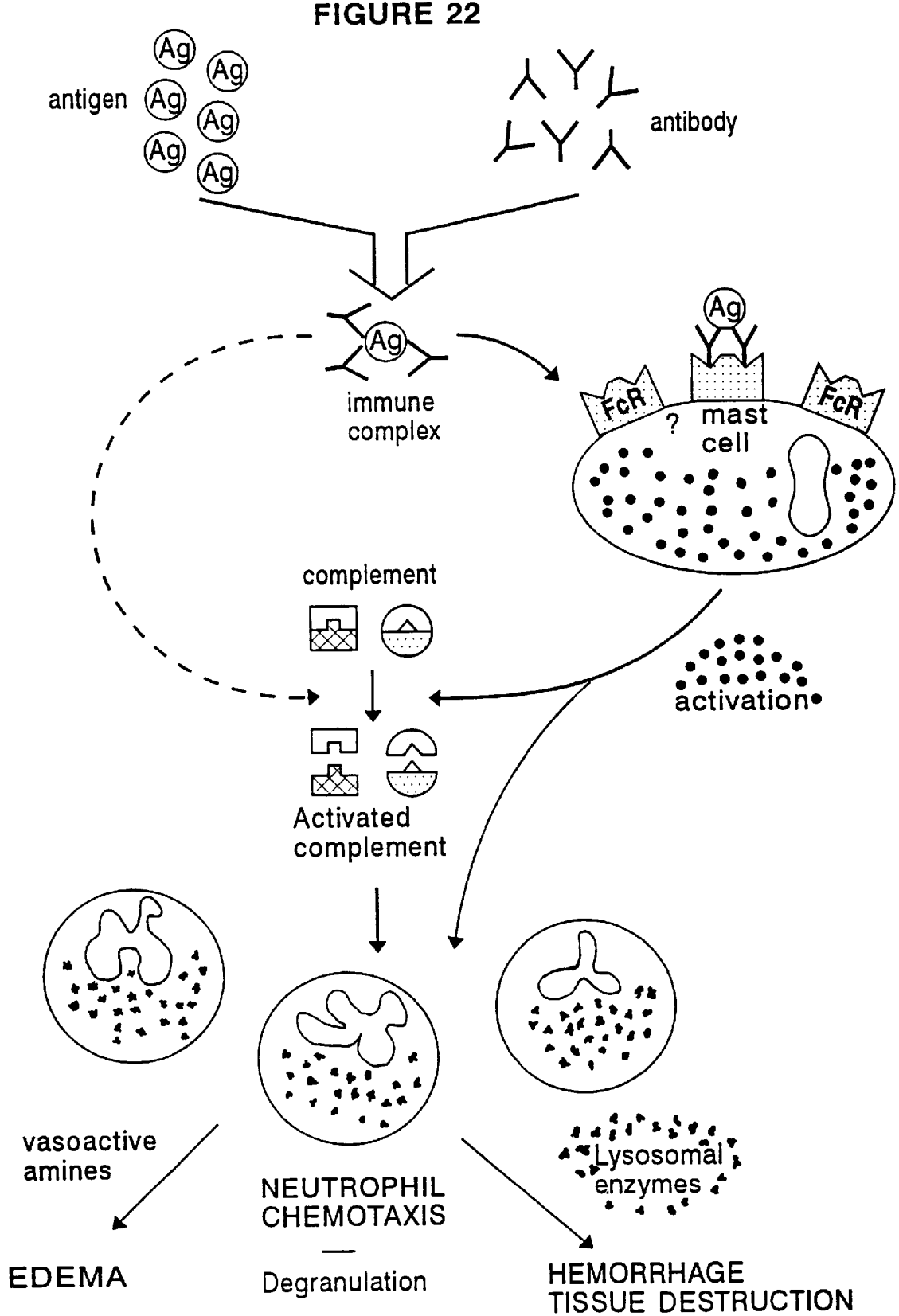

The model suggested by the studies presented here and in previous work on the inflammatory response to immune complexes is presented in FIG. 22. Several potential mechanisms are consistent with the data on the role of FcR cross-linking in initiating the inflammatory response to immune complexes. Triggering of mast cells could result in the release of preformed mediators, thereby increasing vascular permeability, activating complement and stimulating the local adhesion and migration of neutrophils. Alternatively, FcR cross-linking by immune complexes may directly result in the activation of complement components, along with known pro-inflammatory mediators, and thereby set off the cascade of events which culminates in the dramatic sequalea of the inflammatory response. The possibility that Fc and complement receptors act synergistically in initiating the inflammatory response, requiring that both be intact to trigger its full in vivo expression cannot be ruled out. In either case, inhibition of FcR cross-linking by immune complexes can be expected to dramatically attenuate the inflammatory response by targeting the initiation of the cascade, rather than its propagation and amplification.

References of the Fourth Series of Experiments

1. M. Arthus, *C. R. Soc. Biol.* 55, 817 (1903).

2. E. L. Opie, *J. Immunol.* 9, 247 (1924).

3. J. T. Culbertson, *J. Immunol.* 29, 29 (1935); P. R. Cannon and L. E. Marshall, *J. Immunol.* 40, 127 (1941); E. E. Fischel and E. A. Kabat, *J. Immunol.* 55, 337 (1947); B. Benacerraf and E. A. Kabat, *J. Immunol.* 64, 1 (1950).

4. C. G. Cochrane and W. O. Weigel, *J. Exp. Med.* 108, 591 (1958).

5. C. A. Stetson, *J. Exp. Med.* 94, 349 (1951); J. H. Humphrey, Brit. *J. Exp. Pathol.* 36, 268 and 283 (1955); C. G. Cochrane, W. O. Weigle, F. J. Dixon, *J. Exp. Med.* 110, 481 (1959).

6. P. A. Ward and C. G. Cochrane, Fed. *Proc., Fed. Amer. Soc. Exp. Biol.* 23, 509 (1964).

7. C. G. Cochrane and A. Janoff, in *The Inflammatory Process*, B. W. Zweifach, L. Grant, and R. T. McCluskey, Eds. (Academic Press, 1974), vol. III, chap. 3; Z. Ovary, *Int. Archs. All. Appl. Immunol.* 69, 385(1982); D. T. Fearon and W. W. Wong, *Ann. Rev. Immunol.* 1, 243 (1983); D. H. Perlmutter and H. R Colten, *Ann. Rev. Immunol.* 4, 231 (1986).

8. P. J. Bailey and D. S. Fletcher, in *Methods in Enzymology*, G. DiSabato, Ed. (Academic Press, Inc, San Diego, Calif., 1988), vol. 162, chap. 40.

9. J. V. Ravetch and J. P. Kinet, *Annu. Rev. Immunol.* 9, 457 (1991); J. V. Ravetch et al., *Science* 234, 718 (1986).

10. T. Takai, M. Li, D. Sylvestre, R. Clynes, J. V. Ravetch, *Cell* 76, 519 (1994).

11. Y. Zhang, B. F. Ramos, B. A. Jakschik, *J. Clin. Invest.* 88, 841 (1991); Y. Zhang, B. F. Ramos, B. A. Jakschik, *Science* 258, 1957 (1992).

12. P. P. Bradley, D. A. Priebat, R. D. Christensen, G. Rothstein, *J. Invest. Dermatol.* 78, 206 (1982).

13. C. M. Snapper and F. D. Finkelman, in *Fundamental Immunology*, W. E. Paul, Ed. (Raven Press, New York, 1993), chap. 22.

14. R. M. W. De Waal, G. Schrijver, M. J. J. T. Bogman, K. J. R. Assmann, R.-A. P. Koene, *Jour. Immunol. Meth.* 108, 213 (1988).

15. A. C. Issekutz and T. B. Issekutz, in *Methods in Enzymology*, G. Di Sabato, Ed. (Academic Press, Inc., San Diego, Calif., 1988), vol. 162, chap. 27.

16. C. G. Cochrane, J. J. Muller-Eberhard, B. S. Aikin, *J. Immunol.* 105, 55 (1970).

17. Mice were injected with 1 ml. of 5% thioglycollate intraperitoneally. Four hours later, the peritoneum was lavaged with PBS containing 0.1% fetal calf serum. The cellular material was then stained with acid hematoxylin.

18. D. Dombrowicz, V. Flamand, K. K. Brigman, B. H. Koller, J. P. Kinet, *Cell* 75, 969 (1993).

19. T. R. Martin, S. J. Galli, I. M. Katona, J. M. Drazen, *J. Clin, Invest.* 83, 1375 (1989).

20. M. Krych, J. P. Atkinson, V. M. Holers, *Curr. Opin. in Immunol.* 4(1), 8 (1992).

21. E. S. Schulman, *Crit. Rev. in Immunol.* 13(1), 35 (1993).

22. S. J. Galli, *New Engl. Jour. Med.* 328(4), 257 (1993); J. S. Pober, M. R. Slowik, L. G. DeLuca, A. J. Ritchie, *J. Immunol.* 150, 5114 (1993).

23. B. Benacerraf, R. T. McCluskey, D. Patras, *J. Immunol.* 35(1), 75 (1959).

24. R. B. Lobell, J. P. Arm, M. B. Raizman, K. F. Austen, H. R. Katz, *J. Biol. Chem.* 268(2), 1207 (1993); M. A. Cassatella, I. Anegon, M. C. Cuturi, P. Griskey, G. Trinchieri, and B. Perussia, *J. Exp. Med.* 169, 549 (1989); A. Froese, *Prog. Allergy.* 34, 142 (1984).

Fifth Series of Experiments

GENERATING ANIMALS CONTAINING HUMAN Fc RECEPTORS OR DOMAINS THEREOF

Technique A. The first step in generating a mouse, or other non-human animal species, capable of expressing a human Fc receptor (FcR), FcR subunit, or protein containing a domain of a human FcR is to construct a targeting vector. The targeting vector should contain a human FcR gene or appropriate artificial gene construct and homologous flanking sequences which will facilitate incorporation of the humanized gene in the mouse (or other animal) genome by homologous recombination. The construction of such a targeting vector is analogous to construction of the targeting vector described herein for generating a FcR gamma chain deficient mouse. Preferably the vector is initially constructed as a plasmid, and the plasmid sequences are subsequently removed. The second step is to transfect linearized vector into ES cells (Takai, et al., *Cell* (1994) 76: 519–529). ES cells are then microinjected into the blastocoel of blastocysts flushed from the uterus of naturally mated females. The blastocysts are then reimplanted into the uterus of pseudopregnant foster mothers at about day 2.5. Chimeric animals are detected by the presence of agouti patches on the black fur. Animals heterozygous or homozygous for the humanized FcR or FcR-based protein are then mated with mice incapable of expressing the analogous mouse FcR protein. Offspring are genotyped by genomic blotting to distinguish heterozygotes from homozygotes.

Technique B. Inject DNA of an expression construct which is defined as a fragment of DNA containing genomic sequences which direct the expression of RNA derived from this DNA to a particular cell type and DNA sequences encoding a human Fc receptor gene or portion thereof, and mouse sequences. This DNA was injected into the fertilized zygote according to established procedures to generate a transgenic animal. The zygote was implanted into a pseudopregnant foster mother to generate viable offspring. Mice containing the transgene were identified by genomic Southern blots of tail tip DNA utilizing DNA sequence probes specific to the human DNA elements. Transgenic mice generated in this way have been demonstrated to express human Fc receptor protein or portion thereof in a cell-type specific fashion. These transgenic mice expressing human Fc receptor protein or Fc receptor protein domain are mated to Fc receptor deficient mice, thereby reconstituting expression of a specific Fc receptor subunit or domain thereof in a mouse deficient for that subunit or domain. Progeny expressing the humanized receptor were identified by genomic Southern blotting and fluorescence-activated cell sorting of Fc receptor expressing cells using monoclonal antibodies specific for human Fc receptor proteins.

Crosslinking of FcγRIIIA on NK cells results in increases in $[Ca++]_i$, $IP_3$ turnover tyrosine phosphorylation, IL-2 production and IL-2 receptor expression. Similar findings were reported for FcγRIII crosslinking on mast cells and macrophages, although studies in those cells is always complicated by the presence of endogenous FcγRI and II, which makes assignment of a particular signalling pathway to a single FcγR difficult. In order to dissect the roles of specific domains of individual FcγRs involved in signal transduction required the development of a manipulable cell system, in which endogenous FcγRs would not confounding. FcγRs have been expressed in fibroblastic cells and bind ligand specifically, however, crosslinking of these receptors does not result in signalling. The ζ chain of the TCR/CD3 complex has been shown to be involved in signal transduction from that receptor. FcγRIII signalling in Jurkat T cells was reconstituted, as a model for FcγRIII signalling. Results obtained with that system were verified in P815 mast cells, since the human FcγRIII could be engaged independently of the endogenous murine FcγRs through the use of monoclonal Fabs to the transfected receptor.

FcγRIIIAα, γ chains were expressed by co-transfection in Jurkat cells and the subunit composition of the expressed receptors determined by immunoprecipitation. Only αγ complexes were observed, despite the presence of endogenous ζ chain, which was found to preferentially assemble with the TCR/CD3 chains. FcγRIIIB was also expressed by transfection into Jurkat cells and expressed as a GPI anchored molecule. Cytoplasmic deletions of α were expressed, as were chimeric molecules expressing α extracellular sequences and γ transmembrane and cytoplasmic sequences (α/γ). Stable cell lines were obtained and studied for FcγR induced signal transduction, as monitored by changes in [Ca++], IP3 turnover, tyrosine phosphorylation, IL-2 production and IL-2 receptor modulation. IIIAα+γ and α/γ chimeras were able to trigger these signalling events, while IIIB could not. Deletion of the cytoplasmic domain of α did not effect these responses, while truncation of the carboxy terminal 20 amino acids of the γ chain resulted in a receptor which was unable to mediate these signalling events.

FcγRIIIA and IIIB Expression were Faithfully Reconstituted in Transgenics

The genomic cosmid clones encoding human IIIA and IIIB were used to establish transgenic lines using standard procedures. These clones contain 5 kb of 5' flanking sequence, 15 kb of intron-exon sequence and 10 kb of 3' flanking sequence. Expression of the transgene (driven by its endogenous promoter) was assayed by RNA expression in transgene-bearing and non-transgenic littermates in a variety of hematopoietic and non-hematopoietic organs. Specificity of expression was determined by two-color FACS analysis of neutrophils, macrophages and lymphocytes. Peritoneal macrophages, either resident or elicited by thiogylocollate were analyzed for FcγRIII transgene expression using the monoclonal antibody 3G8, which is specific for the IIIA and B α chains and does not recognize the murine FcγRIIIa chain. A variety of macrophage markers were used, including F4/80. Only the IIIA transgenic line expressed a double positive population of F4/80/3G8 macrophages. Neutrophils isolated from the bone marrow of IIIA mice and identified by the marker RB6 (Gr-1) were negative for 3G8. Both neutrophils and macrophages from IIIA mice were positive for 2.4G2, the Mab which recognized the murine II and III gene products. In contrast, neutrophils from the IIIB transgenic line were positive for both RB6 (Gr-1) and 3G8, while the macrophages from these mice were negative for 3G8. PIPLC treatment of IIIB neutrophils eliminated the 3G8 staining of these cells, indicating that the IIIB transgene was expressed as a GPI anchored protein in these murine neutrophils.

Two types of sutdies have been pursued to begin to dissect the DNA sequences regulating transcription of FcγRs: 1) Promoter characterization of FcγR-receptor constructs transfected into macrophage, lymphocyte and fibroblastic cell lines and 2) Construction of transgenic mice utilizing the endogenous genomic sequences to drive expression of human FcγRs. Studies have cnocentrated on the murine FcγRII and III genes and the human FcγRI and III genes. Transcriptional initiation sites were mapped for these genes in the appropriate cell types and reporter constructs transfected into cell lines expressing the endogenous gene, and compared to cell lines in which the endogenous gene was not expressed. For example, a 1.1 kb fragment 5' of the human FcγRI gene, containing the multiple initiation sites was used to drive bacterial CAT and transfected into U937 (human myelomonocytic line), RAW (murine macrophage line) and HeLa (human fibroblastic line) cells. Expression of CAT activity was observed only in response to IFN-γ and only in U937 and RAW cells. A sequence element has been defined responsible for IFN-γ induction (GRR,29) and a more 3' sequence which appears to behave as a constituative promoter in U937 and RAW cells. Similar studies have been performed on the murine FcγRII promoter expressed in A20(B) cells, and FcγRIII expressed in RAW (macrophage) and HL-60/DMSO (neutrophil) cell lines.

Cell type restricted expression in vivo has been pursued using the intact genomic clones for human FcγRIIA, B, C, FcγRIIIA and B to derive transgenic lines. Characterization of IIIA and B are described above; analysis of the FcγII mice is underway. Transgenics have been generated in which the putative regulatory sequences have been exchanged: 5 kb of 5' flanking sequences derived from the IIIA gene have been ligated in place of the corresponding sequences of the IIIB gene (5'IIIA-IIIB3') and conversely, the 5 kb of 5' flanking sequences of IIIA have been substituted for similar sequences of the IIIB gene (5'IIIB-IIIA3'). $f_1$ mice have been obtained and are being characterized for macrophage and neutrophil specific expression.

Crosses of humanized and knockout mice:

The following crosses of mice will be made:

A. A mouse with expressing FcγIIIA (hu FcγIIIA) wil be mated with a mouse that does not express FcγIIIA (FcγIIIA knockout). (This cross is expressed as follows: hu FcγIIIA×FcγIIIA knockout. The following crosses are represented analogously).

hu FcγIIIB×FcγIIIAα knockout

B. hu FcγRIIA×FcR γ-chain knockout

FcγRIIB knockout×hu FcγRIIB

FcγRIIB knockout×hu FcγRIIC

C. FcγRI knockout×hu FcγRIA

FcγRI knockout×hu FcγRIB

FcγRI knockout×hu FcγRIC

D. A mouse which does not express any Fcγ receptor or Fcε receptor will be crossed with a mouse containing all human Fc receptors. (Fc knockout×hu Fc).

What is claimed is:

1. A non-naturally occurring transgenic mouse that does not express a functional γ subunit of the Fc receptor, wherein said mouse is characterized by a substantial reduction in the ability to produce an inflammatory response in comparison to a mouse that expresses a functional γ subunit of the Fc receptor.

2. The mouse of claim 1, wherein the Fc receptor is selected from the group consisting of FcγRI, FcγRIII, and FcεRI.

3. The mouse of claim 1, wherein the inflammatory response is an inflammatory response to cytotoxic antibodies.

4. The mouse of claim 1, wherein the inflammatory response is an inflammatory response to immune complex deposition.

5. The mouse of claim 4, wherein the inflammatory response is selected from the group consisting of anaphylaxis; hemorrhage; neutrophil infiltration; edema; phagocytosis; killer-cell mediated lysis; asthma; and rash.

6. The method of claim 4, wherein the proinflammatory agent is administered intravenously, intraperitoneally, intrathecally, intradermally, intramuscularly, topically, orally, or by inhalation.

7. A method of identifying a proinflammatory agent dependent on a functional Fc receptor having a γ subunit, comprising:

administering to a mouse that expresses a functional Fc receptor and to the mouse of claim 1, an amount of a proinflammatory agent that induces an inflammatory response in the mouse that expresses a functional Fc receptor; and determining whether the inflammatory response in the mouse of claim 1 is reduced relative to the inflammatory response observed in the mouse that expresses a functional Fc receptor, wherein a reduced inflammatory response in the mouse of claim 1 indicates that the proinflammatory agent is dependent upon a functional Fc receptor having a γ subunit.

8. The method of claim 7, wherein the mouse that does not express the functional Fc receptor selected from the group consisting of FcγRI, FcγRIII, and FcεRI displays substantially no inflammatory response to the proinflammatory agent.

9. The method of claim 7, wherein the inflammatory response is anaphylaxis.

10. The method of claim 9, wherein the proinflammatory agent is IgE immune complex.

11. The method of claim 9, wherein the proinflammatory agent is IgG immune complex.

12. The method of claim 7, wherein the inflammatory response is selected from the group consisting of edema, hemorrhage, and neutrophil infiltration.

13. The method of claim 12, wherein theproinflammatory agent is an IgG immune complex.

14. The method of claim 7, wherein the inflammatory response is type II acute inflammation.

15. The method of claim 14, wherein the proinflammatory agent is a cytotoxic autoantibody.

16. A method for identifying a proinflammatory agent not dependent on a functional Fc receptor having a γ subunit, comprising:

administering to the mouse of claim 1 an amount of the proinflammatory agent effective to induce an inflammatory response; and detecting an inflammatory response in the mouse of claim 1, thereby identifying the proinflammatory agent not dependent on the functional Fc receptor having the γ subunit.

17. The method of claim 16, wherein the Fc receptor is selected from the group consisting of FcγRI, FcγRIII, and FcεRI.

18. A method of determining an antiinflammatory agent that is dependent upon a functional Fc receptor having a γ subunit, comprising:

(a) administering to a first mouse that expresses a functional Fc receptor and to a second mouse according to claim 1, an amount of a proinflammatory agent that induces a greater inflammatory response in the first mouse than in the second mouse;

(b) administering to the first and second mouse that manifest an inflammatory response to the proinflammatory agent an anti-inflammatory agent; and (c) determining whether a decreased inflammatory response in the first mouse is not observed in the second mouse;

wherein the lack of response of the second mouse to the anti-inflammatory agent indicates that the anti-inflammatory agent is dependent upon a functional Fc receptor having a γ subunit.

* * * * *